United States Patent
Shimizu et al.

(10) Patent No.: US 12,303,200 B2
(45) Date of Patent: May 20, 2025

(54) DIAGNOSIS SUPPORT DEVICE, DIAGNOSIS SUPPORT SYSTEM, AND PROGRAM

(71) Applicant: OUI INC., Tokyo (JP)

(72) Inventors: Eisuke Shimizu, Tokyo (JP); Hiroyuki Yazu, Tokyo (JP); Naohiko Aketa, Tokyo (JP); Shintaro Nakayama, Tokyo (JP); Akito Sakasegawa, Tokyo (JP); Makoto Tanji, Tokyo (JP); Takayuki Ueda, Tokyo (JP)

(73) Assignee: OUI INC., Tokyo (JP)

( * ) Notice: Subject to any disclaimer, the term of this patent is extended or adjusted under 35 U.S.C. 154(b) by 515 days.

(21) Appl. No.: 17/799,043

(22) PCT Filed: Feb. 15, 2021

(86) PCT No.: PCT/JP2021/005447
§ 371 (c)(1),
(2) Date: Aug. 11, 2022

(87) PCT Pub. No.: WO2021/162124
PCT Pub. Date: Aug. 19, 2021

(65) Prior Publication Data
US 2023/0092251 A1 Mar. 23, 2023

(30) Foreign Application Priority Data
Feb. 14, 2020 (JP) .................................. 2020-023514

(51) Int. Cl.
*A61B 3/14* (2006.01)
*A61B 3/00* (2006.01)
(Continued)

(52) U.S. Cl.
CPC .............. *A61B 3/14* (2013.01); *A61B 3/0025* (2013.01); *A61B 3/135* (2013.01); *A61B 5/6898* (2013.01); *A61B 5/7267* (2013.01); *G16H 30/40* (2018.01)

(58) Field of Classification Search
CPC ......... A61B 3/0025; A61B 3/10; A61B 3/135; A61B 3/14; A61B 5/6898; A61B 5/7267; G16H 30/40
See application file for complete search history.

(56) References Cited

FOREIGN PATENT DOCUMENTS

| WO | 2010/117386 A1 | 10/2010 |
| WO | 2019/146792 A1 | 8/2019 |

OTHER PUBLICATIONS

Extended European Search Report dated Jun. 22, 2023, issued in European Application No. 21752926.2.

*Primary Examiner* — Jack Dinh
(74) *Attorney, Agent, or Firm* — Sughrue Mion, PLLC

(57) ABSTRACT

A close-up imaging device that generates slit light on the basis of light-source light emitted from a light source built into a mobile communication terminal device. The close-up imaging device is mounted onto the mobile communication terminal device, and a moving image of the tissue to be observed of the examined eye is captured by a camera module built into the mobile communication terminal device. Then, in a diagnosis support server device, a diagnosable frame image included in the captured moving image is extracted, at least one of a heath state of the examined eye and any one or more of a distance, an angle, and an area in some tissue of the examined eye is estimated on the basis of the diagnosable frame image extracted, and diagnosis support information is generated and distributed to the corresponding mobile communication terminal device.

18 Claims, 27 Drawing Sheets

(51) Int. Cl.
*A61B 3/135* (2006.01)
*A61B 5/00* (2006.01)
*G16H 30/40* (2018.01)

FIG. 18A
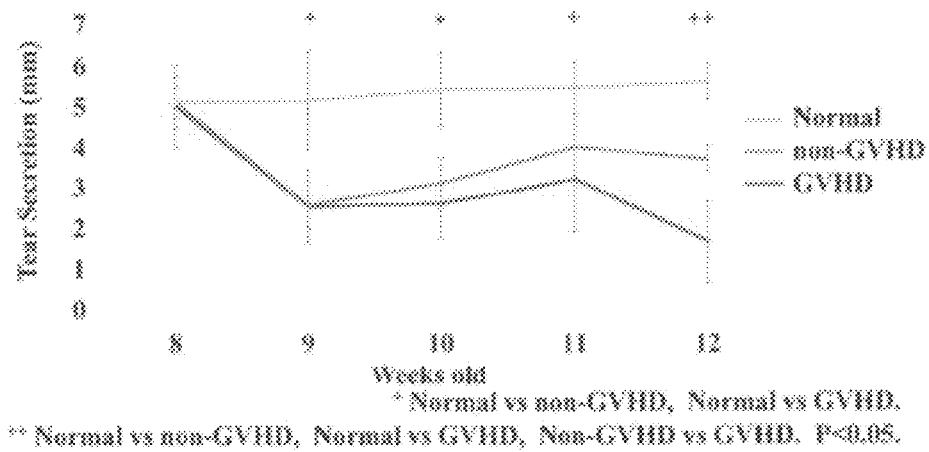
FIG. 18B
FIG. 19A
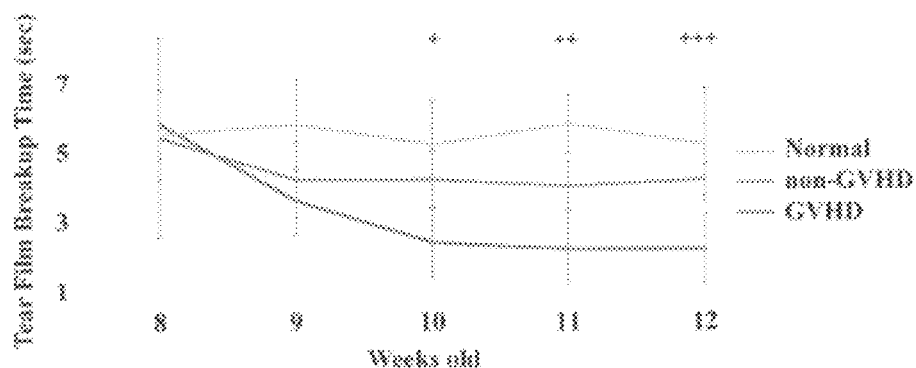

FIG. 19B
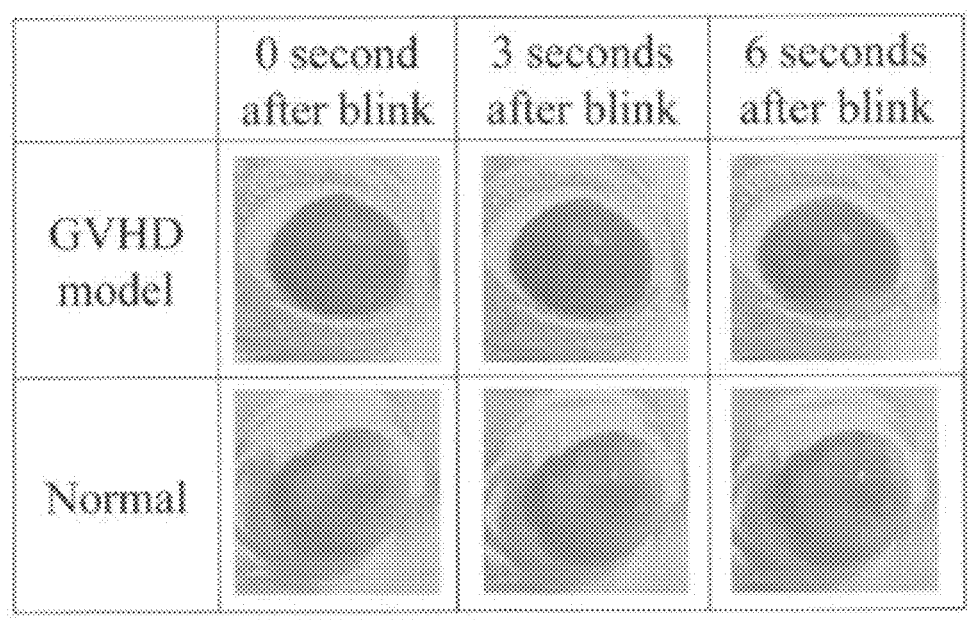
FIG. 20
FIG. 21A
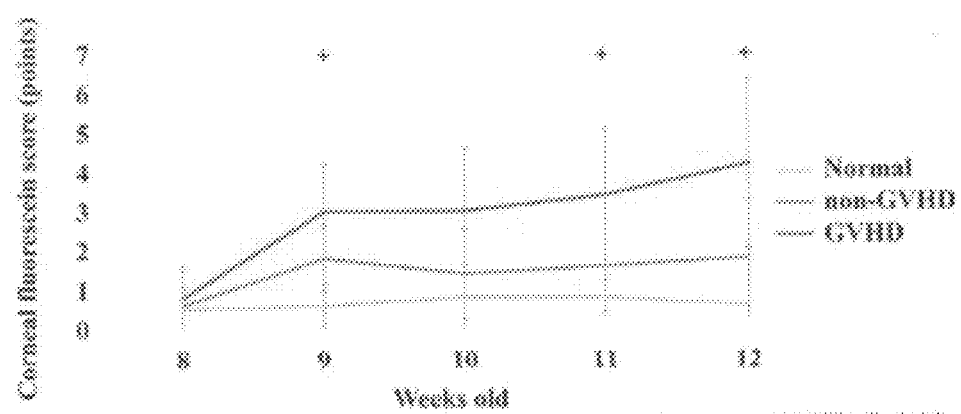

FIG. 21B
FIG. 22A
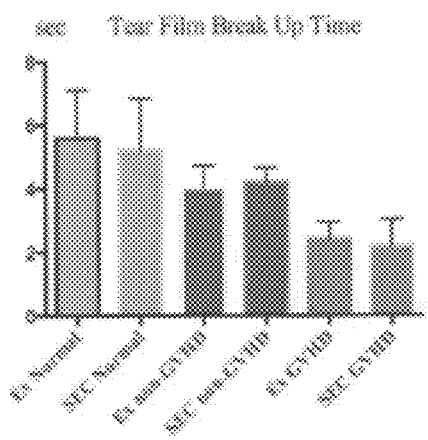
FIG. 22B
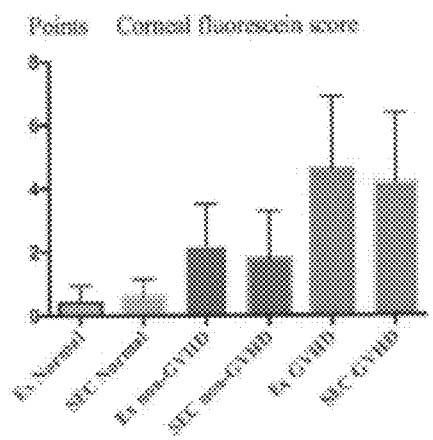

FIG. 22C

|  |  | Normal | non-GVHD | GVHD | | P-value* | |
|---|---|---|---|---|---|---|---|
|  |  |  |  |  | Normal | non-GVHD | GVHD |
| TFBUT | Ex | 5.60 ± 1.52 | 4.00 ± 0.71 | 2.40 ± 0.55 | 0.500 | 0.999 | 0.999 |
|  | SEC | 5.20 ± 1.64 | 4.20 ± 0.45 | 2.20 ± 0.84 |  |  |  |
| CFL | Ex | 0.40 ± 0.55 | 2.30 ± 1.30 | 4.60 ± 2.30 | 0.999 | 0.750 | 0.500 |
|  | SEC | 0.60 ± 0.55 | 1.80 ± 1.48 | 4.20 ± 2.17 |  |  |  |

Data are shown by mean ± SD. Female, BALB/cCrSlc mice, n = 5.
Ex: Existing device. SEC: Smart Eye Camera.
*P-value: Existing device vs Smart Eye Camera, Wilcoxon test.

FIG. 23A

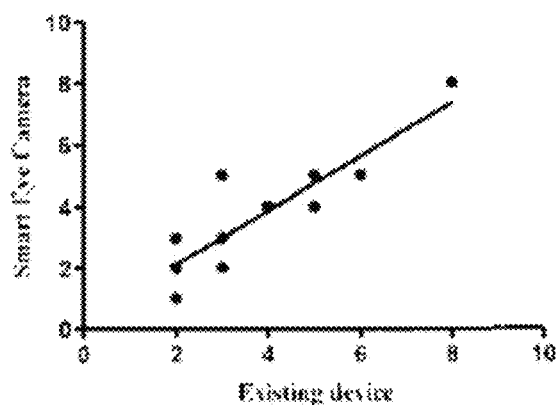

Tear Film Breakup Time $P < 0.001$, $r = 0.871$
Pearson's correlation coefficient

FIG. 23B

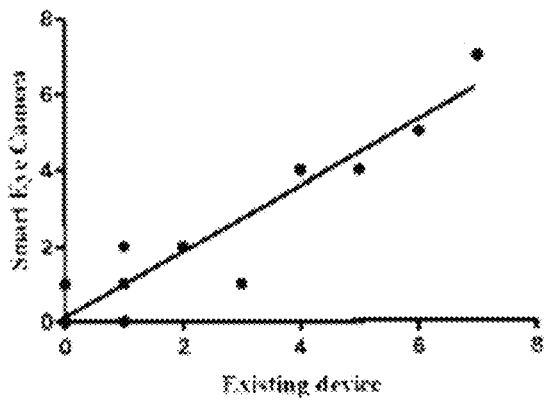

Corneal Fluorescein Score $P < 0.001$, $r = 0.941$
Pearson's correlation coefficient

|  |  | Normal | non-GVHD | GVHD | Normal | P-value* non-GVHD | GVHD |
|---|---|---|---|---|---|---|---|
| TS | R | 5.60 ± 0.42 | 3.70 ± 0.33 | 1.65 ± 1.01 | 0.381 | 0.999 | 0.984 |
|  | L | 5.20 ± 0.57 | 3.70 ± 0.41 | 1.75 ± 1.05 |  |  |  |
| TFBUT | R | 5.20 ± 1.64 | 4.20 ± 0.45 | 2.20 ± 0.84 | 0.999 | 0.278 | 0.635 |
|  | L | 5.40 ± 1.55 | 3.60 ± 0.55 | 1.80 ± 0.45 |  |  |  |
| CFS | R | 0.60 ± 0.55 | 1.80 ± 1.48 | 4.20 ± 2.17 | 0.524 | 0.881 | 0.999 |
|  | L | 0.40 ± 0.89 | 1.80 ± 0.45 | 4.20 ± 1.48 |  |  |  |

Data are shown by mean ± SD. Female, BALB/cCrSlc mice, n = 5.
*P value: Right vs Left, Mann-Whitney U test.

Figure. Amout of TFBUT by groups

TFBUT: Tear Film Break Up Time
*P < 0.05, Mann-Whitney test.

(i) EXTRACT DIAGNOSABLE FRAME IMAGES
(ii) DETECT AND CUT OUT IRIS PORTION
(iii) TAG ACD:3.149mm (AL:32mm)
(iv) ESTIMATE ANTERIOR CHAMBER DEPTH ERROR 150 ± 360 μm LEARN NUMERICAL VALUE OF ANTERIOR CHAMBER DEPTH MEASURED BY ANTERIOR EYE OCT IN MOVING IMAGE CAPTURED BY SMART EYE CAMERA

DIAGNOSIS SUPPORT DEVICE, DIAGNOSIS SUPPORT SYSTEM, AND PROGRAM

CROSS REFERENCE TO RELATED APPLICATIONS

This application is a National Stage of International Application No. PCT/JP2021/005447 filed Feb. 15, 2021, claiming priority based on Japanese Patent Application No. 2020-023514 filed Feb. 14, 2020.

FIELD OF THE INVENTION

The present invention relates to a diagnosis support device and the like that support medical diagnosis by processing a medical image, and in particular to a diagnosis support device and the like that process a diagnostic image in the field of human and animal ophthalmology and, on the basis of the diagnostic image, support diagnosis of a disease in an eye of a patient (or affected animal) to be examined or measure at least one or more of a distance, an angle, and an area in some tissue of the examined eye.

BACKGROUND ART

In recent years, with the rapid development of machine learning methods such as deep learning and the rapid improvement of artificial intelligence (AI) performance, AI is expected to be applied to various fields, and methods of applying AI to the medical field have also been proposed (Patent Document 1, for example).

In an ophthalmic system set forth in this Patent Document 1, an information processing system (server device) is connected to a plurality of ophthalmic imaging devices installed in eye care facilities such as hospitals directly or via a network, and the information processing system performs machine learning on the basis of ophthalmic diagnostic images captured by the ophthalmic imaging devices to acquire image diagnostic knowledge. Then, in this ophthalmic system, a configuration is adopted in which, when an examined-eye diagnostic image is transmitted from an ophthalmic imaging device after knowledge acquisition by the information processing system, information such as suspected disease name, presence or absence of a specific disease, severity, necessity of examination, type of examination, necessity of surgery, and type of surgery are inferred on the basis of the image and acquired knowledge, and diagnosis support information including the inference results are automatically generated and distributed for use in an ophthalmic examination device.

PRIOR ART DOCUMENTS

Patent Documents

Patent Document 1: Japanese Laid-Open Patent Application Publication No. 2019-24738

SUMMARY OF THE INVENTION

Problems to be Solved by the Invention

Nevertheless, the system described in the above-described Patent Document 1 is configured to capture a diagnostic image by the ophthalmic imaging device installed in a facility such as a hospital. This type of ophthalmic imaging device is expensive and difficult to handle, and poses difficulties in capturing images that can be utilized for diagnosis if not a physician, an orthoptist, or other specialist with expert knowledge (hereinafter referred to as "physician or (physicians and) the like"). For this reason, in regions such as developing countries and remote places where equipment, physicians, and the like are in short supply, it is difficult to acquire an image that can be utilized for diagnosis, and generate diagnosis support information. Further, information parameter values including at least one or more of distance, angle, and area in some tissue of the examined eye cannot be measured by a physician or the like without the use of an advanced ophthalmic device, and cannot be measured at all in some regions.

The present invention has been made in light of the circumstances described above, and an object thereof is to provide a diagnosis support device and the like that reliably generate and make diagnosis support information related to an examined eye available, even in regions where equipment, physicians, and the like are in short supply.

Means for Solving the Problems (1) To solve the problems mentioned above, a diagnosis support device of the present invention includes acquisition means, first storage means, first extraction means, second storage means, estimation means, generation means, and distribution means. The acquisition means acquires an image of an examined eye captured by a mobile communication terminal device with a close-up imaging device mounted thereto. The mobile communication terminal device includes a light source, and an imaging camera lens. The close-up imaging device includes at least (a) an observation light irradiating member that irradiates tissue to be observed of the examined eye with, as observation light, any one of slit light, blue light, and linearly polarized light generated on the basis of light-source light emitted from the light source, or irradiates the tissue to be observed with, as the observation light, the light-source light passed as is, and (b) a convex lens member that concentrates, of the observation light, light including reflected light in the tissue to be observed, on the imaging camera lens. The captured image includes one or more first frame images that can be utilized for estimating at least one of (i) a health state of the examined eye, and (ii) one or more information parameter values including any one or more of a distance, an angle, and an area in some tissue of the examined eye. The first storage means stores, in advance, first knowledge for extracting the one or more first frame images from the captured image acquired. The first extraction means extracts, on the basis of the first knowledge, the one or more first frame images included in the captured image acquired. The second storage means stores, on the basis of the captured image, second knowledge for estimating at least one of (i) the health state of the examined eye, and (ii) the one or more information parameter values. The estimation means estimates, on the basis of the one or more first frame images extracted and the second knowledge, at least one of (i) the health state of the examined eye reflected in the captured image acquired, and (ii) the one or more information parameter values. The generation means generates diagnosis support information including at least one of the health state of the examined eye and the one or more information parameter values estimated. The distribution means distributes the diagnosis support information generated to an external equipment.

With this configuration, the close-up imaging device irradiates the tissue to be observed with the light-source light emitted from the light source of the mobile communication terminal device as the observation light as is, or converts the light-source light to and irradiates the tissue to be observed with any one of slit light, blue light, or linearly polarized light as the observation light. Then, when a user captures an image of the examined eye by a camera module mounted onto the mobile communication terminal device while irradiating the tissue to be observed (eyelid, eye surface, cornea, conjunctiva, lens, anterior chamber, anterior eye tissue including iris, and fundus tissue, for example) of the examined eye with the observation light, light including, of the observation light, reflected light of the examined eye is condensed by the close-up imaging device on the imaging camera lens of the mobile communication terminal device, making it possible to capture a moving image reflecting the tissue to be observed of the examined eye.

The camera module of the mobile communication terminal device can be operated in the same way as existing smartphones and the like, and thus, by using the mobile communication terminal device equipped with the close-up imaging device (hereinafter also referred to as a "smart eye camera"), it is possible to easily capture a moving image including the one or more first frame images that can be utilized for diagnosing the examined eye (hereinafter also referred to as "diagnosable frame images"), even by users other than physicians and the like (paramedics as well as laypersons such as family members, friends, and patients themselves, for example) who are not familiar with handling existing ophthalmic imaging devices.

Here, to utilize the captured image in an ophthalmic diagnosis, it is necessary to capture an image that satisfies all of the following three conditions: (Condition 1) The tissue to be observed of the examined eye is irradiated with the observation light, (Condition 2) at least a portion of the tissue to be observed is reflected along with, of the observation light irradiated, the reflected light of the tissue to be observed, and (Condition 3) the tissue to be observed is in focus. On the other hand, in a case in which the user uses a smart eye camera to capture the examined eye, during a period of several seconds to several tens of seconds, for example, when a moving image of the examined eye is captured, as long as the user can create a state that satisfies the above-described three conditions even for a time period corresponding to one frame (0.033 seconds at a frame rate of 30 fps, for example), a moving image including at least one diagnosable frame image that can be utilized for ophthalmic diagnosis can be captured. In particular, in a case in which a smart eye camera is used, an auto-focus mechanism installed in the camera module of the mobile communication terminal device can automatically focus on the object to be captured. Accordingly, the user can, with extreme ease, capture a moving image including the diagnosable frame image that satisfies all of the above-described three conditions by creating a state in which the tissue to be observed of the examined eye is irradiated with the observation light and capturing the examined eye with the reflected light of the observation light included. It should be noted that the examined eye does not necessarily have to be a human eye, and may be an eye of an animal (dog, cat, mouse, or the like). Further, in a case in which the information parameter values related to the examined eye are to be estimated, predetermined additional conditions are required, which will be discussed in detail below.

On the other hand, in a case in which the user is unfamiliar with capturing an image for diagnosis, there is a high possibility that the user will capture a moving image including many miscellaneous frame images that do not satisfy all of the above-described three conditions, and the moving image cannot be used to estimate the health state of the examined eye as is. Therefore, a configuration is adopted in which the diagnosis support device of the present invention automatically extracts, from among the plurality of frame images constituting the moving image, the diagnosable frame images that satisfy the above-described three conditions, on the basis of the first knowledge, estimates at least one of the health state of the examined eye and the information parameter values on the basis of the diagnosable frame images extracted, and generates diagnosis support information including at least one of the health state and the information parameter values estimated. With this configuration, the diagnosis support device of the present invention can accurately estimate at least one of the health state of the examined eye and the information parameter values on the basis of the captured image, even when the examined eye is captured by a user unfamiliar with photography, such as a layperson. Therefore, according to the diagnosis support device of the present invention, it is possible to reliably generate and utilize the diagnosis support information without influence by the user, region, and the like. Further, a configuration may be adopted in which the close-up imaging device mounted onto the mobile communication terminal device need only include at least the observation light irradiating member and the convex lens, making it possible to manufacture the device at a very low cost, and reliably generate and utilize the diagnosis support information including at least one of the health state of the examined eye and the information parameter values even in regions where expensive ophthalmic imaging device cannot be provided.

(2) Further, in the above-described configuration, a configuration may be adopted in which the first extraction means calculates a probability of each frame image included in the captured image qualifying as the first frame image on the basis of the frame images included in the captured image and the first knowledge, and extracts the first frame image on the basis of the calculated probability.

Although the possibility of extraction of unintended images cannot be eliminated when extracting images using machine learning, an accuracy and a reproducibility during diagnosable frame image extraction can be improved by extracting diagnosable frame images on the basis of the probability of qualifying as a diagnosable frame image. It should be noted that the criteria for extracting diagnosable frame images on the basis of the calculated probability are as desired and, for example, a certain top number of frames with high probability (for example, the best frame with the highest probability, the top five frames with the high probability, the frame images of the top few percent with high probability, or the like) may be extracted as the diagnosable frame images.

(3) Further, in the configuration described in claim 2, a configuration may be adopted in which the first extraction means extracts, as the one or more first frame images, a plurality of the frame images with the calculated probability being high, and the estimation means estimates at least one of (i) the health state of the examined eye and (ii) the one or more information parameter values for each of the one or more first frame images on the basis of the plurality of first frame images extracted and the second knowledge, and estimates at least one of a most plausible health state of the examined eye and the one or more information parameter values while weighting, by the calculated probability, the health state and the one or more information parameter values estimated.

With this configuration, the diagnosis support device of the present invention can estimate the most plausible health state of the examined eye and the information parameter values while weighting each frame image included in the moving image by the probability of qualifying as a diagnosable frame image. In general, estimation results of a health state or the like based on diagnosable frame images having a high probability of qualifying as diagnosable frame images have a correct answer rate higher than estimation results of a health state or the like based on diagnosable frame images having a lower probability. Accordingly, by weighting the estimation results based on each diagnosable frame image by the probability of qualifying as a diagnosable frame image, it is possible to estimate the most plausible health state of the examined eye and the information parameter values while increasing the weight of the estimation results having a high correct answer rate, and thus improve the reliability of diagnosis support information.

Normally, when a classifier is used to estimate the health state or the like of the examined eye on the basis of each diagnosable frame image, the classifier can estimate the correct answer at predetermined accuracy and reproducibility levels, but when the health state or the like is estimated on the basis of one diagnosable frame image, it becomes difficult to achieve a correct answer rate that exceeds the accuracy or reproducibility of a single classifier. On the other hand, in a case in which the above-described configuration is adopted, a plurality of estimation results can be obtained based on a plurality of diagnosable frame images, and the final estimation result can be determined while weighting the estimation results. As a result, the diagnosis support device of the present invention can estimate the most plausible health state of the examined eye and the information parameter values with higher accuracy and reproducibility than estimation by a single classifier, thereby improving the reliability of the diagnosis support information. It should be noted that the specific method of the above-described weighting process is as desired and, for example, ensemble machine learning may be applied to a plurality of estimation results obtained on the basis of each diagnosable frame image.

(4) Further, in the configuration described in any one of claims 1 to 3, a configuration may be adopted in which the acquisition means acquires the captured image captured while at least one of an eyelid or an anterior eye tissue of the examined eye is irradiated with the slit light generated on the basis of the light-source light as the observation light, the first storage means stores, in advance, as the first knowledge, knowledge for extracting the one or more first frame images that can be utilized for estimating at least one of (i) a state of a disease that develops in the eyelid and the anterior eye tissue of the examined eye, and (ii) the one or more information parameter values related to the eyelid and the anterior eye tissue, the second storage means stores, as the second knowledge, knowledge for estimating at least one of (i) the state of the disease that develops in the eyelid and the anterior eye tissue of the examined eye, and (ii) the one or more information parameter values related to the eyelid and the anterior eye tissue, and the estimation means estimates, on the basis of the one or more first frame images extracted and the second knowledge, at least one of (i) the state of the disease in at least one of the eyelid and the anterior eye tissue of the examined eye, and (ii) the one or more information parameter values related to the eyelid and the anterior eye tissue.

With this configuration, the diagnosis support device of the present invention can estimate the state of a disease that develops in at least one of the eyelid and anterior eye of the examined eye and information parameter values related to these tissues, and generate and make the diagnosis support information including the estimation results available. It should be noted that, in a case in which the slit light is used as the observation light, it is possible to observe the state of a disease and the like in each tissue of the eyelid, eye surface, cornea, conjunctiva, anterior chamber, and lens as the anterior eye tissues of the examined eye, as well as observe diseases that developed in a some fundus tissue or estimate the information parameter values of the fundus tissue.

(5) Further, in the configuration described in any one of claims 1 to 3, a configuration may be adopted in which the acquisition means acquires the captured image captured while irradiating at least one of a cornea and a conjunctiva of the examined eye with the blue light generated on the basis of the light-source light as the observation light, with an injury that occurred in a tissue of at least one of the cornea and the conjunctiva of the examined eye being contrasted by a contrast medium, the first storage means stores, in advance, as the first knowledge, knowledge for extracting the one or more first frame images that can be utilized for diagnosis of the state of the injury that occurred in the tissue of at least one of the cornea and the conjunctiva of the examined eye, the second storage means stores, in advance, as the second knowledge, knowledge for estimating a state of a disease in at least one of the cornea and the conjunctiva from the state of the injury that occurred in the tissue of at least one of the cornea and the conjunctiva of the examined eye, and the estimation means estimates, on the basis of the one or more first frame images extracted and the second knowledge, the state of the disease in at least one of the tissues of the cornea and conjunctiva of the examined eye.

With this configuration, the diagnosis support device of the present invention can estimate the state of a disease in at least one of the cornea and the conjunctiva of the examined eye from the state of an injury that occurred in the tissue of at least one of the cornea and conjunctiva, and generate and make the diagnosis support information including the estimation results available.

(6) Further, in the configuration described in any one of claims 1 to 3, a configuration may be adopted in which the acquisition means acquires the captured image captured while fundus tissue of the examined eye is irradiated with the linearly polarized light generated on the basis of the light-source light as the observation light, the first storage means stores, in advance, as the first knowledge, knowledge for extracting the one or more first frame images that can be utilized for estimating at least one of (i) a state of a disease that develops in the fundus tissue of the examined eye, and (ii) the one or more information parameter values related to the fundus tissue, the second storage means stores, as the second knowledge, knowledge for estimating at least one of (i) the state of the disease in the fundus tissue of the examined eye, and (ii) the one or more information parameter value related to the fundus tissue, and the estimation means estimates, on the basis of the one or more first frame images extracted and the second knowledge, at least one of (i) the state of the disease in the fundus tissue of the examined eye, and (ii) the one or more information parameter values related to the fundus tissue.

With this configuration, the diagnosis support device of the present invention can estimate at least one of the state of a disease in the fundus tissue of the examined eye and the information parameter values related to the fundus tissue, and generate and make the diagnosis support information including the estimation results available.

(7) Further, in the configuration described in any one of claims 1 to 3, a configuration may be adopted in which the acquisition means acquires the captured image captured while tissue to be observed of the examined eye is irradiated with the light-source light as the observation light as is, the first storage means stores, in advance, as the first knowledge, knowledge for extracting the one or more first frame images that can be utilized for estimating at least one of (i) a state of a disease that develops in tissue of at least one of an eyelid, an eye surface, a cornea, and a conjunctiva of the examined eye, and (ii) the one or more information parameter values related to the tissue of at least one of the eyelid, the eye surface, the cornea, and the conjunctiva of the examined eye, the second storage means stores, in advance, as the second knowledge, knowledge for estimating at least one of (i) the state of the disease in the tissue of at least one of the eyelid, the eye surface, the cornea, and the conjunctiva of the examined eye, and (ii) the one or more information parameter values related to the tissue of at least one of the eyelid, the eye surface, the cornea, and the conjunctiva of the examined eye, and the estimation means estimates, on the basis of the one or more first frame images extracted and the second knowledge, at least one of (i) the state of the disease in the tissue of at least one of the eyelid, the eye surface, the cornea, and the conjunctiva of the examined eye, and (ii) the one or more information parameter values related to the tissue of at least one of the eyelid, the eye surface, the cornea, and the conjunctiva of the examined eye.

With this configuration, the diagnosis support device of the present invention can estimate at least one of the state of a disease in the tissue of at least one of the eyelid, the eye surface, the cornea, and the conjunctiva of the examined eye and the information parameter values related to these tissues while irradiating the tissue to be observed with the light-source light as the observation light as is, and generate and make the diagnosis support information including the estimation results available.

(8) Further, in the configuration described in any one of claims 1 to 7, a configuration may be adopted in which the diagnosis support device of the present invention further comprises learning means for acquiring the second knowledge by executing at least one of machine learning and data mining on the basis of the one or more first frame images extracted by the first extraction means, and storing the second knowledge acquired in the second storage means, and the estimation means estimates, on the basis of the second knowledge stored in the second storage means by the learning means and the one or more first frame images extracted, at least one of the state of a disease of the examined eye and the one or more information parameter values.

With this configuration, the diagnosis support device of the present invention can acquire the second knowledge while executing at least one of machine learning and data mining on the basis of the diagnosable frame images extracted by the first extraction means, thereby reducing the effort required to provide the second knowledge to the diagnosis support device. It should be noted that the specific method of acquiring the second knowledge is as desired and, for example, the system may be configured to present the diagnosable frame images extracted by the first extraction means to a plurality of physicians, who are annotators, and obtain the diagnosis results of the physicians based on the diagnosable frame images, and thus input the diagnosable frame images tagged with the physician diagnosis results into a convolutional neural network (also referred to as a "ConvNet") as teacher data, and perform supervised learning to acquire the second knowledge. Further, various methods such as unsupervised learning, semi-supervised learning, transductive learning, and multi-task learning may be used.

(9) Further, in the configuration described in claim 8, a configuration may be adopted in which the learning means, while acquiring diagnosis result information indicating a diagnosis result by a physician, based on the one or more first frame images extracted by the first extraction means, and setting the diagnosis result information and the corresponding one or more first frame images as teacher data, acquires the second knowledge by executing at least one of machine learning and data mining and stores the second knowledge in the second storage means.

With this configuration, it is possible to present only frame images extracted as diagnosable frame images among the plurality of frame images included in the captured image to the physician who is the annotator. As a result, the diagnosis support device of the present invention can create teacher data and acquire useful second knowledge while reducing the workload of the physician when acquiring the second knowledge.

(10) Further, in the configuration described in claim 9, a configuration may be adopted in which the first storage means stores, as the first knowledge, a plurality of knowledge for extracting, for each disease that may develop in each tissue constituting the examined eye, the one or more first frame images that can be utilized for diagnosis of the disease, the first extraction means extracts, for each of the diseases, the one or more first frame images that can be utilized for state estimation of the disease, on the basis of the first knowledge, and the learning means, while acquiring the diagnosis result information related to each disease on the basis of the one or more first frame images extracted and corresponding to the disease and setting the diagnosis result information and the corresponding one or more first frame images as teacher data, acquires, for each disease, the second knowledge required for diagnosis of the disease by executing at least one of machine learning and data mining, and stores the second knowledge acquired in association with the corresponding disease in the second storage means.

With this configuration, the diagnosis support device of the present invention can individually extract diagnosable frame images corresponding to each of a plurality of diseases that may develop in the examined eye from a single captured image. Then, by creating teacher data on the basis of the diagnosis results of the physicians based on the extracted diagnosable frame images and executing at least one of machine learning and data mining on the basis of the teacher data, the second knowledge corresponding to each disease can be acquired for each disease and stored in the second storage means by associating the acquired second knowledge with the corresponding disease. As a result, the diagnosis support device of the present invention can acquire second knowledge for diagnosing a plurality of diseases from a single captured image, and can acquire second knowledge corresponding to the plurality of diseases at once on the basis of a small number of sample images. Further, with this configuration, the diagnosis support device of the present invention can extract diagnosable frame images for annotation from the captured images for each disease in advance and present the images to the physician, thereby reducing the workload of the physician when performing annotation.

(11) Further, in the configuration described in any one of claims 1 to 10, a configuration may be adopted in which the first storage means stores, as the first knowledge, a plurality of knowledge for extracting, for each disease that may develop in each tissue constituting the examined eye, the one or more first frame images that can be utilized for state estimation of the disease, the second storage means stores, for each of the diseases, a plurality of knowledge for estimating a state of the disease, as the second knowledge, the first extraction means extracts, for each of the diseases, the one or more first frame images that can be utilized for diagnosis of the disease, on the basis of the first knowledge, the estimation means estimates a state of each disease in the examined eye on the basis of the one or more first frame images extracted for each of the diseases and the second knowledge of the corresponding disease, and the generation means generates information including the state of each of the diseases estimated as the diagnosis support information.

With this configuration, the diagnosis support device of the present invention can extract, for each disease, the diagnosable frame images corresponding to each of a plurality of diseases that may develop in the examined eye from a single captured image. Then, the diagnosis support device of the present invention can estimate, for each disease, the states of a plurality of diseases in the examined eye on the basis of the extracted diagnosable frame images, and generate diagnosis support information including the estimated state for each disease.

As a result, even when a plurality of diseases have developed in the examined eye, the diagnosis support device of the present invention can estimate all disease states that have developed in the examined eye at once on the basis of a single captured image, and generate and make diagnosis support information including such estimation results available, thereby dramatically improving user convenience.

(12) Further, in the configuration described in any one of claims 1 to 11, a configuration may be adopted in which the diagnosis support device of the present invention further comprises labeling means for labeling a tissue name corresponding to a tissue of the examined eye in focus in each of the frame images included in the captured image, and second extraction means for extracting, as a second frame image, the frame image having a largest area of a pixel region reflecting tissue in focus in each of the frame images labeled, and the generation means generates the diagnosis support information including the second frame image extracted.

With this configuration, the diagnosis support device of the present invention can apply labeling to the tissue in focus in the frame images included in the captured image to make the tissue reflected in each frame image identifiable, and extract the frame image having the largest area of a pixel region reflecting the tissue in focus in the captured image to generate and make diagnosis support information including the extracted frame image available. Usually, the frame image most largely reflecting the tissue with the developing disease is often an image from which the state of the disease can be most intuitively understood, and thus the above-described configuration makes it possible to generate and make diagnosis support information including a best shot frame image available, as a graphical user interface (GUI), from which the patient can most intuitively understand the state of the disease, thereby dramatically improving the user experience (UX) of the patient.

(13) Further, in the configuration described in any one of claims 1 to 12, a configuration may be adopted in which the diagnosis support device of the present invention further comprises three-dimensional image construction means for constructing a three-dimensional image of the examined eye by layering, in correspondence with a focal length, each frame image included in the captured moving image acquired, the second storage means storing, as the second knowledge, on the basis of the three-dimensional image, knowledge for estimating at least one of (i) the health state of the examined eye, and (ii) the one or more information parameter values, and the estimation means estimating on the basis of the three-dimensional image generated and the second knowledge, at least one of (i) the health state of the examined eye, and (ii) the one or more information parameter values.

The moving image captured by the mobile communication terminal device includes a plurality of frame images having different focal lengths, and thus, by layering the frame images in an order corresponding to the focal length of each frame image, it is possible to construct a three-dimensional image of the examined eye and utilize the three-dimensional image for estimation of the health state or present the three-dimensional image to the user. Further, a three-dimensional image includes more information than a plane image, and thus the above-described configuration makes it possible to improve the accuracy of estimating the health state and the information parameter values of the examined eye and improve the reliability of the diagnosis support information.

Effect of the Invention

According to the present invention, it is possible to reliably generate and make diagnosis support information related to an examined eye available, even in regions where equipment, physicians, and the like are in short supply.

BRIEF DESCRIPTION OF THE DRAWINGS

FIG. 18A is a graph showing results obtained by measuring a relationship between age (weeks old) and tear secretion (TS) volume of mice, and FIG. 18B is a table showing progress of continuing tear secretion (TS) by group.

FIG. 19A is a graph showing results obtained by measuring a relationship between age (weeks old) and tear film break-up time (TFBUT) of mice, and FIG. 19B is a table showing progress of TFBUT by group.

FIG. 20 shows photographs of continuous tear films stained with a fluorescein solution, the upper row being examples of a graft-versus-host disease (GVHD) group in which the tear film is broken in three seconds, and the lower row being examples of a normal group in which the tear film is stabilized in three seconds and collapsed in six seconds.

FIG. 21A is a graph showing results obtained by measuring a relationship between age (weeks old) and continuous corneal fluorescein score (CFS) of mice, and FIG. 21B is a table showing progress of CFS by group.

FIGS. 22A to 22C show results of comparing measurement results of the TFBUTs and CFSs of the smart eye camera of the first embodiment and the existing device, FIG. 22A being a graph of TFBUT, FIG. 22B being a graph of CFS, and FIG. 22C being a table summarizing these.

FIGS. 23A and 23B are graphs showing a correlation between diagnosis results of the smart eye camera of the first embodiment and the existing device, FIG. 23A being a graph of TFBUT and FIG. 23B being a graph of CFS.

EMBODIMENTS OF THE INVENTION

Hereinafter, embodiments of the present invention will be described with reference to the drawings. It should be noted that the following embodiments are embodiments in which a diagnosis support device, a diagnosis support system, and a program according to the present invention are applied to a system for realizing a function of estimating a health state of an examined eye on the basis of a captured moving image of the examined eye, generating diagnosis support information including the estimation results, and making such information available to the user. However, the embodiments described below do not unduly limit the contents of the present invention described in the claims, and not all configurations described in the embodiments are configuration requirements essential to the present invention.

[A] First Embodiment

[A1] Configuration and Overview of Diagnosis Support System

Figure 1:
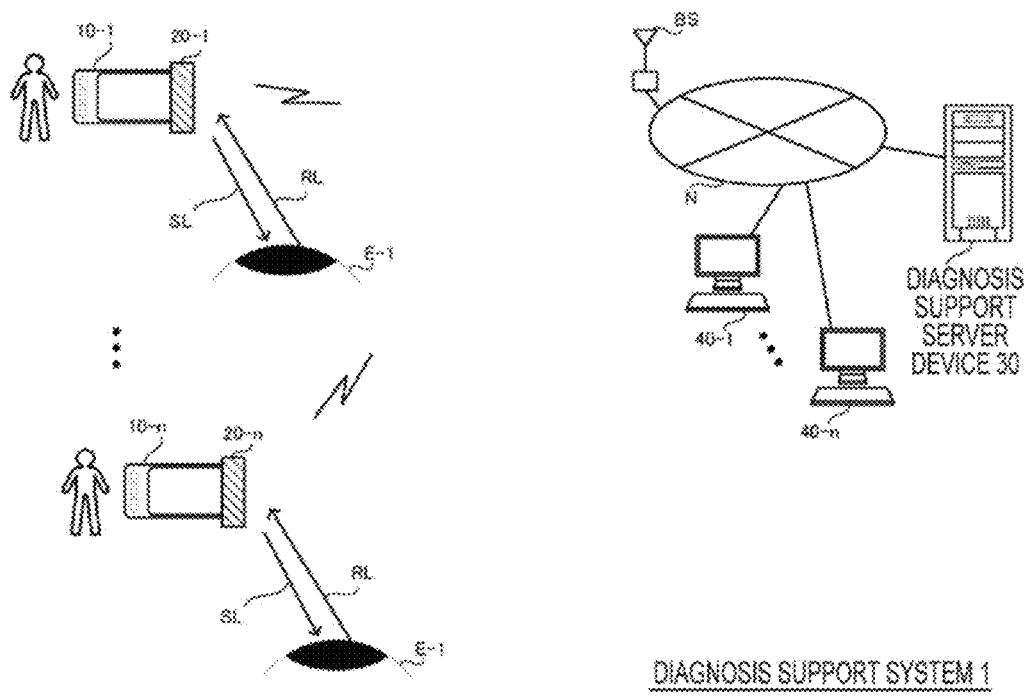
FIG. 1 is a system configuration diagram illustrating a configuration example of a first embodiment of a diagnosis support system according to the present invention.

First, a configuration and provide an overview of a diagnosis support system 1 of a first embodiment in the present invention will be described with reference to FIG. 1. It should be noted that FIG. 1 is a system configuration diagram illustrating a configuration example of the diagnosis support system 1 of this embodiment. Further, in FIG. 1, to prevent the drawing from becoming complex, only some users are illustrated, and only some mobile communication terminal devices 10 equipped with a close-up imaging device 20 (that is, smart eye cameras) and some annotation terminal devices 40, which constitute the diagnosis support system 1, are illustrated. That is, in the diagnosis support system 1, there are more users and more mobile communication terminal devices 10 equipped with the close-up imaging device 20 and annotation terminal devices 40 than those illustrated in the drawing.

As illustrated in FIG. 1, the diagnosis support system 1 of this embodiment (a) includes a plurality of mobile communication terminal devices 10-1 to 10-*n* (hereinafter referred to as "mobile communication terminal device 10") carried by each user and functioning as a smart eye camera with the close-up imaging device 20 mounted thereto, a diagnosis support server device 30 that is communicatively connected to each mobile communication terminal device 10 via a network N and executes processing based on moving image data transmitted (uploaded) from each mobile communication terminal device 10, and a plurality of annotation terminal devices 40-1 to 40-*n* (hereinafter referred to as "annotation terminal device 40") used by annotators such as ophthalmologists, and is a system for supporting diagnosis of an examined eye E by, in the diagnosis support server device 30, (1) estimating a health state (presence or absence of disease, severity thereof, and the like) of the examined eye E on the basis of the moving image data uploaded from the mobile communication terminal device 10, (2) generating diagnosis support information on the basis of the estimation results, and (3) distributing the generated diagnosis support information to the corresponding mobile communication terminal device 10. It should be noted that the format and content of the diagnosis support information is as desired and, for example, a configuration may be adopted in which information such as a name of suspected disease, a severity of disease, a treatment method, and necessity of surgery is described in extensible markup language (XML) or another format, and displayed on the mobile communication terminal device 10. Further, the health state of the examined eye E estimated by the diagnosis support server device 30 is as desired and, for example, the presence or absence of specific diseases and the states of various diseases that may develop in various tissues of the examined eye E (eyelid, eye surface, cornea, conjunctiva, iris, anterior chamber, lens, fundus tissue, or the like, for example) can be estimated. However, for the sake of specificity of explanation, a system that estimates the state of nuclear sclerosis (cataracts) in the examined eye E (that is, presence or absence of cataracts and severity thereof) will be described in this embodiment, and methods of estimating states of other diseases will be described in detail in modifications and a second embodiment. It should be noted that the diagnosis support system 1 of this embodiment may be configured not to estimate the severity of cataracts in the examined eye E, but only to estimate the presence or absence of the onset of the disease.

Here, cataract diagnostic images must be captured by a physician or the like having expert knowledge by using an expensive ophthalmic slit lamp microscope installed in an eye clinic. For this reason, in regions such as developing countries where equipment, physicians, and the like are in short supply, a diagnostic image cannot be captured, making it difficult to estimate the health state of the examined eye E and generate diagnosis support information by using a conventional ophthalmic system.

Therefore, in the diagnosis support system 1 of this embodiment, a method is adopted in which the close-up imaging device 20 is mounted onto the mobile communication terminal device 10, and a camera module built into the mobile communication terminal device 10 is used to capture a moving image of the examined eye E. The close-up imaging device 20 includes at least a slit light forming member 61 that generates slit light SL as observation light on the basis of light-source light emitted from a light source 92 (described below) built into the mobile communication terminal device 10, and a convex lens member 93 that condenses light including, of the slit light SL, reflected light RL of lens tissue of the examined eye E onto an imaging camera lens 91 (described below) of the mobile communication terminal device 10. Then, on the basis of the moving image captured by the mobile communication terminal device 10, the diagnosis support server device 30 estimates the state of cataracts in the examined eye E and generates diagnosis support information on the basis of the estimation results. It should be noted that a configuration and a principle of the close-up imaging device 20 will be described in detail below. Further, in many cases, the mobile communication terminal device 10 is provided with a plurality of camera modules (for example, two modules of an in-camera module provided on a display unit side and an out-camera module provided on a back surface side, or the like). However, usually the out-camera module tends to have higher resolution and be equipped with better functioning optics. For this reason, in this embodiment, a configuration is adopted in which a close-up imaging device for an out-camera module is used as the close-up imaging device 20, improving the resolution when capturing a moving image of the examined eye E and improving accuracy when estimating the state of cataracts. That is, when referencing the light source 92 and the imaging camera lens 91 in this embodiment, description will be made presuming provision on the out-camera module side of the mobile communication terminal device 10. However, the present invention is not limited to a configuration that utilizes an out-camera module, and adoption of a configuration that utilizes an in-camera module is also possible.

The camera module mounted onto the mobile communication terminal device 10 can be easily operated even by users who do not have specialized knowledge. Further, with the close-up imaging device 20 mounted onto the mobile communication terminal device 10, it is possible to, while generating the slit light SL on the basis of light-source light emitted from the light source 92 of the mobile communication terminal device 10, irradiate lens tissue of the examined eye E with the slit light SL as observation light, condense the light including, of the slit light SL, the reflected light RL of the lens tissue onto the imaging camera lens 91 (described below) of the camera module, and easily capture a moving image including one or more diagnosable frame images.

On the other hand, in a case in which a user other than a physician or the like captures an image of the examined eye E, the user is not familiar with capturing an image of the examined eye E, and therefore there is a high possibility that the user will capture a moving image including many miscellaneous frame images (that is, frame images that cannot be utilized for diagnosis) that do not satisfy the conditions of a diagnosable frame image that can be utilized for the diagnosis of cataracts, such as (a) frame images without the tissue to be observed (that is, lens tissue) in focus, (b) frame images not reflecting the lens tissue, and (c) images not reflecting the examined eye E itself in the first place, for example. Further, even when a physician or the like captures an image of the examined eye E, there is a possibility that a moving image including frame images that cannot be utilized for the diagnosis of cataracts will be captured during the first few seconds after the start of capturing the moving image. This makes it difficult to estimate the state of cataracts by using a moving image captured with a smart eye camera as is. Therefore, in this embodiment, a method is adopted in which the diagnosis support server device 30 extracts, from among all frame images constituting the moving image data uploaded from the mobile communication terminal device 10, diagnosable frame images that can be utilized to diagnose the state of cataracts in the examined eye E, and estimates the state of cataracts in the examined eye E on the basis of the diagnosable frame images.

Here, to diagnose the severity of cataracts, it is necessary to use an image that satisfies three conditions: (Condition 1) The lens tissue of the examined eye E is irradiated with the slit light SL as the observation light, (Condition 2) at least a portion of the lens tissue is reflected along with, of the irradiated slit light SL, the reflected light RL of the lens tissue, and (Condition 3) the lens tissue is in focus. For this reason, the diagnosis support server device 30 is configured to extract, from among all frame images that constitute the moving image captured by the mobile communication terminal device 10, frame images that satisfy these three conditions as diagnosable frame images. Then, the diagnosis support server device 30 estimates the state of cataracts in the examined eye E on the basis of the extracted diagnosable frame images, and generates diagnosis support information. It should be noted that the diagnosis support server device 30 of this embodiment constitutes the "diagnosis support device" of the present invention, for example.

With this configuration, the diagnosis support system 1 of this embodiment can capture a moving image including a diagnosable frame image for cataract diagnosis in the examined eye E and appropriately estimate the state of cataracts on the basis of the captured moving image, even when the user does not have expert medical knowledge. As a result, the diagnosis support system 1 of this embodiment can reliably generate and make diagnosis support information related to the examined eye E available, even in regions where physicians and the like are in short supply. Further, the close-up imaging device 20 mounted onto the mobile communication terminal device 10 need only include at least the slit light forming member 61 and the convex lens member 93, and thus can be manufactured at a very low cost. As a result, the diagnosis support system 1 of this embodiment can capture a moving image including a diagnosable frame image and generate diagnosis support information at low cost, without using an expensive ophthalmic slit lamp microscope.

[A2] Schematic Configuration of Diagnosis Support System 1

The mobile communication terminal device 10 is, for example, a portable communication terminal device carried by the user, such as a smartphone, a tablet-type information communication terminal device, or a cell phone, and includes a display unit (not illustrated) constituted by a display element such as a liquid crystal panel or an organic electroluminescent (EL) panel, a speaker, and an operation unit constituted by a touch panel provided on the display unit and a numeric keypad or the like. Further, the mobile communication terminal device 10 includes a camera module including the imaging camera lens 91, and the light source 92 constituted by a light-emitting element such as a white light-emitting diode (LED).

In addition to the imaging camera lens 91, the camera module has a diaphragm mechanism for narrowing light transmitted through the imaging camera lens 91, a shutter mechanism, an auto-focus mechanism, a shake correction mechanism, and other optical systems not illustrated. Further, the camera module includes image sensors such as a charge coupled device (CCD) image sensor or a complementary metal oxide semiconductor (CMOS) image sensor that receives light transmitted through the imaging camera lens 91 and outputs a signal corresponding to the light received, and the signal output by the image sensor is supplied to an image generating unit (not illustrated) constituted by a central processing unit (CPU), thereby generating the moving image data on the basis of the light transmitted through the imaging camera lens 91. It should be noted that the method of generating the moving image data in the image generating unit is as desired. For example, the moving image data may be generated by generating bitmap data for each frame image and then arranging the generated bitmap data in chronological order, or the moving image data may be generated in a format compressed by an inter-frame predictive coding method, such as the moving picture experts group (MPEG) 2, and H.264 and H.265. This camera module and image generating unit adjust the optical system on the basis of user input operations made to the operation unit in linkage with the display unit and the operation unit. Then, the frame image reflecting the subject (examined eye E in this embodiment) is generated on the basis of the light received by the image sensor, and the image being captured is displayed on the display unit on the basis of the generated frame image data. It should be noted that a camera module equipped with an auto-focus mechanism and mounted onto the mobile communication terminal device 10 is the same as a camera module used in conventional smartphones and other devices.

Furthermore, the mobile communication terminal device 10 is provided with an application program (hereinafter referred to as "diagnostic app") for acquiring, on the basis of the captured moving image of the examined eye E, the diagnosis support information from the diagnosis support server device 30, and displaying the information. Then, by executing this diagnostic app, the mobile communication terminal device 10 uploads the moving image data generated by the camera module and the image generating unit to the diagnosis support server device 30, thereby acquiring the diagnosis support information from the diagnosis support server device 30. The mobile communication terminal device 10 then displays information related to the presence or absence of cataracts and the severity thereof (specifically, NS grade or other index that expresses the severity of cataracts by a numerical value of 1 to 5) in the examined eye E, and information such as the treatment method and necessity of surgery, on the display unit, on the basis of the diagnosis support thus acquired. It should be noted that, in a case in which the diagnosis support information is generated in XML format, an existing browser application can also be used in place of the diagnostic app.

The close-up imaging device 20 is an optical equipment detachably mounted onto the mobile communication terminal device 10, and includes the slit light forming member 61 that generates the slit light SL on the basis of the light irradiated from at least the light source 92 of the mobile communication terminal device 10, and the convex lens member 93 that condenses the light including, of the slit light SL, the reflected light RL of the examined eye E on the imaging camera lens 91. Then, the close-up imaging device 20 generates the slit light SL as observation light on the basis of light-source light (white diffused light) emitted from the light source 92, and condenses the light including, of the slit light SL, the reflected light RL of the examined eye E on the imaging camera lens 91. The mobile communication terminal device 10 captures a moving image of the examined eye E, including a diagnosable frame image, on the basis of the light condensed on the imaging camera lens 91 by the function of this close-up imaging device 20. As a result, the mobile communication terminal device 10 equipped with the close-up imaging device 20 (that is, smart eye camera), as a whole, realizes the same functions as an existing ophthalmic slit lamp microscope.

The diagnosis support server device 30 is a computer system provided on the network N and extracts diagnosable frames included in the moving image data uploaded from the mobile communication terminal device 10 on the basis of knowledge for extracting diagnosable frame images (hereinafter referred to as "extracting knowledge") acquired by machine learning or data mining. It should be noted that the extracting knowledge in this embodiment corresponds to the "first knowledge" of the present invention, for example. Further, the specific method of acquiring the extracting knowledge is as desired. However, the determination of whether or not each frame image included in the moving image data corresponds to a diagnosable frame image, unlike the diagnosis of cataracts, can be made only by whether or not the above-described conditions 1 to 3 are satisfied. For this reason, it is possible to determine whether or not an image corresponds to a diagnosable frame image even by non-ophthalmologists. Accordingly, for example, when an arbitrary person use the annotation terminal device 40, the system may be configured to extract diagnosable frame images for cataracts from the moving image data uploaded from the mobile communication terminal device 10 and, while setting the extracted frame images as teacher data, acquire the extracting knowledge by executing at least one of machine learning and data mining in the diagnosis support server device 30.

Further, the diagnosis support server device 30 of this embodiment includes diagnostic knowledge for estimating the state of cataracts in the examined eye E on the basis of the diagnosable frames extracted from the moving image data on the basis of the extracting knowledge. Then, the diagnosis support server device 30 estimates the presence or absence of cataracts, an index indicating the severity of cataracts such as NS grade, the treatment method, the necessity of surgery, and the like in the examined eye E on the basis of the diagnosable frame images extracted from the moving image data and the diagnostic knowledge, generates diagnosis support information including the estimation results, and distributes the information to the mobile communication terminal device 10 from which the moving image data was uploaded. It should be noted that the diagnostic knowledge in this embodiment corresponds to the "second knowledge" of the present invention, for example. Further, the method of causing the diagnosis support server device 30 to acquire the diagnostic knowledge is as desired. For example, a configuration may be adopted in which a computer for managing electronic medical records installed in an eye care facility (not illustrated) is connected to the diagnosis support server device 30 directly or via the network N, diagnosis results of patients visiting the eye care facility and ophthalmic diagnostic images captured at the eye care facility are acquired from the electronic medical records of the eye care facility, and at least one of machine learning and data mining is executed while using the acquired data as teacher data to acquire the diagnostic knowledge. However, in a case in which this method is used, the computer for managing electronic medical records at the eye care facility must be equipped with special functions. Further, in this case, the need arises to communicably connect the diagnosis support server device 30 with the computer for managing electronic medical records at the eye care facility, and to manage the data acquired from each management computer in the diagnosis support server device 30, making it difficult to reduce initial costs at the time of system construction. Furthermore, in this case, with utilization of the electronic medical record information, it is necessary for the eye care facility to obtain the consent of patients in advance and to strictly manage personal information, making it difficult to reduce the running costs during system operation.

Therefore, the diagnosis support system 1 of this embodiment generally acquires the diagnostic knowledge by the method below. (Step 1) First, whenever moving image data captured by the mobile communication terminal device 10 is uploaded from the mobile communication terminal device 10, the diagnosis support server device 30 extracts diagnosable frame images from the moving image data, transmits the diagnosable frame images to the annotation terminal device 40, and displays the diagnosable frame images on the annotation terminal device 40. (Step 2) Three physicians who are annotators each make a diagnosis regarding the presence or absence of cataracts, the severity thereof (NS grade or other index), the treatment method, the necessity of surgery, and the like on the basis of the diagnosable frame images displayed on the annotation terminal device 40, and input the diagnosis results into the annotation terminal device 40. (Step 3) The annotation terminal device 40 generates diagnosis result information indicating the diagnosis result on the basis of the input of the physicians, creates teacher data corresponding to each diagnosable frame image by tagging the corresponding diagnosable frame image with the diagnosis result information, and transmits the data to the diagnosis support server device 30. (Step 4) The diagnosis support server device 30 accumulates the teacher data (that is, tagged diagnosable frame images) acquired from the annotation terminal device 40 each time. Then, when the quantity of accumulated teacher data becomes greater than or equal to a number of samples a (hereinafter simply referred to as "a") required for acquisition of diagnostic knowledge, the diagnosis support server device 30 executes at least one of machine learning and data mining by using the accumulated teacher data to acquire the diagnostic knowledge.

By adopting this method, a physician who is the annotator need not perform the task of finding diagnosable frame images in the moving image data, and need only make a diagnosis of cataracts on the basis of the diagnosable frame images extracted by the diagnosis support server device 30, and thus it is possible to reduce the workload of the physician during diagnostic knowledge acquisition. Further, because the moving image data uploaded from the mobile communication terminal device 10 does not need to include patient-identifiable information, the cost for personal information protection can be reduced according to this method. Furthermore, at least one annotation terminal device 40 need only be prepared, making it possible to construct the system at low cost. It should be noted that, in addition to knowledge acquired from the diagnosis results of the physicians based on the diagnosable frame images extracted from the moving image data, the diagnostic knowledge may be configured to include, for example, knowledge described in medical books, medical encyclopedias, and other literature, or medical knowledge disclosed on the Internet. In this case, a configuration can also be adopted in which the treatment method and the necessity of surgery are estimated from knowledge in medical books and the like in correspondence with the estimated NS grade of the cataracts and other factors.

Then, when the diagnosis support information is distributed from the diagnosis support server device 30, information such as the presence or absence of cataracts, the index such as the NS grade, the treatment method, and the necessity of surgery in the examined eye E is displayed on the display unit on the basis of the diagnosis support information in the mobile communication terminal device 10, and is viewable by the user.

The annotation terminal device 40 is, for example, a computer such as a personal computer (PC) or tablet-type information communication terminal device, includes a display unit (not illustrated), a touch panel provided on the display unit, and an operation unit composed of a mouse, a keyboard, and the like, and is communicably connected to the diagnosis support server device 30 directly or via the network N.

This annotation terminal device 40 displays the diagnosable frame images extracted by the diagnosis support server device 30. Further, the annotation terminal device 40 displays a graphic user interface (GUI) for the physician, who is the annotator, to input diagnosis results based on the diagnosable frame images and, when the physician inputs the diagnosis results, generates diagnosis result information corresponding to the input diagnosis results. Then, the annotation terminal device 40 creates teacher data by tagging the corresponding diagnosable frame image with the diagnosis result information, and transmits the data to the diagnosis support server device 30. It should be noted that the number of the annotation terminal devices 40 is as desired, and may be a number equivalent to the number of annotators (physicians during diagnostic knowledge acquisition and arbitrary persons during extracting knowledge acquisition), or one annotation terminal device 40 may be used by a plurality of annotators.

[A3] Configuration of Close-Up Imaging Device 20

Next, a configuration of the close-up imaging device 20 of this embodiment will be described with reference to FIGS. 2 to 7. It should be noted that FIGS. 2 to 7 are drawings illustrating a configuration of a close-up imaging device 20A of this embodiment. As illustrated in FIG. 2 to FIG. 7, the close-up imaging device 20A of this embodiment has a configuration that is detachably mounted to the mobile communication terminal device 10 and includes a housing 80 having a rectangular parallelepiped outer shape.

Figure 2:
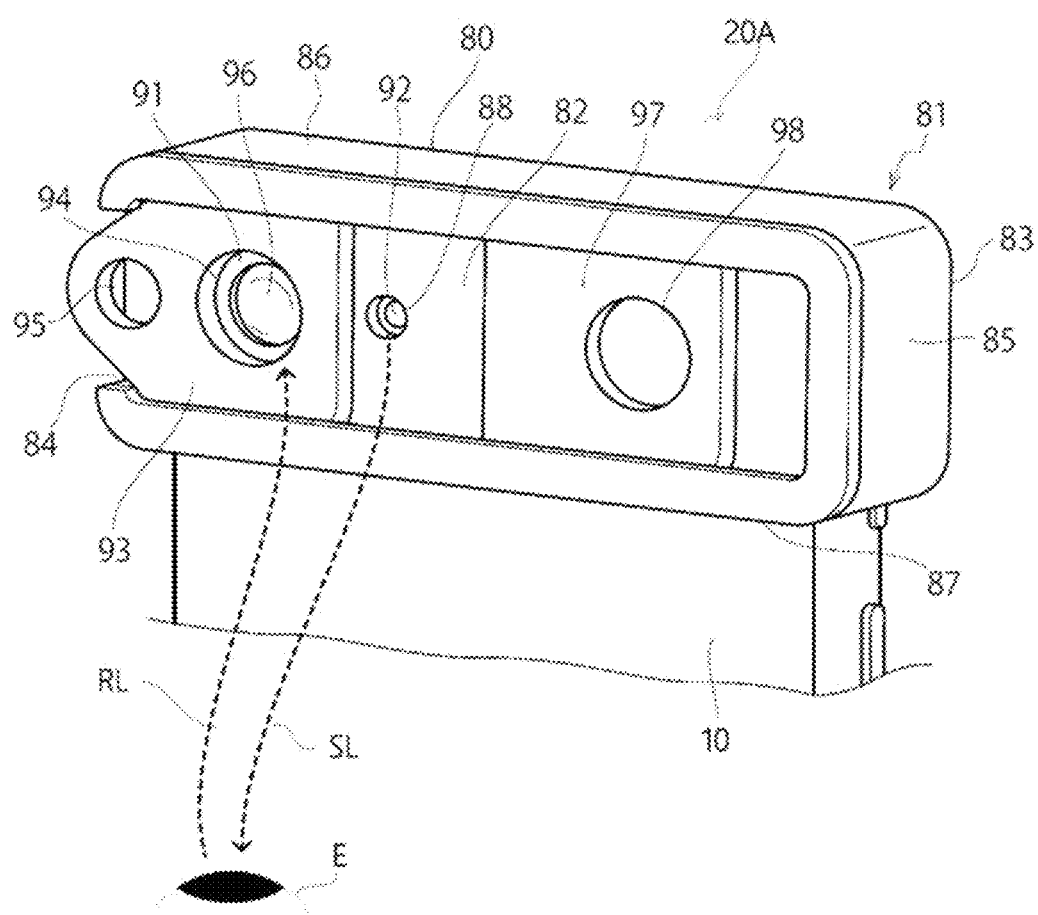
FIG. 2 is a perspective view illustrating a close-up imaging device of the first embodiment.
Figure 4:
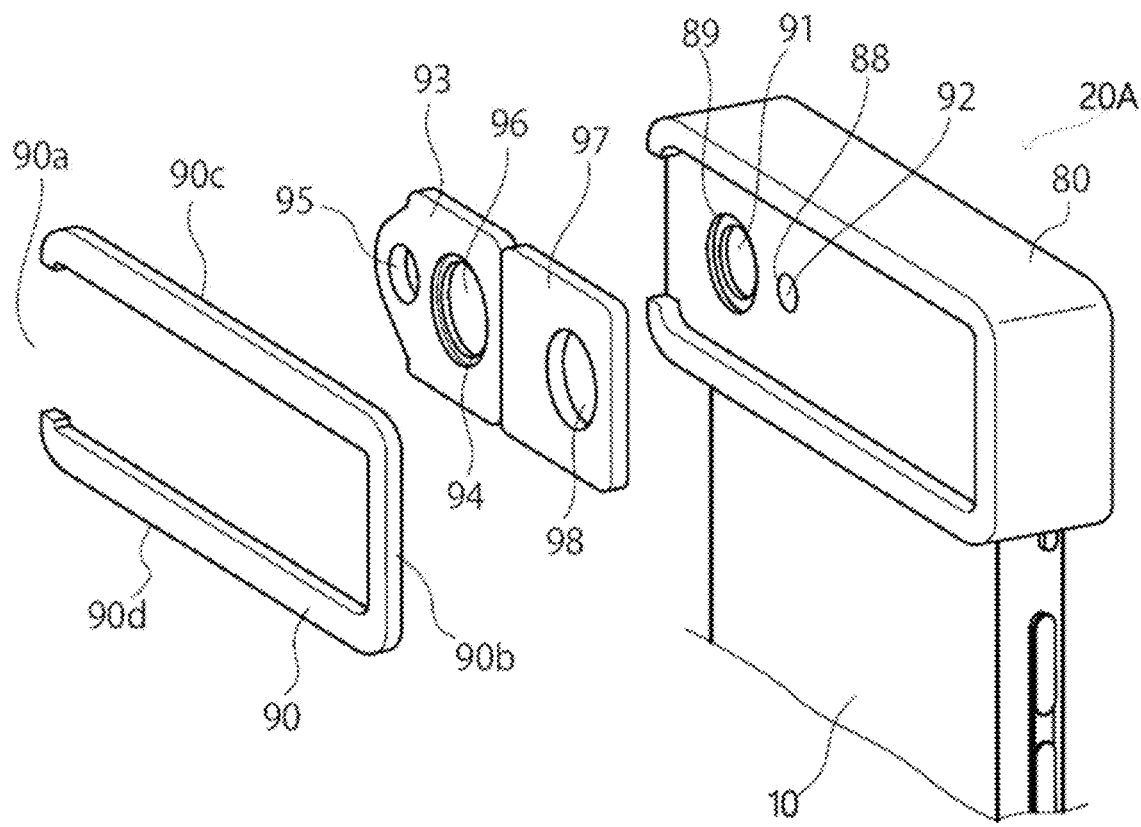
FIG. 4 is an exploded configuration view of the close-up imaging device illustrated in FIG. 2.

This housing 80 has a hollow interior and, as illustrated in FIGS. 2 and 4, is constituted by an outer wall part 81 and a front surface plate 90. The outer wall part 81 includes a front wall 82, a back wall 83, a left-side wall 84, a right-side wall 85, an upper wall 86, and a lower wall 87. An opening (not illustrated) in which the mobile communication terminal device 10 is inserted is formed in the lower wall 87. The opening is constituted by a through-hole formed in a left-right direction from the left-side wall 84 side to the right-side wall 85 side. The opening is configured so that an upper end portion of the mobile communication terminal device 10 provided with an out-camera module is inserted therethrough, with an opening width in a front-rear direction slightly wider than a thickness of the mobile communication terminal device 10, and an opening width in the left-right direction slightly wider than a width of the mobile communication terminal device 10. It should be noted that a front direction is defined as a direction from the back wall 83 to the front wall 82, and a direction opposite thereto is defined as a rear direction. Further, a left direction is defined as a direction from the right-side wall 85 to the left-side wall 84, and a direction opposite thereto is defined as a right direction. Furthermore, an upper direction is defined as a direction from the lower wall 87 to the upper wall 86, and a direction opposite thereto is defined as a lower direction.

The front wall 82 includes a peripheral edge part in which an upper edge, a lower edge, and a right edge protrude in a frame shape in the front direction. The front surface plate 90 having a width wider than a width of the peripheral edge part is mounted to the peripheral edge part. The front surface plate 90 is a frame-like body with a central portion opened, constituted by an opened left edge part 90a, a right edge part 90b, an upper edge part 90c, and a lower edge part 90d. The width of the front surface plate 90 is wider than that of the peripheral edge part of the front wall 82. For this reason, the front surface plate 90 is provided so as to project inside the peripheral edge part. The projecting portion functions as upper and lower rails, and a color filter member 97 having a plate shape and the convex lens member 93 having a plate shape are slidably fitted into the upper and lower rails. The gap between the front wall 82 and the projecting portion of the front surface plate 90 is formed slightly larger than thicknesses of the color filter member 97 having a plate shape and the convex lens member 93 having a plate shape, at slidable dimensions. It should be noted that, the opening is the left edge part 90a in the example in FIG. 2, but may be the right edge part 90b.

The front wall 82 is provided with two holes. One hole 89 is provided in a position corresponding to the imaging camera lens 91 of the mobile communication terminal device 10, and the other hole 88 is provided in a position corresponding to the light source 92 of the mobile communication terminal device 10. With these two holes 88, 89, it is possible to emit light-source light emitted from the light source 92 of the mobile communication terminal device 10 in the front direction, and receive return light (light including the reflected light RL of the slit light SL, for example) by the imaging camera lens 91 of the mobile communication terminal device 10 to capture an image of the anterior eye or the eye ground of the examined eye E.

(Color Filter Member)

The color filter member 97 is detachably provided above the light source 92. This color filter member 97 is a plate-shaped member, and is attached and detached above the light source 92 by sliding the color filter member 97 as exemplified in FIGS. 3A to 3C described below. This color filter member 97 is preferably a blue filter that turns white light emitted from the light source 92 of the mobile communication terminal device 10 into blue light. For example, a blue filter that converts white light into blue light having a wavelength of 488 nm is preferred. The blue filter adopted may be a colored acrylic resin.

A hole 98 provided in the color filter member 97 is a hole in which a finger is hooked when sliding the color filter member 97. This may not necessarily be a hole as long as a finger can be hooked onto it to slide the color filter member 97, and may be a protrusion.

The light source 92 can be covered and uncovered by sliding the color filter member 97 in the left-right direction. That is, the color filter member 97 is attached and detached from above the light source 92 or the convex lens member 93 is attached and detached from above the imaging camera lens 91 by sliding the color filter member 97 and the convex lens member 93. In this embodiment, with the color filter member 97 removed from the light source 92, the examined eye E is irradiated with white diffused light serving as the light-source light, emitted from the light source 92 and passing through the hole 88 as is, as the observation light, and light including the reflected light RL thereof is received by the image sensor through the imaging camera lens 91, making it possible to observe and capture the eyelid, the eye surface, the cornea, and the conjunctiva of the examined eye E. Further, an injury that occurred on the cornea and the conjunctiva can be observed and captured by covering the light source 92 with the color filter member 97. For example, with administration of fluorescein solution as a contrast medium to the eye and adoption of a blue free filter for vital staining examination as the color filter member 97, the light-source light is changed into blue light, the examined eye E is irradiated with the blue light as the observation light, a color of the injury that occurred on the cornea or the conjunctiva is changed to green, and the green light is condensed on the imaging camera lens 91 by the convex lens member 93 to receive the condensed green light by the image sensor, making it possible to observe and capture an image of an injury that occurred on the cornea or the conjunctiva of the examined eye E. It should be noted that the method of estimating the state of disease in the cornea and the conjunctiva of the examined eye E by utilizing blue light and the estimation of the state of anterior eye disease using white diffused light are described in detail in the modifications section.

(Convex Lens Member)

The convex lens member 93 is detachably provided above the imaging camera lens 91. This convex lens member 93 is a plate-shaped member, and is attached and detached above the imaging camera lens 91 by being slid as exemplified in FIGS. 3A to 3C. This convex lens member 93 includes a convex lens 96 that condenses light on the imaging camera lens 91 of the mobile communication terminal device 10. The convex lens 96 is selected as desired in consideration of focal length. The convex lens 96 is mounted in a hole 94 provided in the convex lens member 93. The convex lens 96 brings the tissue to be observed in the examined eye E into focus and corrects blurring of the image, making it possible to clearly observe and capture the tissue to be observed in the examined eye E.

A hole 95 provided in the convex lens member 93 is a hole in which a finger is hooked when sliding the convex lens member 93 and, with the convex lens member 93 slid to dispose the hole 95 above the light source 92 (refer to FIG. 3C), acts to improve a directivity of the light emitted from the light source 92 as well.

Figure 3A:
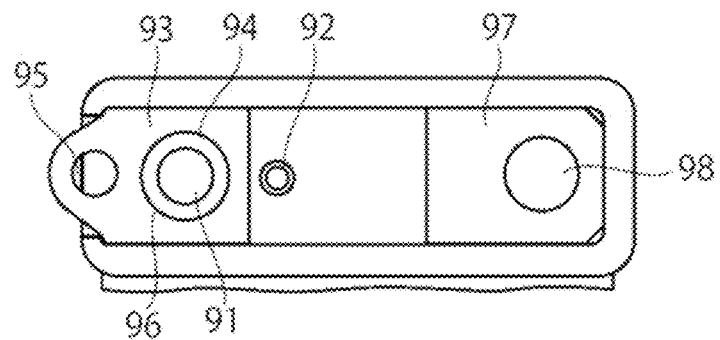
FIGS. 3A to 3C are explanatory views illustrating form examples in which a convex lens member and a color filter member are slid in the close-up imaging device of the first embodiment.
Figure 3B:
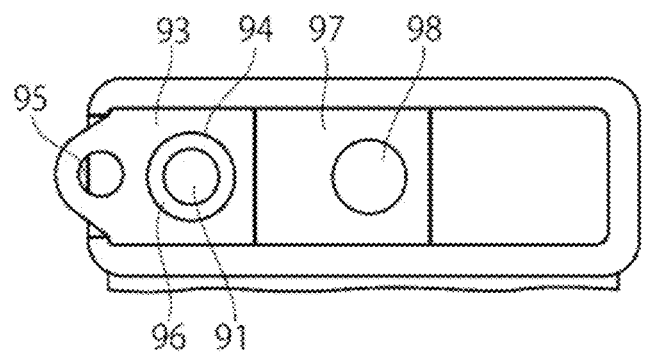
Figure 3C:
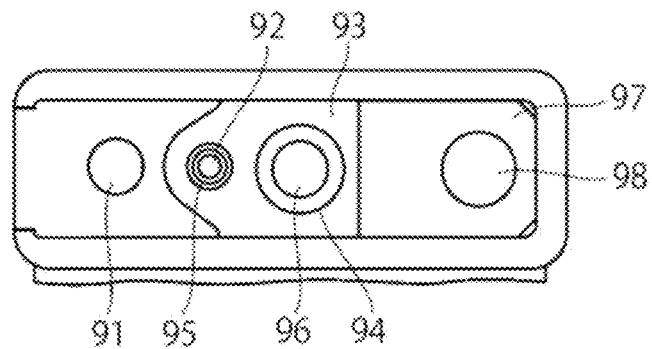

FIGS. 3A to 3C illustrate forms in which the color filter member 97 and the convex lens member 93 are slid. FIG. 3A is a form in which the convex lens 96 of the convex lens member 93 is mounted above the imaging camera lens 91, and the color filter member 97 is slid in the right direction and removed from above the light source 92. FIG. 3B is a form in which the convex lens 96 of the convex lens member 93 is mounted above the imaging camera lens 91, and the color filter member 97 is slid in the left direction and mounted above the light source 92. FIG. 3C is a form in which the color filter member 97 is slid in the right direction and removed from above the light source 92, and the convex lens 96 of the convex lens member 93 is removed from above the imaging camera lens 91. It should be noted that, in this FIG. 3C, the hole 95 of the convex lens member 93 is disposed above the light source 92, and thus white diffused light serving as the light-source light, emitted from the light source 92 is adjusted in directivity when passing through the holes 88, 95, and is irradiated in the front direction as the observation light.

(Slit Light Forming Member)

Figure 5:
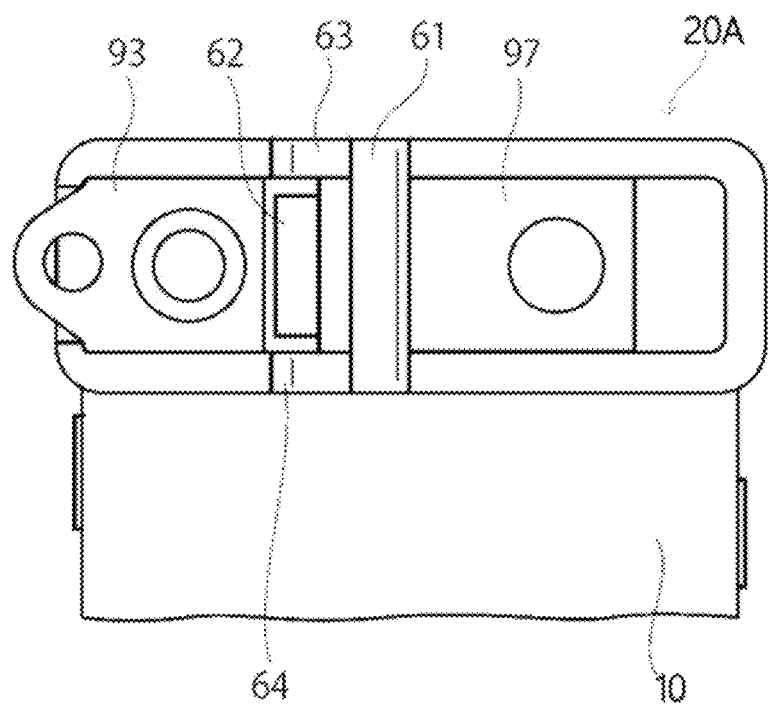
FIG. 5 is a front view illustrating a form in which a slit light forming member is attached to the close-up imaging device illustrated in FIG. 2.
Figure 6:
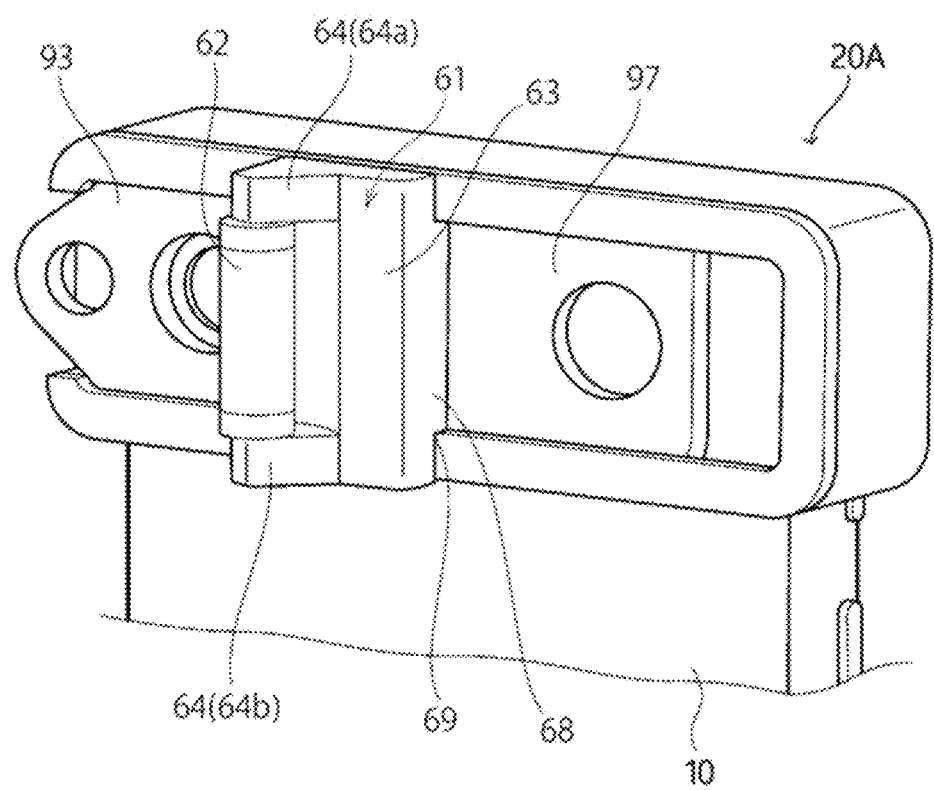
FIG. 6 is a perspective view of the form illustrated in FIG. 5.
Figure 7:
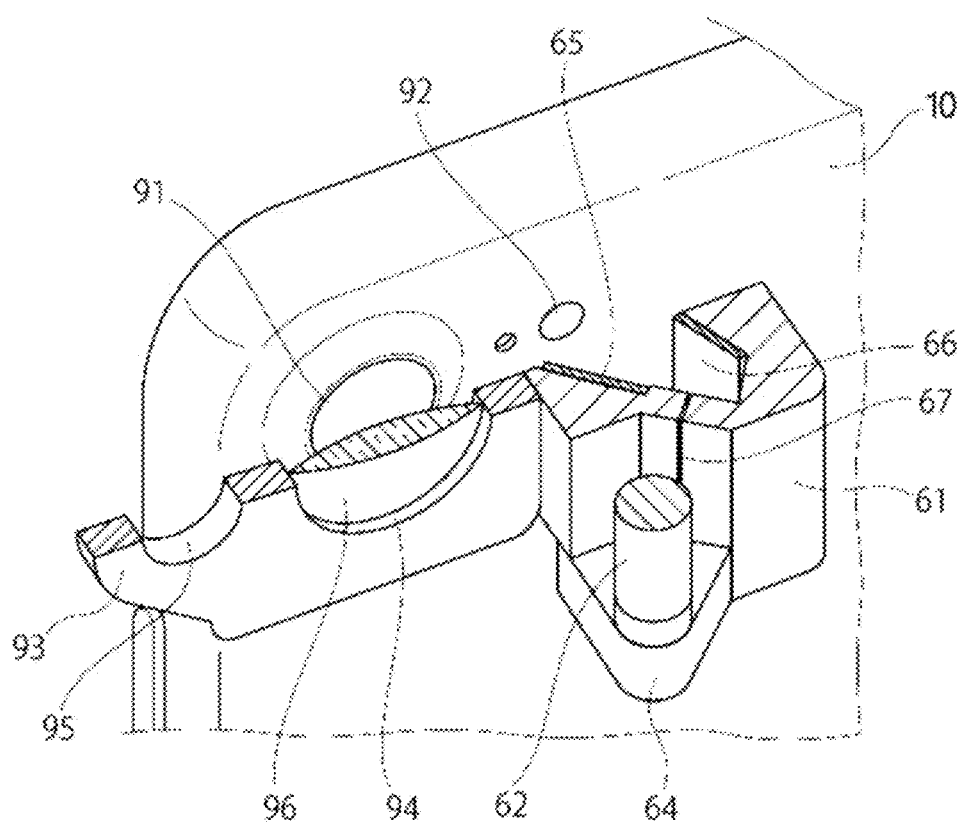
FIG. 7 is an explanatory view of the form illustrated in FIG. 5.

The slit light forming member 61, as illustrated in FIG. 5 to FIG. 7, is a member that forms the white diffused light serving as the light-source light, emitted from the light source 92 of the mobile communication terminal device 10 into the slit light SL by a cylindrical lens 62. Means for attaching/detaching the slit light forming member 61 is not particularly limited, but preferably the slit light forming member 61 is detachably provided on the upper and lower rails on which the color filter member 97 and the convex lens member 93 are slid. It should be noted that, for example, the slit light forming member 61, the color filter member 97, and the holes 88, 95 of this embodiment constitute the "observation light irradiating member" of the present invention.

With such a slit light forming member 61, the examined eye E is irradiated with the slit light SL formed by the cylindrical lens 62, and the light including the reflected light RL thereof is concentrated by the convex lens member 93 on the imaging camera lens 91 of the mobile communication terminal device 10 to capture an image of the examined eye E, making it possible to observe and capture in detail the anterior eye of the examined eye E, and observe and capture the fundus tissue. As a result, the mobile communication terminal device 10 equipped with the close-up imaging device 20 (that is, smart eye camera) of this embodiment can realize, as a whole, the same functions as an ophthalmic slit lamp microscope.

Further, a main body part 61' of the slit light forming member 61, as illustrated in FIG. 7, includes a first reflecting mirror 65 that reflects the light from the light source 92, a second reflecting mirror 66 that reflects the light reflected by the first reflecting mirror 65, and a slit part 67 for allowing the light reflected by the second reflecting mirror 66 to pass therethrough. The light that passes through the slit part 67 becomes the slit light SL by the cylindrical lens 62. Then, the examined eye E is irradiated with this slit light SL and, while the light including the reflected light RL thereof is concentrated by the convex lens member 93 on the imaging camera lens 91 of the mobile communication terminal device 10, light is received by the image sensor of the camera module, making it possible to observe and capture in detail each tissue of the anterior eye of the examined eye E, including the eyelid, the eye surface, the cornea, the conjunctiva, the lens, and the anterior chamber, and observe and capture the fundus tissue. It should be noted that this cylindrical lens 62 is not particularly limited, but can be selected and adopted from various cylindrical lenses. The slit part 67 is preferably a narrow slit of approximately 1 mm and, as the range, is preferably formed with a width of about 0.7 to 1.5 mm.

The close-up imaging device 20A of this embodiment having the above configuration can (a) observe and capture the anterior eye of the examined eye E (particularly, the lens and each tissue of the anterior chamber) by the slit light forming member 61 and the convex lens member 93 being mounted thereto and the color filter member 97 being removed therefrom. The close-up imaging device 20A of this embodiment can further (b) observe and capture each tissue of the eyelid, the eye surface, the cornea, and the conjunctiva of the examined eye E by the convex lens member 93 only being mounted thereto and the slit light forming member 61 and the color filter member 97 being removed therefrom. In this way, the lens tissue and the anterior chamber tissue can be observed and captured in detail while using the slit light SL generated on the basis of the light-source light emitted from the light source 92 as the observation light. Further, the eyelid, the eye surface, the cornea, and the conjunctiva of the examined eye E can be observed and captured in detail using the light-source light (white diffused light) or the slit light SL passing through the hole 88 as is as the observation light. It should be noted that, in this embodiment, to estimate the state of cataracts in the examined eye E, description will be made presuming that the lens tissue of the examined eye E is observed and captured by using the mobile communication terminal device 10 equipped with the close-up imaging device 20 (smart eye camera) with the color filter member 97 removed from the configuration illustrated in FIGS. 5 to 7 having the slit light forming member 61 and convex lens member 93 mounted thereto. Further, although the close-up imaging device 20A of this embodiment can also observe the fundus tissue (retina) of the examined eye E with the slit light forming member 61 and convex lens member 93 attached, preferably a tubular member 180 (described below) for fundus tissue observation is attached for detailed observation and imaging of the fundus tissue.

As described above, the close-up imaging device 20A of this embodiment can realize the same functions as an expensive ophthalmic slit lamp microscope simply by being mounted to the mobile communication terminal device 10 such as a conventional smartphone. As a result, detailed images of the tissue of the anterior eye such as the eyelid, the eye surface, the cornea, the conjunctiva, the anterior chamber, and the lens of the examined eye E can be captured at low cost and in a simple manner, and a moving image including a diagnosable frame image for cataracts can be easily captured.

[A4] Verification Results of Cataract Diagnosis Using Smart Eye Camera

To compare the smart eye camera with an existing ophthalmic slit lamp microscope, the inventors conducted observations in December 2018 by using the mobile communication terminal device 10 equipped with the close-up imaging device 20A (smartphone, that is, smart eye camera) having the configuration of FIGS. 5 to 7 with the slit light forming member 61 and the convex lens member 93 mounted thereto and the color filter member 97 removed therefrom. It should be noted that the clinical cases at this time were as follows: anterior eye: 58 eyes (21 males and 37 females). Further, the study items included presence or absence of eyelid and anterior eye disease, cataract severity, left-right difference, number of seconds of imaging, and the like. Furthermore, in this verification, the state of dry eye developed in the examined eye E was also observed, and the like, and this is described in detail in the modifications section.

At this time, as the close-up imaging device 20A, a device including the detachable convex lens 96 (focal length: 10 to 30 mm, magnification: 20×) above the imaging camera lens 91 of the mobile communication terminal device 10 for focus adjustment was used. While this convex lens 96 is not particularly limited, in this verification example, TK-12P (manufactured by TSK Co., Ltd.) was used. It should be noted that an illuminance of a digital lux illuminator (model name: LX-1010B, manufactured by Zhangzhou WeiHua Electronic Co., Ltd.) of the mobile communication terminal device 10 used this time was 8000 lux. Further, the close-up imaging device 20A device designed for the iPhone 7 (registered trademark) was utilized for this verification. (Observation Results of Anterior Eye)

Figure 8A:
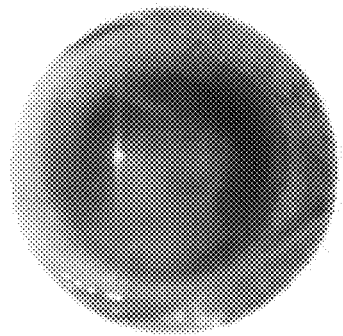
FIGS. 8A to 8F are imaging results of an anterior eye of an examined eye captured by a mobile communication terminal device equipped with the close-up imaging device illustrated in FIG. 5, FIG. 8A showing corneal opacity, FIG. 8B showing post cataract surgery, FIG. 8C showing epidemic conjunctivitis, FIG. 8D showing no cataracts, FIG. 8E showing moderate cataracts, and FIG. 8F showing severe cataracts.
Figure 8B:
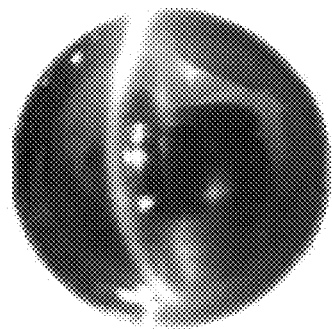
Figure 8C:
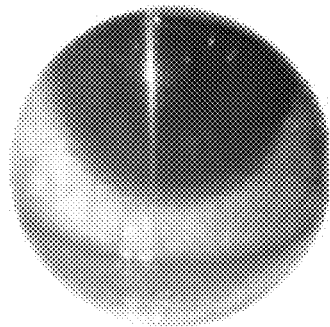
Figure 8D:
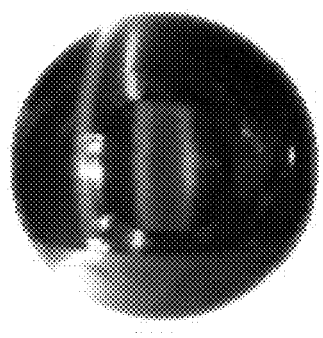
Figure 8E:
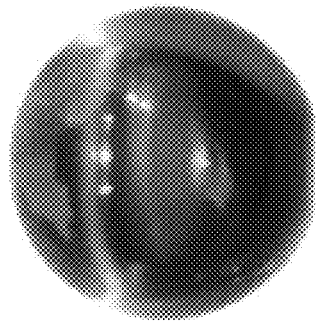
Figure 8F:
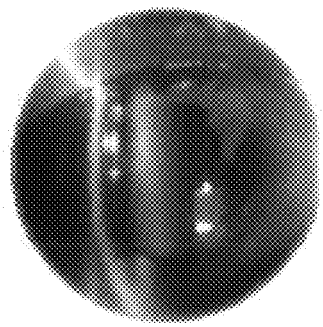

FIGS. 8A to 8F show examples of images actually captured by the mobile communication terminal device 10 equipped with the close-up imaging device 20A illustrated in FIGS. 5 to 7, with the above-described 58 eyes as the target. As shown in FIGS. 8A to 8F, various anterior eye diseases such as pterygium, corneal opacity, epidemic keratoconjunctivitis, and intraocular lens could be evaluated in all cases. It should be noted that, FIG. 8A shows corneal opacity, FIG. 8B shows post cataract surgery, FIG. 8C shows epidemic conjunctivitis, FIG. 8D shows no cataracts, FIG. 8E shows moderate cataracts, and FIG. 8F shows severe cataracts.

Figure 9:
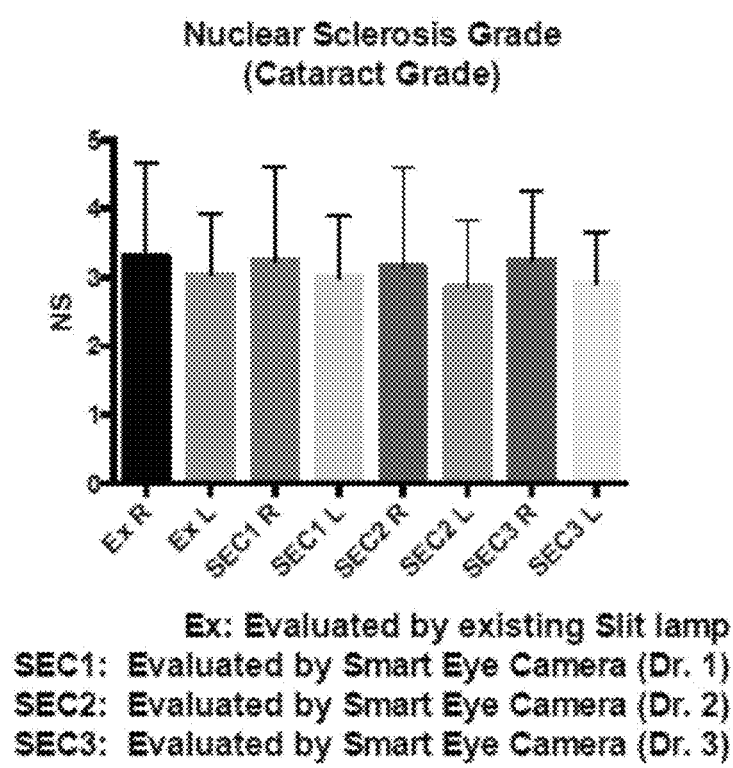
FIG. 9 shows a result of evaluation of nuclear sclerosis (cataracts) by a smart eye camera of the first embodiment.
Figure 10:
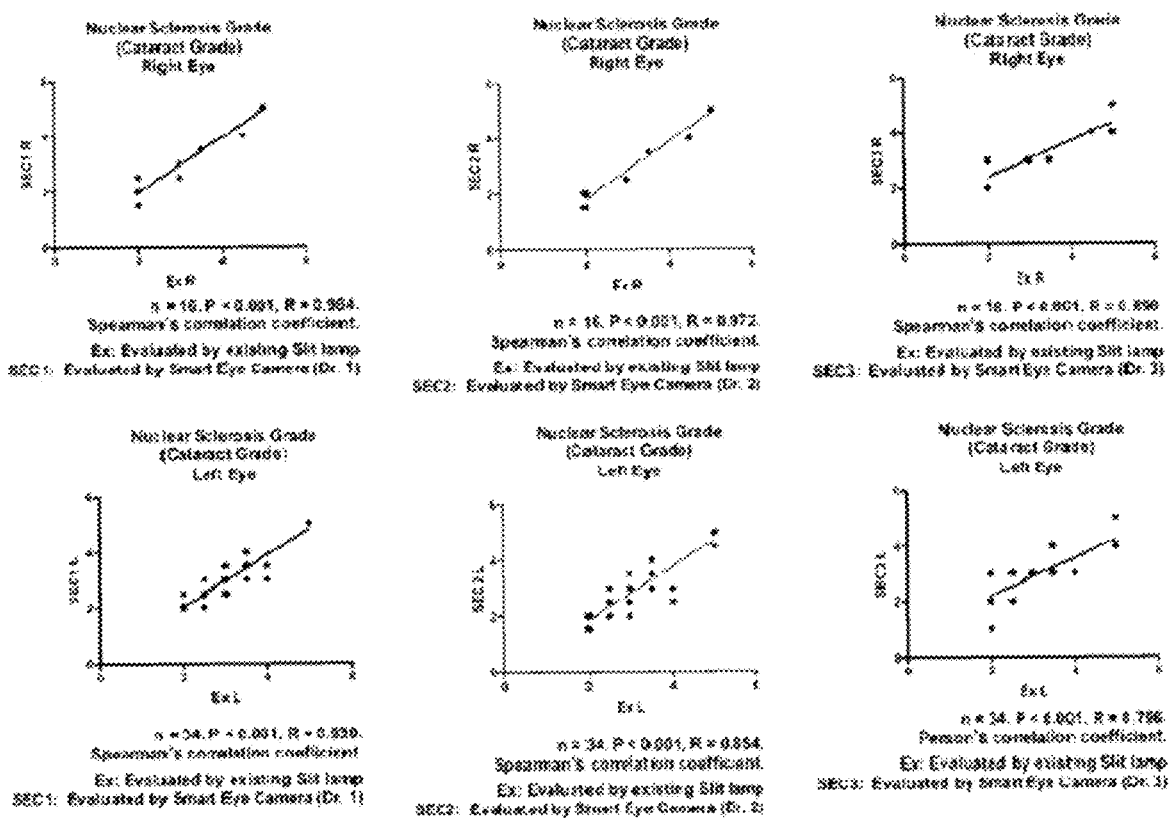
FIG. 10 shows a result of correlation of diagnosis results between the smart eye camera and an existing device by a plurality of eye specialists.

FIG. 9 and FIG. 10 show comparison results of the diagnosis results of cataracts by the mobile communication terminal device 10 equipped with the close-up imaging device 20A illustrated in FIG. 5 to FIG. 7 and the diagnosis results by the existing slit lamp microscope. It should be noted that, in FIG. 9, the vertical axis shows the NS grade that indicates the degree of severity of cataracts, and the horizontal axis shows the EX, which is the evaluation result using the existing device, and SECs 1 to 3 are the results of diagnosis obtained by three eye specialists on the basis of images captured by the mobile communication terminal device 10 equipped with the close-up imaging device 20A illustrated in FIGS. 5 to 7.

As illustrated in FIG. 9, there were no significant differences among any observers or in the left and right eyes as well. Further, FIG. 10 shows a correlation between the results of diagnosis using the mobile communication terminal device 10 equipped with the close-up imaging device 20A by each ophthalmologist, and the results of diagnosis using the existing ophthalmic slit lamp microscope. A correlation was recognized between the mobile communication terminal device 10 equipped with the close-up imaging device 20A and the existing ophthalmic slit lamp microscope, and a high correlation was observed for the left and right eyes as well. These results show that the mobile communication terminal device 10 equipped with the close-up imaging device 20A illustrated in FIG. 5 to FIG. 7 has sufficient objectivity and reproducibility for adapting observational phenotypes of the anterior eye tissue of the examined eye E.

As described above, it was confirmed that the mobile communication terminal device 10 equipped with the close-up imaging device 20A of this embodiment enables observation of various symptoms of the anterior eye of the examined eye E that is by no means inferior to that with the existing ophthalmic slit lamp microscope.

Then, in the diagnosis support system 1 of this embodiment, a moving image of the lens tissue of the examined eye E is captured by using the mobile communication terminal device 10 equipped with the close-up imaging device 20A described above, and the state of cataracts in the examined eye E is estimated on the basis of the captured moving image to generate diagnosis support information. It should be noted that a moving image including a diagnosable frame image can be captured by the same method as that for nuclear sclerosis, for any of the cataract diseases other than nuclear sclerosis, such as atopic cataracts and cortical cataracts, as well With this configuration, the diagnosis support system 1 of this embodiment can capture a moving image including a diagnosable frame that enables diagnosis of a state of cataracts in the examined eye E by using the mobile communication terminal device 10 equipped with the close-up imaging device 20A (that is, smart eye camera) manufacturable at low cost, and estimate the state of cataracts in the examined eye E, without using an existing expensive ophthalmic slit lamp microscope. Further, the smart eye camera of this embodiment can capture a moving image including a diagnosable frame image by basically the same operations as in a conventional device such as a smartphone. Accordingly, even when a paramedic, a family member of the patient, or even the user himself/herself (that is, the patient himself/herself) without expertise captures an image of an eye, the state of cataracts in the examined eye E can be appropriately estimated on the basis of the diagnosable frames included in the captured moving image. It should be noted that, in a case in which the user himself/herself captures an image of his/her own eye as the examined eye E and performs a self-check, the user need only capture a moving image of the examined eye E [that is, the eye on the side to be checked (right eye, for example)] with the smart eye camera while creating a state in which the examined eye E (right eye) is irradiated with the slit light SL. However, in the case of this embodiment, the close-up imaging device 20A is configured to utilize the out-camera module of the mobile communication terminal device 10. Thus, in a case in which a moving image is actually captured, the user need only open both eyes in front of a mirror, project the image being captured (that is, the image reflecting the right eye) displayed on the display unit of the mobile communication terminal device 10 onto the mirror while irradiating the right eye that is the examined eye E with the slit light SL and, while checking the image being captured using the left eye (that is, the eye opposite to the examined eye E) via the mirror and adjusting a position and an orientation of the smart eye camera, capture a moving image of his/her own right eye.

[A5] Configuration of Diagnosis Support Server Device 30

Next, a configuration of the diagnosis support server device 30 of this embodiment will be described with reference to FIGS. 11 and 12. It should be noted that FIG. 11 is a block diagram illustrating a configuration example of the diagnosis support server device 30 of this embodiment, and FIG. 12 is an image diagram for describing processes executed by a diagnosis processing unit 350 of this embodiment.

Figure 11:
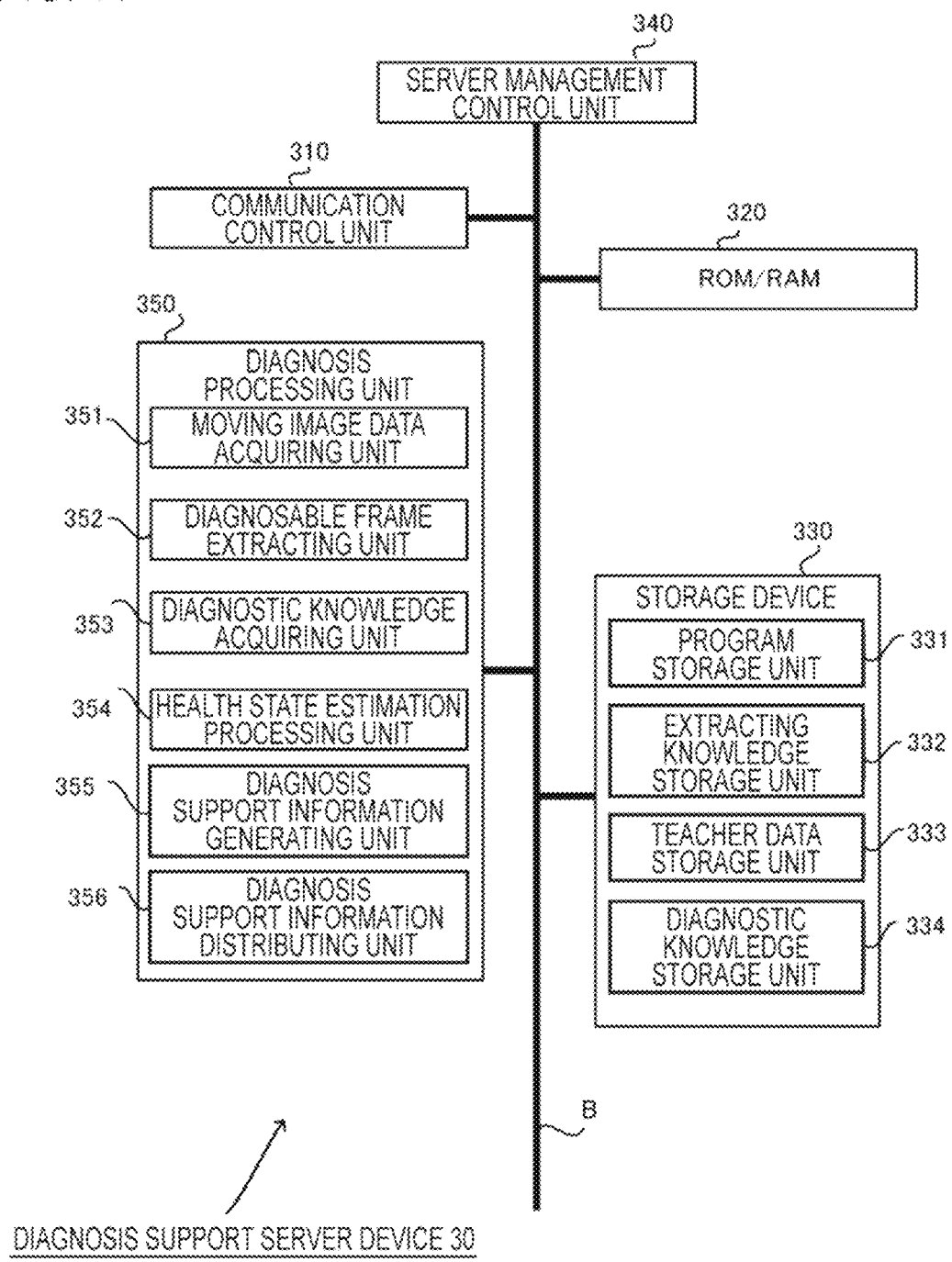
FIG. 11 is a block diagram illustrating a configuration example of a diagnosis support server device of the first embodiment.
Figure 12:
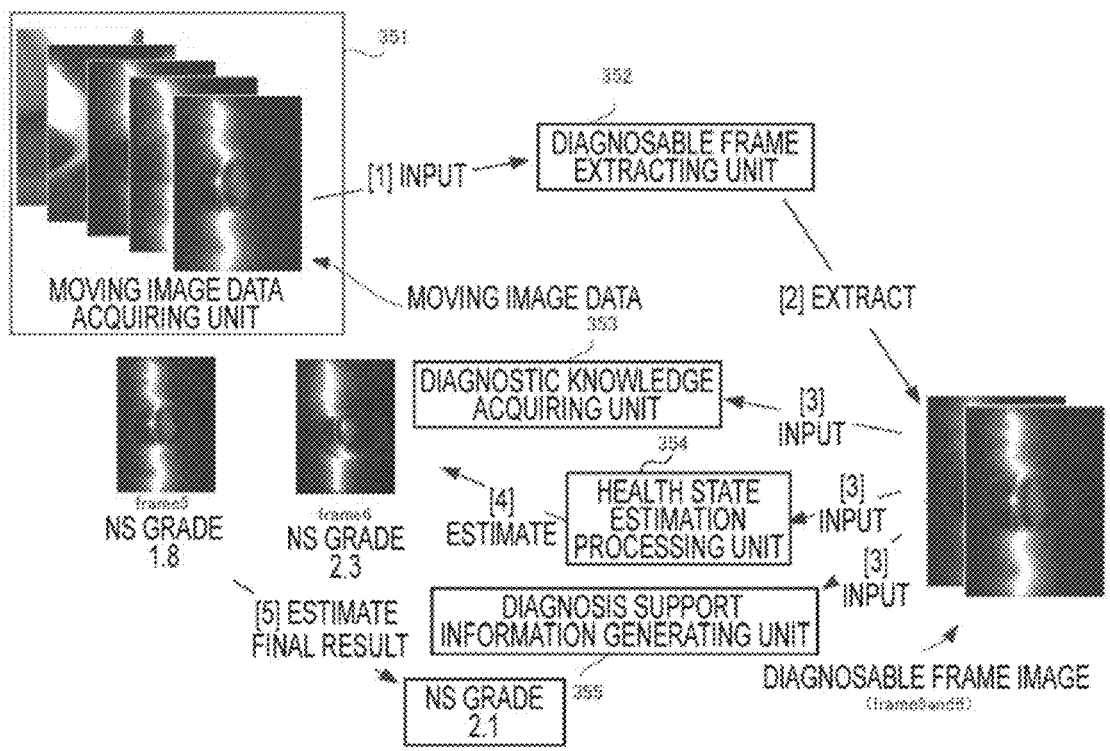
FIG. 12 is an image diagram for describing processes executed by a diagnosis processing unit of the first embodiment.

As illustrated in FIG. 11, the diagnosis support server device 30 of this embodiment includes a communication control unit 310 communicably connected to the network N, a ROM/RAM 320 that functions as various types of memory, a storage device 330, a server management control unit 340 that controls the overall device, and the diagnosis processing unit 350 that executes the processing of (1) acquiring moving image data uploaded from the mobile communication terminal device 10, (2) extracting diagnosable frames from the moving image data, (3) estimating the state of cataracts in the examined eye E on the basis of the diagnosable frames, (4) generating diagnosis support information on the basis of the estimation results, and (5) distributing the generated diagnosis support information to the corresponding mobile communication terminal device 10. It should be noted that the components described above are interconnected by a bus B, and data transfers are executed between the components.

The communication control unit 310 is a predetermined network interface, and is communicably connected to the mobile communication terminal device 10 via the network N. Further, the communication control unit 310 is communicably connected to the annotation terminal device 40 directly or via the network N, and exchanges various data between the mobile communication terminal device 10 and the annotation terminal device 40.

The ROM/RAM 320 stores various programs necessary to drive the diagnosis support server device 30. Further, the ROM/RAM 320 is used as a work area when various processes are executed.

The storage device 330 is constituted by a hard disc drive (HDD) or a solid state drive (SSD).

Then, the storage device 330 is provided with (a1) a program storage unit 331, (a2) an extracting knowledge storage unit 332, (a3) a teacher data storage unit 333, and (a4) a diagnostic knowledge storage unit 334. It should be noted that the extracting knowledge storage unit 332 and the diagnostic knowledge storage unit 334 of this embodiment constitute the "first storage means" and the "second storage means" of the present invention, for example.

The program storage unit 331 stores, for example, programs such as a basic input/output system (BIOS) and an operating system (OS) as well as (b1) a diagnosable frame image extracting program for executing a process of extracting diagnosable frame images on the basis of the moving image data of the examined eye E uploaded from the mobile communication terminal device 10 and the extracting knowledge, (b2) a diagnostic knowledge acquisition program for executing a process of acquiring the diagnostic knowledge, and (b3) a diagnosis support information generating program for executing a process of generating and distributing diagnosis support information on the basis of the diagnosable frame images and the diagnostic knowledge.

The extracting knowledge storage unit 332 stores, in advance, knowledge necessary to extract frame images that satisfy all of the above-described conditions 1 to 3 as knowledge for extracting diagnosable frame images that enable diagnosis of the state of cataracts in the examined eye E. It should be noted that the specific method of acquiring the extracting knowledge and data format in this embodiment are as desired and, for example, the system may be configured to acquire weight and bias parameters as the extracting knowledge by inputting any diagnosable frame image extracted by the annotator as teacher data into a convolutional neural network (also referred to as the "ConvNet"), which constitutes a diagnosable frame extracting unit 352 described below, and store the knowledge in the extracting knowledge storage unit 332.

The teacher data storage unit 333 stores teacher data acquired from the annotation terminal device 40 each time moving image data is uploaded from the mobile communication terminal device 10.

The diagnostic knowledge storage unit 334 stores diagnostic knowledge for estimating the presence or absence of cataracts, the NS grade, the treatment method, the necessity for surgery, and the like in the examined eye E.

The server management control unit 340 is mainly constituted by a CPU, and integrally controls the components of the diagnosis support server device 30 by executing programs such as the OS and the BIOS.

The diagnosis processing unit 350 is configured by using the same CPU as the CPU that realizes the server management control unit 340, or is constituted by a CPU independent of the server management control unit 340. Then, the diagnosis processing unit 350 executes programs stored in the program storage unit 331 under the control of the server management control unit 340, thereby realizing (c1) a moving image data acquiring unit 351, (c2) the diagnosable frame extracting unit 352, (c3) a diagnostic knowledge acquiring unit 353, (c4) a health state estimation processing unit 354, (c5) a diagnosis support information generating unit 355, and (c6) a diagnosis support information distributing unit 356.

(Moving Image Data Acquiring Unit 351)

The moving image data acquiring unit 351, in linkage with the communication control unit 310, acquires moving image data capturing the examined eye E from the mobile communication terminal device 10 and inputs the acquired moving image data to the diagnosable frame extracting unit 352 (step [1] in FIG. 12). It should be noted that the moving image data acquiring unit 351 of this embodiment, in linkage with the communication control unit 310, constitutes the "acquisition means" of the present invention, for example.

(Diagnosable Frame Extracting Unit 352)

Figure 13:
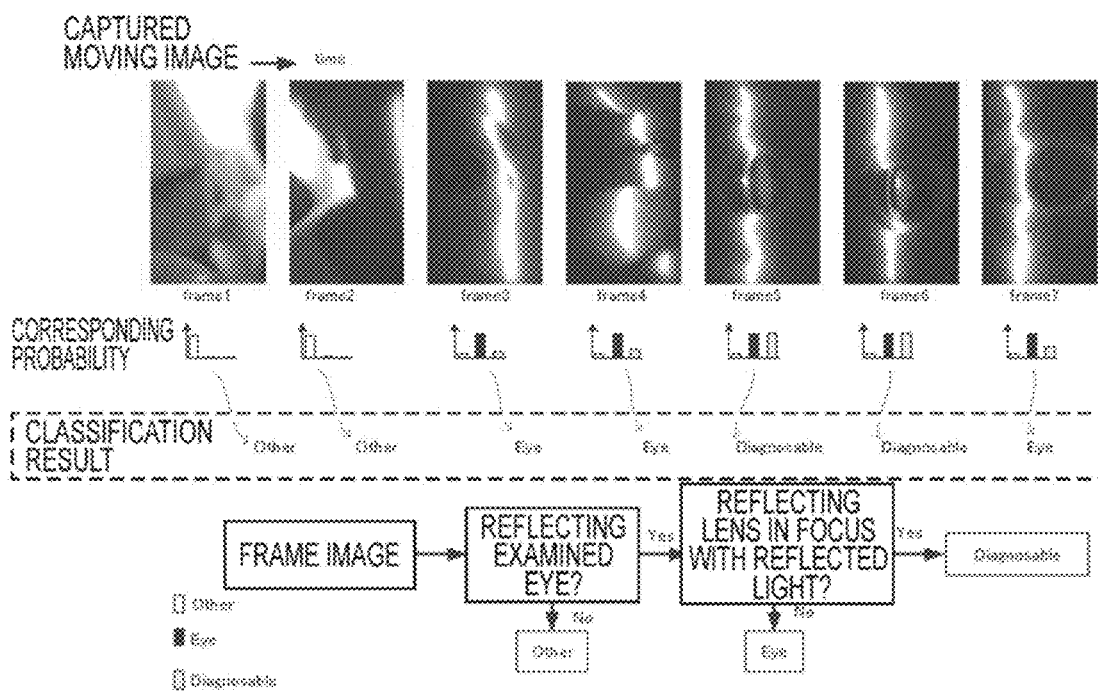
FIG. 13 is an image diagram for describing a diagnosable frame image extraction process executed by a diagnosable frame extracting unit of the first embodiment.

The diagnosable frame extracting unit 352 is, for example, constructed as a convolutional neural network using a CPU. Then, in accordance with the diagnosable frame image extracting program, the diagnosable frame extracting unit 352 extracts diagnosable frame images from the moving image data by executing the diagnosable frame image extraction process illustrated in FIG. 13 on the basis of the moving image data input from the moving image data acquiring unit 351 and the extracting knowledge (step [2] in FIG. 12). The diagnosable frame extracting unit 352 then inputs the extracted diagnosable frame images to each component of the diagnostic knowledge acquiring unit 353, the health state estimation processing unit 354, and the diagnosis support information generating unit 355 (step [3] in FIG. 12). It should be noted that the method by which the diagnosable frame extracting unit 352 inputs the diagnosable frame images to each of the units 353, 354, 355 is as desired, and the images may be input directly from the diagnosable frame extracting unit 352 to the units 353, 354, 355. However, in this embodiment, an explanation will be given assuming adoption of a configuration in which the diagnosable frame images extracted by the diagnosable frame extracting unit 352 are temporarily stored in the ROM/RAM 320, and the units 353, 354, 355 read the images from the ROM/RAM 320 as necessary. Further, the number of frame images constituting the moving image data is as desired. For example, about 200 out of 600 to 1200 frames captured over a period of 20 to 40 seconds at a frame rate of 30 fps with a smart eye camera may be utilized. It should be noted that, to prevent the drawings from becoming cumbersome, FIG. 13 is exemplified by extracting only seven frames (frames 1 to 7) included in these 200 frames. Further, the diagnosable frame extracting unit 352 of this embodiment constitutes the "first extraction means" of the present invention, for example.

[A5.1] Principle of Diagnosable Frame Image Extraction Process

Next, the principle of the diagnosable frame image extraction process executed by the diagnosable frame extracting unit 352 of this embodiment will be described with reference to FIG. 13. It should be noted that FIG. 13 is an image diagram for describing the diagnosable frame image extraction process executed by the diagnosable frame extracting unit 352 of this embodiment in accordance with the diagnosable frame image extracting program.

As illustrated in FIG. 13, in this process, the diagnosable frame extracting unit 352 determines whether or not the examined eye E appears in each frame image included in the input moving image data. Then, when the examined eye E is not reflected, the diagnosable frame extracting unit 352 classifies the frame image as Other. The frame images classified as "Other" do not reflect the examined eye E in the first place, and thus the diagnosable frame extracting unit 352 thins out the frames and, for each of the remaining frame images, determines whether or not at least a portion of the lens tissue is reflected in focus along with, of the slit light SL, the reflected light RL in the lens tissue.

Then, the diagnosable frame extracting unit 352 classifies only frame images in which at least a portion of the lens tissue is reflected in focus along with the reflected light RL as Diagnosable. On the other hand, the diagnosable frame extracting unit 352 classifies the other frame images (that is, frame images in which at least a portion of the lens tissue is not reflected along with, of the slit light SL, the reflected light RL in the lens tissue or is not in focus in the lens tissue) as Eye. As a result, by this process, only frame images that satisfy the above-described three conditions are classified as "Diagnosable," and other frame images are classified as "Other" or "Eye." For example, FIG. 13 illustrates an example of a case in which frames 1 and 2 are classified as "Other," frames 3, 4, and 7 are classified as "Eye," and frames 5 and 6 are classified as "Diagnosable" on the basis of the above-described conditions.

At this time, the diagnosable frame extracting unit 352 calculates the probability (or likelihood) of being classified as "Other," "Eye," and "Diagnosable" for each frame image included in the moving image data as illustrated in FIG. 13. Then, the diagnosable frame extracting unit 352 is configured to classify each frame image as any one of "Other," "Eye," or "Diagnosable" on the basis of the corresponding probability calculated.

It should be noted that, at this time, the probability of being classified into each class may be calculated for all frame images included in the moving image data. However, in a case in which a configuration is adopted in which the corresponding probability is calculated for all frame images, the processing burden on the diagnosable frame extracting unit 352 may increase. For this reason, in this embodiment, a configuration is adopted in which the tissue in focus in each frame image included in the moving image data is labeled with a tissue name in advance, only the frame images in which the lens tissue is in focus are extracted on the basis of the label attached to each frame image, and the probability of being classified into each class is calculated for each of the extracted frame images.

With this configuration, the diagnosis support server device 30 of this embodiment can thin out in advance the frame images in which the lens tissue is not in focus and extract diagnosable frame images from the remaining frame images. As a result, it is possible to reduce the processing burden of the diagnosable frame image extraction process, and simplify image classification problems during diagnosable frame image extraction can be simplified, to improve the accuracy and the reproducibility during diagnosable frame image extraction. It should be noted that the specific method for labeling the tissue in focus in each frame image with the tissue name is as desired and, for example, a configuration may be adopted in which the diagnosable frame extracting unit 352 is equipped with a standard label engine for ocular tissue, and this standard label engine is used to label the tissue in focus in each frame image with the tissue name. Further, in a case in which the examined eye E is captured from the front, a plurality of tissues of the anterior eye, such as the eyelid, the eye surface, the cornea, and the conjunctiva, for example, may be reflected in focus simultaneously in a single frame image. For this reason, the diagnosable frame extracting unit 352 is configured to perform, for each pixel in each frame image, multi-labeling in which the name of the tissue reflected in the pixel is labeled. It should be noted that the specific criteria for classifying each frame image into each class on the basis of the corresponding probability calculated by the diagnosable frame extracting unit 352 are as desired and, for example, the probabilities of being classified into each of the three classes may be compared and the frame image may be classified into the class having the highest probability, or may be classified into the class having a probability exceeding a predetermined threshold value (60%, for example).

Then, the diagnosable frame extracting unit 352 extracts the diagnosable frame images from among all frame images included in the moving image data on the basis of the calculated probability. It should be noted that the specific criteria for extracting diagnosable frame images by the diagnosable frame extracting unit 352 on the bases of the calculated probability are as desired. For example, a configuration may be adopted in which all frame images classified as "Diagnosable" (frames 5 and 6 in FIG. 13, for example) are uniformly extracted as diagnosable frame images, or frame images having a probability of being classified as "Diagnosable" that exceeds a predetermined threshold value (60%, for example) is extracted as diagnosable frame images. However, in this embodiment, for the sake of specificity of explanation, description will be made presuming adoption of a configuration in which a predetermined top number of frame images having a high probability of being classified as "Diagnosable" (top few frames having the high probability or top few percent of frames having the high probability, for example) are extracted as diagnosable frame images.

When diagnosable frame images are extracted by the above diagnosable frame image extraction process, the diagnosable frame extracting unit 352 stores, by associating the extracted diagnosable frame images with the probabilities of the diagnosable frame image being classified as "Diagnosable," the data in the ROM/RAM 320. As a result, the probability of each diagnosable frame image being classified as "Diagnosable" can be specified when the health state estimation processing unit 354 subsequently estimates the presence or absence of cataracts, the NS grade, and the like in the examined eye E on the basis of each diagnosable frame image.

(Diagnostic Knowledge Acquiring Unit 353)

The diagnostic knowledge acquiring unit 353 is, for example, constructed as a convolutional neural network using a CPU. Then, the diagnostic knowledge acquiring unit 353 transmits the diagnosable frame images extracted by the diagnosable frame extracting unit 352 to the annotation terminal device 40 in accordance with the diagnostic knowledge acquisition program, thereby acquiring teacher data from the annotation terminal device 40 and storing the data in the teacher data storage unit 333. Further, when the quantity of teacher data accumulated in the teacher data storage unit 333 reaches a or greater, the diagnostic knowledge acquiring unit 353 acquires diagnostic knowledge by executing at least one of machine learning and data mining on the basis of the teacher data, and stores the knowledge in the diagnostic knowledge storage unit 334. It should be noted that the specific method for acquiring diagnostic knowledge by the diagnostic knowledge acquiring unit 353 and the specific contents of the diagnostic knowledge in this embodiment are as desired. For example, the system may be configured to acquire weight and bias parameters obtained by inputting the teacher data accumulated in the teacher data storage unit 333 as diagnostic knowledge into the convolutional neural network constituting the diagnostic knowledge acquiring unit 353, and store the parameters in the diagnostic knowledge storage unit 334. Further, the diagnostic knowledge acquiring unit 353 of this embodiment, in linkage with the communication control unit 310 and the annotation terminal device 40, constitutes the "learning means" of the present invention, for example. Furthermore, the specific number of a in this embodiment is as desired. However, to acquire diagnostic knowledge, it is necessary to utilize at least about several hundred samples of teacher data. Nevertheless, the diagnosis support system 1 of this embodiment is configured to extract a plurality of diagnosable frame images (top few frames or top few percent of frames having high probability, for example) from one set of moving image data and create teacher data for each diagnosable frame image, making it possible to create a large quantity of teacher data from a small quantity of moving image data and acquire diagnostic knowledge. For example, in a case in which 1000 teacher data are needed as α, and 5 diagnosable frame images are extracted from 1 set of moving image data, 1000 teacher data can be created from 200 moving image data to acquire the necessary diagnostic knowledge.

(Health State Estimation Processing Unit 354)

The health state estimation processing unit 354 is, for example, constructed as a convolutional neural network using a CPU. Then, the health state estimation processing unit 354 estimates the presence or absence of cataracts, the NS grade, and the like in the examined eye E on the basis of the diagnostic knowledge stored in the diagnostic knowledge storage unit 334 and the diagnosable frame images extracted by the diagnosable frame extracting unit 352, in accordance with a health state estimating program. It should be noted that the health state estimation processing unit 354 of this embodiment constitutes the "estimation means" of the present invention, for example.

In particular, as a distinctive feature in this embodiment, the health state estimation processing unit 354 is configured to estimate the NS grade and the like for each diagnosable frame image on the basis of each of the plurality of diagnosable frame images extracted by the diagnosable frame extracting unit 352 (refer to FIG. 12). Then, the health state estimation processing unit 354 estimates the most plausible state of cataracts in the examined eye E on the basis of a value of the NS grade estimated on the basis of each diagnosable frame image. For example, FIGS. 12 and 13 show an example of a case in which, when frames 5 and 6 included in the moving image data are extracted as diagnosable frame images and the NS grades of "1.8" and "2.3" are estimated for the respective frames, the health state estimation processing unit 354 estimates the value of the NS grade of "2.1" as the most plausible health state of the examined eye E on the basis of these estimation results.

At this time, conceivable methods by which the health state estimation processing unit 354 estimates the most plausible health state of the examined eye E include (1) a method of taking the average of the NS grade estimated values corresponding to each diagnosable frame image, and (2) a method of deciding by majority in terms of the estimation results for each diagnosable frame image. However, in this embodiment, the explanation will be given assuming that the health state estimation processing unit 354 executes ensemble machine learning on the basis of NS grade estimated values corresponding to each diagnosable frame image to estimate the most plausible health state of the examined eye E. Specifically, the health state estimation processing unit 354 estimates the most plausible health state of the examined eye E by weighting the NS grade estimated values based on each diagnosable frame image by the probability of being classified as "Diagnosable" calculated by the diagnosable frame extracting unit 352. For example, in a case in which five frame images are extracted as diagnosable frame images and the NS grade estimated values are obtained for each, the health state estimation processing unit 354 estimates the most plausible health state of the examined eye E by regressing the NS grade estimated values using [Estimated value, Probability (Diagnosable)]*5 as input.

Usually, in a case in which a classifier is used to estimate the NS grade of cataracts in the examined eye E, an estimated value based on diagnosable frame images having a high probability of being classified as "Diagnosable" yields a correct answer rate higher than estimated values based on diagnosable frame images having a low probability. Accordingly, by weighting the estimated values of the NS grade by the probability of being classified as "Diagnosable" calculated for each diagnosable frame image by the above-described configuration, it is possible to increase the weight of estimated values having high correct answer rate and appropriately estimate the most plausible health state of the examined eye E and thus improve the reliability of the diagnosis support information. It should be noted that, in a case in which strict reliability of diagnosis support information is not required, a configuration may be adopted in which the state of cataracts in the examined eye E may be estimated on the basis of only the best frame having the highest probability of being classified as "Diagnosable" in the diagnosable frame image extraction process. Further, the method of estimating a state other than NS grade is as desired and, for example, another state may be determined by majority, or the estimation result based on the diagnosable frame image having the highest probability of being classified as "Diagnosable" may be utilized.

(Diagnosis Support Information Generating Unit 355)

The diagnosis support information generating unit 355 generates diagnosis support information including the estimation result of the health state of the examined eye E by the health state estimation processing unit 354 by executing processing according to the diagnosis support information generating program. It should be noted that the health state estimation processing unit 354 of this embodiment constitutes the "generation means" and the "second extraction means" of the present invention, for example.

In particular, as a distinctive feature in this embodiment, the diagnosis support information generating unit 355 is configured to extract the diagnosable frame image in which the state of cataracts in the examined eye E is most easily recognized on the basis of the labeling of the tissue name by the diagnosable frame extracting unit 352, and to generate diagnosis support information including the diagnosable frame image. In general, the diagnosable frame image reflecting the largest amount of lens tissue is the image in which the state of cataracts is most easily recognized. For this reason, in this embodiment, the diagnosis support information generating unit 355 extracts, as a frame image for user presentation (hereinafter referred to as "frame image for presentation"), the diagnosable frame image in which an area of the pixel region reflecting the lens tissue is largest on the basis of the diagnosable frame images labeled with a tissue name for each pixel in the diagnosable frame extracting unit 352. Then, the diagnosis support information generating unit 355 generates diagnosis support information including the estimation results related to the state of cataracts and the frame image for presentation.

With this configuration, according to the diagnosis support system 1 of this embodiment, it is possible to generate diagnosis support information including an image by which the user can most easily recognize the state of cataracts. As a result, it is possible to dramatically improve the UX of a patient when the user describes symptoms to the patient or when the patient himself or herself self-checks his or her own eye health state.

(Diagnosis Support Information Distributing Unit 356)

The diagnosis support information distributing unit 356, in linkage with the communication control unit 310, distributes the diagnosis support information generated by the diagnosis support information generating unit 355 to the mobile communication terminal device 10 from which the moving image data was uploaded. It should be noted that the diagnosis support information distributing unit 356 of this embodiment, in linkage with the communication control unit 310, constitutes the "distribution means" of the present invention, for example. Further, the target for distribution of diagnosis support information by the diagnosis support information distributing unit 356 is not limited to the mobile communication terminal device 10 from which the moving image data was uploaded, and may be, for example, another communication terminal device utilized by the user (PC, for example) or a communication terminal device unrelated to the user (computer system owned by a cataract research institute or the like, for example).

[A6] Operation of Diagnosis Support System 1

[A6.1] Diagnostic Knowledge Acquiring Process

Figure 14:
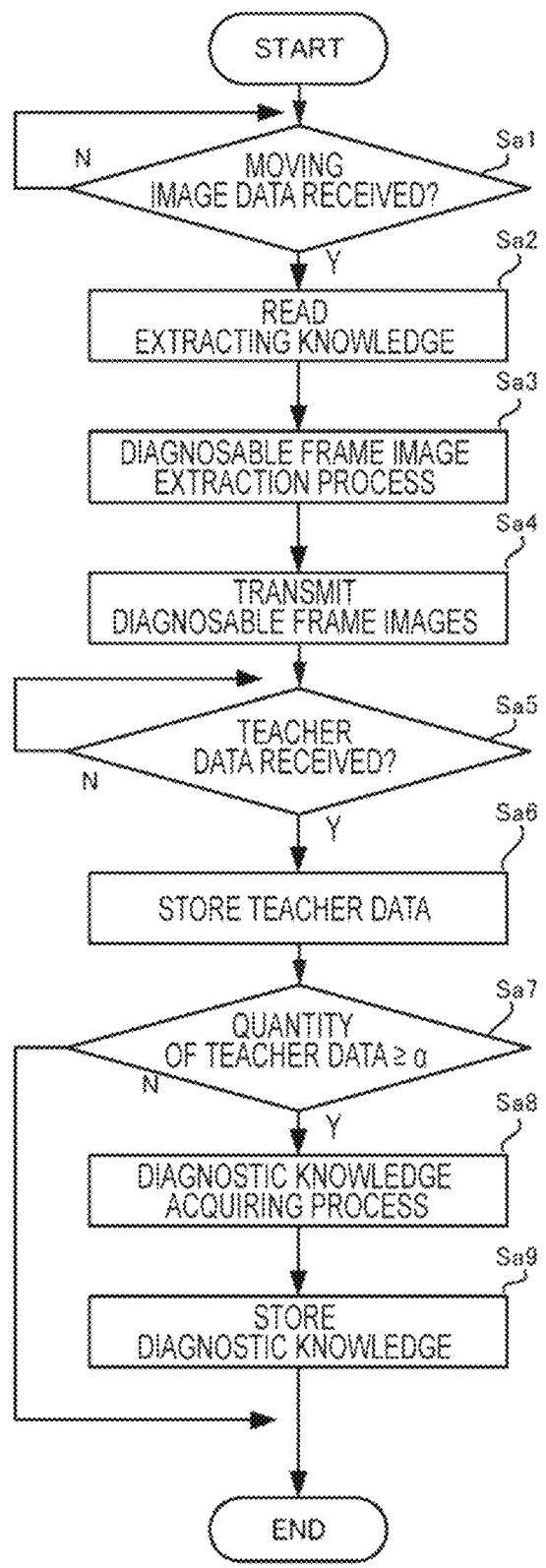
FIG. 14 is a flowchart illustrating a diagnostic knowledge acquiring process executed in the diagnosis processing unit of the diagnosis support server device of the first embodiment.

Next, the diagnostic knowledge acquiring process executed in the diagnosis support system 1 of this embodiment will be described with reference to FIG. 14. It should be noted that FIG. 14 is a flowchart illustrating the diagnostic knowledge acquiring process executed by the diagnosis processing unit 350 of this embodiment in linkage with the mobile communication terminal device 10 and the annotation terminal device 40 in accordance with the diagnostic knowledge acquisition program and the diagnosable frame image extracting program.

Prior to this process, the extracting knowledge storage unit 332 stores in advance the extracting knowledge required to extract diagnosable frame images for cataracts.

Further, in a case in which diagnostic knowledge for cataracts is acquired in the diagnosis support system 1 of this embodiment, it is necessary to capture a moving image including diagnosable frame images for cataracts by using a smart eye camera. For this reason, it is assumed that, prior to this process, the user has removed the color filter member 97 from the close-up imaging device 20A, which constitutes a smart eye camera, and attached the convex lens member 93 and the slit light forming member 61 so that the close-up imaging device 20A has a configuration such as illustrated in FIGS. 5 to 7.

In this state, when the user performs a predetermined input operation on an operation unit (not illustrated) of the mobile communication terminal device 10, the camera module is activated in the mobile communication terminal device 10 in accordance with the diagnostic app. As a result, on the mobile communication terminal device 10, the image being captured and a string indicating the operation procedure, such as the message, "Please make adjustments so that the slit light SL strikes the pupil of the eye to be diagnosed, press the start button, and capture a video of the eye for about 20 to 40 seconds. At this time, you are more likely to receive an accurate diagnosis if you capture the video by slowly scanning the pupil area while gradually changing the angle at which the pupil is irradiated with the slit light. Further, when you have finished capturing the video, press the stop button and then press the send button." along with the "Start Video," "Stop," and "Send" buttons are displayed on the display unit. It should be noted that, the operation procedure and each button may be displayed superimposed on the image being captured, or may be displayed in a display region separate from the image being captured. Furthermore, the operation procedure may be guided by voice.

Then, when the user selects the Start Video button in accordance with the operation procedure displayed on the display unit, the light source 92 emits light in the mobile communication terminal device 10, the slit light SL is irradiated in the front direction, and the camera module starts capturing a moving image. In this state, when the user irradiates the lens tissue of the examined eye E with the slit light SL and slowly scans the pupil of the examined eye E with the slit light SL while changing the irradiation angle of the slit light SL, the light including the reflected light RL of the slit light SL in the examined eye E is condensed on the imaging camera lens 91 by the convex lens member 93 of the close-up imaging device 20A and moving image data including a series of frame images such as exemplified in FIG. 13 is generated. At this time, the camera module of the mobile communication terminal device 10 captures a moving image while automatically focusing on the lens tissue by using an auto-focus mechanism, which is the same as a conventional mobile communication terminal device such as a smartphone.

When the user then performs the input operations of selecting the Stop button and the Send button in this order after capturing the lens tissue of the examined eye E for about 20 to 40 seconds, for example, in accordance with the operation procedure, the mobile communication terminal device 10 uploads the captured moving image data to the diagnosis support server device 30 in accordance with the diagnostic app.

When the moving image data thus uploaded from the mobile communication terminal device 10 is received by the communication control unit 310 of the diagnosis support server device 30 (step Sa1), the diagnosable frame extracting unit 352 in the diagnosis processing unit 350 reads the extracting knowledge from the extracting knowledge storage unit 332 (step Sa2). Then, in accordance with the diagnosable frame image extracting program, the diagnosable frame extracting unit 352 executes the diagnosable frame image extraction process illustrated in FIG. 13, extracts diagnosable frame images included in the moving image data, and stores the images in the ROM/RAM 320 (step Sa3).

Next, the diagnostic knowledge acquiring unit 353 transmits all diagnosable frame images stored in the ROM/RAM 320 to the annotation terminal device 40 (step Sa4). It should be noted that the form in which the diagnostic knowledge acquiring unit 353 transmits diagnosable frame images to the annotation terminal device 40 is as desired, and a configuration may be adopted in which the diagnosable frame images are transmitted to all annotation terminal devices 40 in the same broadcast, or all diagnosable frame images are transmitted only to some annotation terminal devices 40.

Upon receiving the diagnosable frame images extracted from the moving image data in this way, the annotation terminal device 40 displays a string such as, for example, "Please enter the diagnosis result of cataracts on the basis of this image" and a graphic user interface (GUI) for inputting the diagnosis result on a monitor (not illustrated) along with each diagnosable frame image. It should be noted that the display mode at this time is as desired and, by associating and displaying different diagnosable frame images with the GUI for inputting the diagnosis results in each display region while dividing the display region of the monitor, a diagnostic screen based on all diagnosable frame images may be displayed at once, or the diagnosable frame images may be displayed one at a time while being switched.

In this state, when a physician, who is an annotator, diagnoses the presence or absence of cataracts, the NS grade, the treatment method, the necessity of surgery, and the like on the basis of each diagnosable frame image displayed and inputs the diagnosis results in accordance with the GUI, the annotation terminal device 40 generates diagnosis result information in correspondence with the input operation. Then, the annotation terminal device 40 creates teacher data corresponding to each diagnosable frame image by tagging the corresponding diagnosable frame image with the diagnosis result information, and transmits the created teacher data to the diagnosis support server device 30. For example, in a case in which five diagnosable frame images are extracted in the diagnosable frame image extraction process, the annotation terminal device 40 creates five teacher data corresponding to each diagnosable frame image and transmits the data to the diagnosis support server device 30.

On the other hand, in the diagnosis support server device 30, when the communication control unit 310 receives teacher data from the annotation terminal device 40 ("Yes" in step Sa5), the diagnostic knowledge acquiring unit 353 stores the received teacher data in the teacher data storage unit 333 (step Sa6) and then determines whether or not the quantity of teacher data stored in the teacher data storage unit 333 is a or greater (step Sa7). Then, in a case in which the quantity of teacher data is less than a ("No" in step Sa7), the diagnostic knowledge acquiring unit 353 ends the process.

Each time moving image data is uploaded from the mobile communication terminal device 10, the processes of steps Sa1 to Sa7 are repeatedly executed in the diagnosis processing unit 350, and the teacher data is sequentially accumulated in the teacher data storage unit 333. For example, when α is set to 1000 and the method of extracting the top five frames having the highest probability as diagnosable frame images is adopted, the teacher data is sequentially accumulated in the teacher data storage unit 333 from 1st to the 199th moving image data uploads, and the process ends. On the other hand, during the 200th moving image data upload, the quantity of teacher data stored in the teacher data storage unit 333 is α(1000) or greater, and thus the diagnostic knowledge acquiring unit 353 makes the determination "Yes" in step Sa7, acquires the diagnostic knowledge by executing at least one of machine learning and data mining on the basis of the teacher data accumulated in the teacher data storage unit 333 (step Sa8), stores the diagnostic knowledge in the diagnostic knowledge storage unit 334 (step Sa9), and ends the process.

[A6.2] Diagnosis Support Information Generation Process

Figure 15:
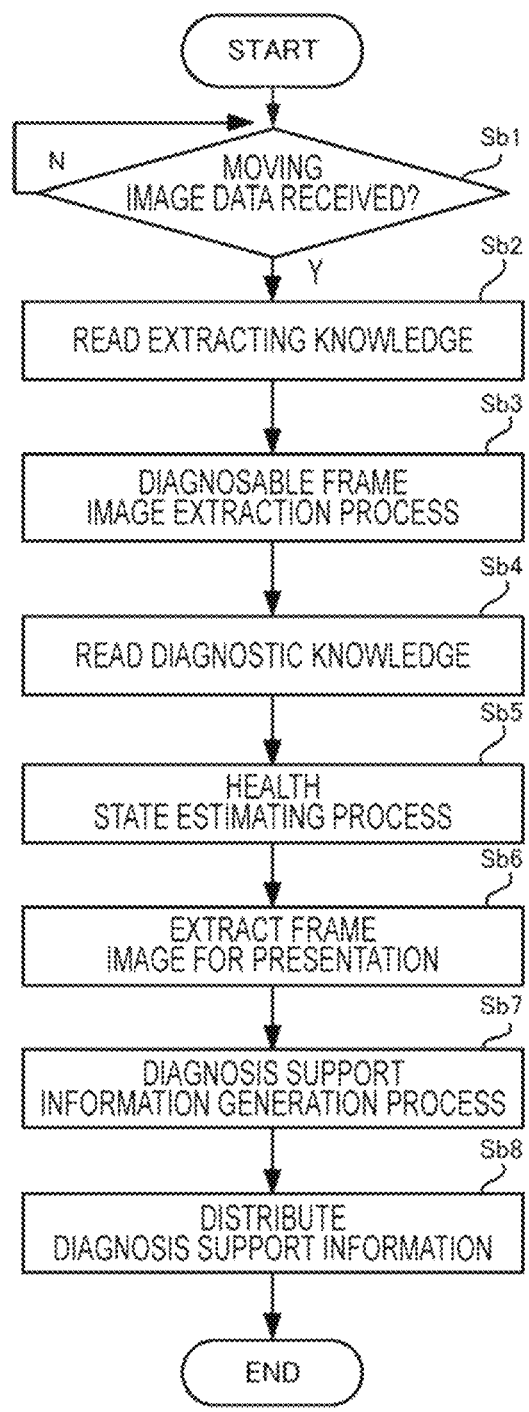
FIG. 15 is a flowchart illustrating a diagnosis support information generation process executed in the diagnosis processing unit of the diagnosis support server device of the first embodiment.

Next, the diagnosis support information generation process executed in the diagnosis support server device 30 of this embodiment will be described with reference to FIG. 15. It should be noted that FIG. 15 is a flowchart showing the diagnosis support information generation process executed by the diagnosis processing unit 350 in linkage with the mobile communication terminal device 10 in accordance with the diagnosis support information generating program and the diagnosable frame image extracting program.

Prior to this process, it is assumed that the required knowledge is already stored in the extracting knowledge storage unit 332 and the diagnostic knowledge storage unit 334. Further, it is assumed that the user has already configured the close-up imaging device 20A, which constitutes a smart eye camera, to be capable of capturing a moving image including diagnosable frame images for cataracts, as described above. That is, the close-up imaging device 20A is configured with the slit light forming member 61 and the convex lens member 93 mounted thereto and the color filter member 97 removed therefrom.

In this state, when the user captures a moving image of the examined eye E and selects the Send button, and the moving image data is uploaded from the mobile communication terminal device 10 ("Yes" in step Sb1), the diagnosable frame extracting unit 352 in the diagnosis processing unit 350 reads the extracting knowledge from the extracting knowledge storage unit 332 (step Sb2) and subsequently executes the diagnosable frame image extraction process in accordance with the diagnosable frame image extracting program. As a result, the diagnosable frame images included in the moving image data are extracted and associated with respective diagnosable frame images and the probability of the corresponding diagnosable frame image being classified as "Diagnosable" is stored in the ROM/RAM 320 (step Sb3).

Next, the health state estimation processing unit 354 reads the diagnostic knowledge (step Sb4), executes the health state estimating process on the basis of the diagnosable frame images and the diagnostic knowledge stored in the ROM/RAM 320 (step Sb5), and estimates the state of cataracts in the examined eye E. At this time, the health state estimation processing unit 354 estimates the state of cataracts for each diagnosable frame image, as illustrated in FIG. 12. Then, the health state estimation processing unit 354 estimates the most plausible state of cataracts in the examined eye E while weighting the estimation result by probability.

Next, the diagnosis support information generating unit 355 extracts the frame images for presentation from the diagnosable frame images stored in the ROM/RAM 320 (step Sb6) and generates diagnosis support information including the estimation result in step Sb5 and the frame images for presentation (step Sb8). The diagnosis support information distributing unit 356 distributes the diagnosis support information thus generated to the corresponding mobile communication terminal device 10 (step Sb9), and ends the process. As described above, the diagnosis support system 1 of this embodiment extracts diagnosable frame images from moving images captured by the mobile communication terminal device 10 equipped with the close-up imaging device 20A (that is, smart eye camera), and estimates the presence or absence of cataracts, the NS grade, the treatment method, the necessity of surgery, and the like in the examined eye E, on the basis of the diagnosable frame images. The system is then configured to generate diagnosis support information including the estimation results and distribute the information to the corresponding mobile communication terminal device 10. With this configuration, the diagnosis support system 1 of this embodiment can appropriately estimate the state of cataracts in the examined eye E and generate and make diagnosis support information available, even when the examined eye E is captured by a layperson, without the use of expensive ophthalmic diagnostic imaging device.

Further, in the diagnosis support system 1 of this embodiment, it is possible to extract only diagnosable frame images from the moving image captured by the mobile communication terminal device 10 and present the images to the annotator (physician) on the annotation terminal device 40. Accordingly, the diagnosis support system 1 of this embodiment can create teacher data and acquire diagnostic knowledge while reducing the workload of the physician when acquiring diagnostic knowledge. In particular, the diagnosis support system 1 of this embodiment is configured to acquire diagnostic knowledge by using a moving image captured by a smart eye camera. Then, because there is a high possibility that the moving image includes a plurality of diagnosable frame images, highly accurate diagnostic knowledge can be acquired even when the number of samples of the moving image data is small. It should be noted that, in the above-described embodiment, a configuration is adopted in which the CPU executing the application program realizes the functions of each unit 351 to 356 constituting the diagnosis processing unit 350 of the diagnosis support server device 30. However, naturally, it is also possible to realize the functions of each component of the diagnosis processing unit 350 by using hardware such as a field programmable gate array (FPGA) or an application specific integrated circuit (ASIC).

[A7] Modifications of First Embodiment

[A7.1] Modification 1

In the above-described first embodiment, a configuration is adopted in which the diagnosis support server device 30 extracts diagnosable frame images from the moving image data (step Sa3 in FIG. 14), transmits the extracted diagnosable frame images to the annotation terminal device 40 (step Sa4), and stores the teacher data acquired from the annotation terminal device 40 in the teacher data storage unit 333 (step Sa6). Nevertheless, the diagnosis support server device 30 may be configured to transmit the moving image data uploaded from the mobile communication terminal device 10 as is to the annotation terminal device 40 (step Sa4), acquire diagnosis result information corresponding to the diagnosis result of the physician, based on the moving image from the annotation terminal device 40 (step Sa5), and create teacher data on the basis of the diagnosis result information in the diagnosis support server device 30 to store the teacher data in the teacher data storage unit 333 (step Sa6).

In this case, the annotation terminal device 40 is configured to display a moving image capturing the examined eye E and a GUI for inputting diagnosis results on a monitor (not illustrated) on the basis of the moving image data received from the diagnosis support server device 30, and to allow the physician to input diagnosis results based on the moving image.

Further, in this case, the diagnosable frame extracting unit 352 executes the diagnosable frame image extraction process and stores all frame images classified as "Diagnosable" in the ROM/RAM 320 as diagnosable frame images. Then, the diagnostic knowledge acquiring unit 353 creates teacher data and stores the teacher data in the teacher data storage unit 333 while tagging all of the diagnosable frame images stored in the ROM/RAM 320 with the diagnosis result information acquired from the annotation terminal device 40 (step Sa6). In this way, a configuration need only be adopted in which, when the quantity of teacher data accumulated in the teacher data storage unit 333 reaches a or greater (step Sa7), the diagnostic knowledge acquiring unit 353 acquires the diagnostic knowledge (step Sa8) and stores the diagnostic knowledge in the diagnostic knowledge storage unit 334. With the configuration of this modification, it is possible to simplify the collection of samples during diagnostic knowledge acquisition and increase the number of samples, thereby improving the accuracy of the diagnostic knowledge.

[A7.2] Modification 2

In the above-described first embodiment, the annotation terminal device 40 is configured to be provided separately from the diagnosis support server device 30. However, a configuration may be adopted in which the functions of the annotation terminal device 40 are integrated into the diagnosis support server device 30 and the annotation terminal device 40 is omitted. In this case, a monitor, a keyboard, a mouse, and the like (not illustrated) are provided with the diagnosis support server device 30, allowing the physician to input the diagnosis results while the diagnosable frame images extracted by the diagnosable frame extracting unit 352 are displayed on the monitor of the diagnosis support server device 30. Then, the annotation terminal device 40 need only be configured to tag the corresponding diagnosable frame image with the diagnosis result information corresponding to the input result, and create teacher data. It should be noted that, in this case, as in Modification 1, the physician may input the diagnosis results while displaying the moving image to create the teacher data.

Further, a configuration may be adopted in which the diagnosis support server device 30 is connected to a computer (not illustrated) at an existing eye care facility, the computer at the eye care facility is utilized as the annotation terminal device 40, and the annotation terminal device 40 is omitted. In this case, data from electronic medical records may be acquired from the computer of the eye care facility and utilized as additional teacher data. By adopting this configuration, it is possible to increase the number of samples of teacher data available for diagnostic knowledge acquisition and improve the quality of diagnostic knowledge.

[A7.3] Modification 3

In the above-described first embodiment, a configuration is adopted in which the diagnosable frame extracting unit 352 applies labels of tissue names to the tissues in focus in each frame image and extracts diagnosable frame images from the frame images after the labeling. However, the diagnosable frame extracting unit 352 may be configured not to perform the labeling process. In this case, any diagnosable frame image may be extracted as the frame image for presentation in step Sb6, or the diagnosable frame image having the highest probability of being classified as "Diagnosable" may be extracted as the frame image for presentation. In addition, diagnosis support information that does not include frame images for presentation may be generated (step Sb7) and distributed.

[A7.4] Modification 4

In the above-described first embodiment, a configuration is adopted in which the presence or absence of cataracts, the NS grade, the treatment method, the necessity of surgery, and the like in the examined eye E are estimated on the basis of a two-dimensional moving image captured by the mobile communication terminal device 10. However, the diagnosable frame extracting unit 352 may be configured to construct a three-dimensional image on the basis of moving image data and estimate the state of cataracts in the examined eye E on the basis of the constructed three-dimensional image.

In a case in which a moving image of the examined eye E is captured by using the camera module of the mobile communication terminal device 10, the moving image is captured while bringing each frame image into focus by the auto-focus mechanism of the camera module. At this time, each frame image is captured in focus at a different focal length. Accordingly, each tissue in focus in each frame image is at a slightly different distance from the imaging camera lens 91 of the mobile communication terminal device 10.

In particular, in a case in which the slit light SL is used as the observation light, by making the slit light SL incident on the examined eye E from an oblique direction, it is possible to capture, while crossing the examined eye E in the cross-sectional direction with the slit light SL, a moving image that includes information related to the examined eye E in the cross-sectional direction. In this case, each tissue in focus in each frame image is at a different distance from the imaging camera lens 91. Accordingly, by layering each frame image in turn in correspondence with focal length, it is possible to construct a three-dimensional image including information related to the anterior eye tissue of the examined eye E in the cross-sectional direction. It should be noted that, in this case, it is desirable to construct the three-dimensional image by layering only the diagnosable frame images. However, it is not necessary to use only diagnosable frame images; frame images other than diagnosable frame images may also be layered to construct a three-dimensional image. Further, in this case, the diagnosable frame extracting unit 352 constitutes the "three-dimensional image construction means" of the present invention. Furthermore, in this case, light other than the slit light SL can also be used as the observation light to construct the three-dimensional image that includes information such as unevenness on the surface of the examined eye E. That is, in this modification, the observation light used for observation of the examined eye E is not limited to the slit light SL.

The three-dimensional image constructed by this method can be utilized to estimate the state of cataracts of the examined eye E, and can also be utilized as a frame image for presentation. On the other hand, in a case in which a three-dimensional image is used to estimate the health state of the examined eye E, it is necessary to utilize knowledge for estimating the state of cataracts in the examined eye E on the basis of the three-dimensional image as diagnostic knowledge.

For this reason, when this method is adopted, the diagnosable frame extracting unit 352 extracts the diagnosable frame images in step Sa3 in FIG. 14 and constructs a three-dimensional image, and stores the three-dimensional image in the ROM/RAM 320. Then, the diagnostic knowledge acquiring unit 353 transmits the three-dimensional image stored in the ROM/RAM 320 to the annotation terminal device 40 in step Sa4. On the other hand, the annotation terminal device 40 need only be configured to create teacher data by tagging the three-dimensional image with diagnosis result information on the basis of the diagnosis result of the physician, based on the three-dimensional image while displaying the received three-dimensional image, and to transmit the teacher data to the diagnosis support server device 30.

Further, in this case, when the communication control unit 310 receives the teacher data from the annotation terminal device 40 (step Sa5 in FIG. 14), the diagnostic knowledge acquiring unit 353 of the diagnosis support server device 30 stores the teacher data in the teacher data storage unit 333 (step Sa6 in FIG. 14). Each time moving image data is uploaded from the mobile communication terminal device 10, the diagnosable frame extracting unit 352 is configured to construct a three-dimensional image and sequentially accumulate the teacher data based on the constructed three-dimensional image in the teacher data storage unit 333. Then, when the teacher data quantity already stored in the teacher data storage unit 333 reaches a or greater ("Yes" in step Sa7 in FIG. 14), the diagnostic knowledge acquiring unit 353 need only be configured to execute at least one of machine learning and data mining on the basis of the teacher data stored in the teacher data storage unit 333 (that is, three-dimensional image tagged by diagnosis result information), acquire diagnostic knowledge for cataracts based on the three-dimensional image (step Sa8 in FIG. 14), and store the diagnostic knowledge in the diagnostic knowledge storage unit 334 (step Sa9 in FIG. 14).

When the diagnostic knowledge for cataracts based on the three-dimensional image is acquired and the moving image data is subsequently uploaded from the mobile communication terminal device 10 in this way, the diagnosis support information generation process is basically executed as in FIG. 15 by the diagnosis processing unit 350, and thus the diagnosis support information is generated (step Sb7 in FIG. 15) and distributed to the corresponding mobile communication terminal device 10 (step Sb8 in FIG. 15).

Further, in this case, the diagnosable frame extracting unit 352 extracts diagnosable frame images from the moving image data uploaded from the mobile communication terminal device 10 and constructs a three-dimensional image, and stores the image in the ROM/RAM 320 in the diagnosable frame image extraction process in step Sb3. Then, in step Sb5, the diagnosis support information generating unit 355 estimates the state of cataracts in the examined eye E on the basis of the diagnostic knowledge of cataracts based on the three-dimensional image stored in the diagnostic knowledge storage unit 334 and the three-dimensional image stored in the ROM/RAM 320.

Furthermore, in this case, while using the three-dimensional image stored in the ROM/RAM 320 as the frame image for presentation (step Sb6), the diagnosis support information generating unit 355 generates diagnosis support information (step Sb7) and distributes the information to the corresponding mobile communication terminal device 10 (step Sb8). As a result, the three-dimensional image is displayed on the mobile communication terminal device 10 along with the estimation results regarding the presence or absence of cataracts, the NS grade estimated value, the treatment method, and the necessity of surgery in the examined eye E, in a state viewable by the user. It should be noted that, in this case as well, the frame image for presentation may not be a three-dimensional image, and the diagnosable frame image having a largest area of a pixel region reflecting the lens tissue may be extracted and utilized. Usually, a three-dimensional image includes more information than a plane image. Accordingly, with the configuration of this modification, it is possible to improve the estimation accuracy of the state of cataracts of the examined eye E, improve the reliability of the diagnosis support information, and present diagnosis support information including the three-dimensional image to the user, and thus dramatically improve the UX of the user.

[A7.5] Modification 5

In the above-described first embodiment, a configuration is adopted in which the slit light forming member 61 and the convex lens member 93 are mounted to the close-up imaging device 20A, which constitutes a smart eye camera, the color filter member 97 is removed, and the examined eye E is captured while irradiated with the slit light SL as observation light, thereby estimating the state of cataracts in the examined eye E. In contrast, in this modification, the presence or absence of diseases other than cataracts, severities thereof, and the like are estimated.

Here, to estimate the presence or absence of diseases other than cataracts, the severities thereof, and the like in the examined eye E, it is necessary to capture a moving image including one or more diagnosable frame images that can be utilized for the diagnosis of such diseases by the smart eye camera. Accordingly, in this case, the user needs to capture a moving image of the examined eye E while changing the configuration of the close-up imaging device 20A in correspondence with disease to be estimated for severity or the like. The following specifically describes a state estimation method for each disease.

[A7.5.1] State Estimation Method for Diseases Such as Iritis and Uveitis that Develop in Anterior Chamber Tissue In a case in which the presence or absence and severities of iritis, uveitis, and the like that develop in the anterior chamber tissue of the examined eye E are estimated, it is necessary to, as in the above-described first embodiment, generate the slit light SL by the close-up imaging device 20A and, with the anterior chamber tissue of the examined eye E irradiated with the slit light SL as the observation light, condense the light including the reflected light RL of the slit light SL in the anterior chamber tissue by the convex lens member 93 on the imaging camera lens 91 to capture a moving image including one or more diagnosable frame images corresponding to these diseases. Accordingly, in this case, as in the first embodiment, it is necessary to mount the slit light forming member 61 and the convex lens member 93 onto the close-up imaging device 20A, which constitutes a smart eye camera, remove the color filter member 97, and capture a moving image of the examined eye E while configuring the close-up imaging device 20A as illustrated in FIGS. 5 to 7.

Further, in this case, the extracting knowledge storage unit 332 stores in advance the extracting knowledge for extracting diagnosable frame images corresponding to iritis and uveitis. It should be noted that, in this case, the conditions for qualifying as a diagnosable frame image are the same as those for a diagnosable frame image for cataract diagnosis except that the tissue to be irradiated with the slit light SL is not lens tissue but anterior chamber tissue.

Further, in this case, the diagnostic knowledge for iritis or uveitis is basically acquired by the same knowledge acquiring process as in FIG. 14. However, the process at this time is the same as in the above-described first embodiment except that the disease for which diagnostic knowledge is acquired is not cataracts but iritis or uveitis, and thus details thereof will be omitted.

Then, when moving image data is uploaded from the mobile communication terminal device 10 with the diagnostic knowledge for iritis or uveitis stored in the diagnostic knowledge storage unit 334, the diagnosis support information is basically generated by the same diagnosis support information generation process as in FIG. 15 in the diagnosis processing unit 350 (step Sb7), and distributed to the corresponding mobile communication terminal device 10 (step Sb8). It should be noted that the process at this time is the same as in the above-described first embodiment except that the target disease is not cataracts but iritis or uveitis, as in the diagnostic knowledge acquiring process.

[A7.5.2] State Estimation Method for Diseases Such as Chalazion and Hordeolum that Develop in Eyelid Tissue, and Allergic Conjunctivitis, Epidemic Keratoconjunctivitis, Conical Cornea, and Corneal Opacity that Develop in Corneal and Conjunctival Tissue When estimating the presence or absence and severity of diseases such as chalazion and hordeolum that develop in eyelid tissue, and allergic conjunctivitis, epidemic keratoconjunctivitis, conical cornea, and corneal opacity that develop in corneal and conjunctival tissue, moving images including diagnosable frame images corresponding to these diseases must be captured with a smart eye camera. Here, there are two methods of capturing a moving image including diagnosable frame images corresponding to these diseases, as follows.

<Imaging Method 1>

This imaging method is a method of capturing a moving image of the examined eye E while irradiating the examined eye E with the slit light SL as the observation light while configuring the close-up imaging device 20A, which constitutes a smart eye camera, in the same manner as in the above-described first embodiment (FIGS. 5 to 7).

<Imaging Method 2>

This imaging method is a method of capturing a moving image of the examined eye E with the examined eye E irradiated with white diffused light as the observation light by mounting the convex lens member 93 onto the close-up imaging device 20A, which constitutes a smart eye camera, removing the color filter member 97 and slit light forming member 61, and creating a state in which the light-source light (white diffused light) emitted from the light source 92 passes through the holes 88, 95 as is and is irradiated in the front direction.

However, in this case, the conditions for qualifying as a diagnosable frame image differ between a case in which imaging method 1 is adopted and a case in which imaging method 2 is adopted. The conditions in a case in which imaging method 1 is adopted are basically the same as in the cataract case, but the irradiation target of the slit light SL is tissue other than the lens, such as the eyelid or eye surface. In contrast, the condition in a case in which imaging method 2 is adopted is a frame image in focus reflecting the reflected light RL of the white diffused light along with at least portion of the tissue to be observed irradiated with the white diffused light as the observation light.

Accordingly, in a case in which the states of these diseases are estimated, the imaging method to be utilized is determined in advance and extracting knowledge corresponding to the imaging method is stored in the extracting knowledge storage unit 332. It should be noted that, a configuration can also be adopted in which a plurality of sets of extracting knowledge corresponding to each imaging method are stored in the extracting knowledge storage unit 332 in advance, and the extracting knowledge utilized is switched to extract diagnosable frame images in correspondence with the imaging method selected by the user. In this case, the user specifies the imaging method to be utilized on the diagnostic app, thereby uploading the information indicating the imaging method along with the moving image data from the mobile communication terminal device 10. Then, in the diagnosable frame image extraction process, the diagnosable frame extracting unit 352 need only be configured to extract diagnosable frame images while switching the extracting knowledge to be utilized on the basis of the information.

Further, in this case, the diagnostic knowledge corresponding to these diseases is basically acquired by the same diagnostic knowledge acquiring process as in FIG. 14, regardless of which imaging method is adapted. The process at this time is similar to that in the above-described first embodiment except that the diseases for which diagnostic knowledge is acquired are not cataracts but chalazion and hordeolum, allergic conjunctivitis, epidemic keratoconjunctivitis, conical cornea, and corneal opacity, and the like that develop in corneal and conjunctival tissue, and thus details thereof will be omitted.

Then, when moving image data is uploaded from the mobile communication terminal device 10 with the diagnostic knowledge for these diseases stored in the diagnostic knowledge storage unit 334, the diagnosis processing unit 350 basically generates diagnosis support information by the same diagnosis support information generation process as in FIG. 15 (step Sb7), and distributes the information to the corresponding mobile communication terminal device 10 (step Sb8). It should be noted that the process at this time is the same as in the above-described first embodiment except that the target disease is not cataracts, but chalazion, hordeolum, allergic conjunctivitis, epidemic keratoconjunctivitis, conical cornea, corneal opacity, or the like as in the diagnostic knowledge acquiring process.

Further, when this configuration is adopted, the moving image captured by the smart eye camera may include diagnosable frame images that can be utilized to diagnose a plurality of diseases. At this time, the user may specify the targeted diseases in the mobile communication terminal device 10 or estimate the states of the plurality of diseases at once. It should be noted that the method of estimating states of a plurality of diseases at once is described in detail in the section of Modification 6.

[A7.5.3] State Estimation Method for Diseases Such as Superficial Punctate Keratitis and Corneal Ulcers In a case in which the presence or absence of diseases such as superficial punctate keratitis and corneal ulcers and the severities thereof are estimated, it is necessary to capture a moving image including frame images that can diagnose the state of an injury that occurred on the cornea with a smart eye camera. For this reason, in this case, the color filter member 97 and the convex lens member 93 constituted by a blue free filter for vital staining examination are mounted to the close-up imaging device 20A constituting a smart eye camera, and the slit light formation member 61 is removed, thereby configuring the close-up imaging device 20A as illustrated in FIG. 3B. Then, the light-source light emitted from the light source 92 is changed to blue light by the color filter member 97, and a moving image of the examined eye E is captured with the examined eye E irradiated with the blue light as the observation light. Further, at this time, a contrast-enhancing fluorescein solution is administered to the examined eye E, thereby changing a color of the injury that occurred on the cornea and conjunctiva to green, and the green light is received by an image sensor through the imaging camera lens 91, thereby capturing the injury that occurred on the cornea and conjunctiva of the examined eye E.

Then, in this case, the extracting knowledge storage unit 332 stores in advance the extracting knowledge for extracting diagnosable frame images that can be utilized for diagnosis of diseases such as superficial punctate keratitis and corneal ulcers. It should be noted that, in this case, the condition for qualifying as a diagnosable frame image is a frame image in focus reflecting the reflected light RL of the blue light in the tissue to be observed along with at least a portion of the tissue to be observed irradiated with the blue light as the observation light. Accordingly, in this case, it is necessary to store in advance the extracting knowledge for extracting frame images that satisfy the conditions in the extracting knowledge storage unit 332.

Further, in this case, the diagnostic knowledge corresponding to diseases such as superficial punctate keratitis and corneal ulcers is basically acquired by the same diagnostic knowledge acquiring process as in FIG. 14. However, the process at this time is the same as in the above-described first embodiment except that the disease for which diagnostic knowledge is acquired is not cataracts, but superficial punctate keratitis, corneal ulcers, or the like.

Then, when moving image data is uploaded from the mobile communication terminal device 10 with the diagnostic knowledge for diseases such as superficial punctate keratitis and corneal ulcers stored in the diagnostic knowledge storage unit 334, the diagnosis processing unit 350 basically generates diagnosis support information by the same diagnosis support information generation process as in FIG. 15 (step Sb7), and distributes the information to the corresponding mobile communication terminal device 10 (step Sb8). It should be noted that the process at this time is the same as in the above-described first embodiment except that the target disease is not cataracts, but diseases such as superficial punctate keratitis and corneal ulcers, as in the diagnostic knowledge acquiring process. Further, in this case as well, the moving image captured by the smart eye camera may include diagnosable frame images that can be utilized to diagnose a plurality of diseases. At this time, the user may specify the targeted diseases in the mobile communication terminal device 10 or estimate the states of the plurality of diseases at once.

[A7.5.4] State Estimation Method for Dry Eye Disease (DED)

In a case in which the state of DED in the examined eye E is estimated, it is necessary to observe the state of the injury that occurred on the cornea and conjunctiva and the state of tears on the eye surface. For this reason, in this case, the color filter member 97 constituted by a blue free filter for vital staining examination and the convex lens member 93 are attached to the close-up imaging device 20A, which constitutes a smart eye camera, as when estimating the state of the above-described superficial punctate keratitis or the like, the light-source light emitted from the light source 92 is changed to blue light by the color filter member 97, and the tissue to be observed in the examined eye E is captured with the examined eye E irradiated with the blue light as the observation light. Further, in this case, it is also necessary to capture the eye surface, the cornea, and the conjunctiva of the examined eye E while contrasting the injury by administering fluorescein solution eyedrops into the examined eye E.

[A7.5.4.1] Verification Results of DED Diagnosis Using Smart Eye Camera

To verify whether a smart eye camera with the above-described configuration can diagnose DED, the inventors conducted observations with the mobile communication terminal device 10 (smartphone) equipped with the close-up imaging device 20A provided with the convex lens member 93 and the color filter member 97, and compared the results with those of existing devices for DED observation. It should be noted that, in this verification, the device used as the close-up imaging device 20A was a device having the same configuration as that designed for the iPhone 7 (registered trademark) utilized in the above-described verification of cataracts, with a color filter member 97 constituted by a blue filter made of acrylic resin (PGZ 302K 302, manufactured by Kuraray Co., Ltd.) mounted thereto.

Further, in this verification, as Verification Example 1, images respectively captured by the mobile communication terminal device 10 equipped with the close-up imaging device 20A for verification and the existing device in a DED mouse model related to graft-versus-host disease (GVHD) were compared, and an eye examination, including tear film break-up time (TFBUT) of the mouse model, was conducted. Furthermore, in Verification Example 2, TFBUT measurements, which are diagnostic criteria for DED, were performed on a total of 42 patients including patients with DED and normal patients without DED. It should be noted that TFBUT is an essential parameter used in the diagnosis of DED.

Verification Example 1

DED is caused by a decrease in tear volume, rapid collapse of the tear film, and an increase in tear evaporation, and TFBUT is one of the core mechanisms of DED. Although the DED mouse model has been studied in past DED research, a method of measuring TFBUT in humans has not been established with the DED mouse model. There are several reasons why TFBUT evaluation in a mouse model cannot be applied to humans as is. First, a width of the cornea of a mouse is only 2 to 3 mm and the size is so small, and thus it is difficult to adjust the focus for human application. Second, an existing slit-lamp microscope for eye clinics is used for an examination of the anterior eye (tissues of the eyelid, eye surface, cornea, conjunctiva, anterior chamber, and lens), but the device is so large, and thus cannot be easily moved and does not have an image recording function. Third, the existing slit-lamp microscopes are expensive and have low cost effectiveness. To avoid these problems, usage of tear secretion (TS) and corneal fluorescein score (CFS) for diagnosis in the DED mouse model has increased. Nevertheless, in such a DED mouse model as well, a device easily applicable to humans has not yet been established.

Figures 16, 17A, 17B:
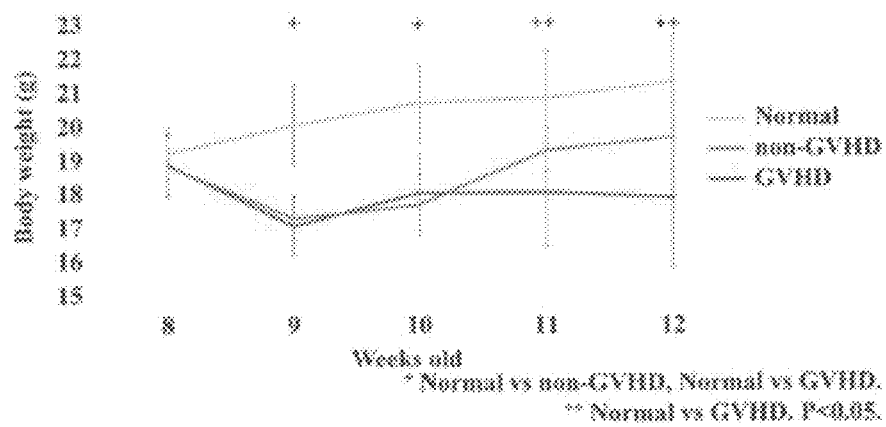
FIG. 16 shows, in the upper row, representative photographs of an eye exposed to white light and, in the lower row, representative photographs of fluorescein staining. The images in the left column are examples of an eye captured with an existing device, and the images in the right column are examples of an eye captured using a smart eye camera.
FIG. 17A is a graph showing results obtained by measuring a relationship between age (weeks old) and body weight of mice.
FIG. 17B is a table showing progress of body weight by group.

For Verification Example 1, FIG. 16 shows images captured by the mobile communication terminal device 10 equipped with the close-up imaging device 20A having the above-described configuration (smart eye camera) having the above-described configuration. It should be noted that FIG. 16 shows, in the upper row, representative photographs of an eye exposed to white light and, in the lower row, representative photographs of fluorescein staining. In FIG. 16, the images in the left column are examples captured with an existing device, and the images in the right column are examples captured using the mobile communication terminal device 10 equipped with the close-up imaging device 20A having the above-described configuration. It should be noted that, as the existing device, a device widely used for evaluating the eye of the DED mouse model was used. Specifically, a device configured by a microscope (product name: SZ61), a camera (product name: DP70), and a light source (product name: LG-PS2) manufactured by Olympus Corporation was used and, as the existing device for comparison in Verification Example 2, a portable slit-lamp microscope (product name: SL-15, Kowa Co., Ltd.) was used.

(Mouse GVHD Group-Related DED Model)

For the DED mouse model, the method by Zhang for reproducing the GVHD group-related DED phenotype was selected, similar to the clinical example. The used B10.D2 and BALB/cCrSlc (BALB/c) mice (7 weeks old) were purchased from Sankyo Research Laboratories (Tokyo, Japan). After being adapted to a specific pathogen free (SPF) environment for one week, the mice were divided into three groups (five mice per group). For the DED (GVHD group model) group, allogeneic bone marrow transplantation (BMT) was performed by using 8-week-old male B10.D2 and female BALB/c mice for the donors and recipients. For the negative control (non-GVHD group), syngeneic BMT was performed by transplanting donor cells from male BALB/c mice to female BALB/c mice. Six hours prior to BMT, these recipient mice were irradiated with 700 cGy using a Gammacel 137Cs source (Hitachi Medico Ltd.) and then donor cells were injected via tail vein injection. For a healthy control (normal group control), female BALB/c mice of the same age were selected.

Three mouse models (GVHD group, non-GVHD group, and normal group control) were used for comparison. The DED phenotype in this DED mouse model appears three weeks after BMT, and thus eyeball phenotypes of body weight, TFBUT, corneal fluorescein score (CFS), TS, and the like were collected once a week, from before BMT (8 weeks old) to 12 weeks old. It should be noted that all imaging data recorded by the smart eye camera were manually transferred to an iMac (Apple Inc., U.S.A.) via Bluetooth (registered trademark) and converted to mp4 video data for safe storage.

(Evaluation of Tear Film Break-Up Time)

Stability was measured by using tear film break-up time (TFBUT). An observer gripped the mouse with one hand and then injected 1 µL of 0.5% fluorescein sodium into the conjunctival sac using a micropipette. After three eye drops, the observer used the mobile communication terminal device 10 equipped with the above-described close-up imaging device 20A with the right hand to capture an image of the eye. To compare this new method with the existing method, the TFBUT acquired with the existing device was evaluated by a conventional method.

(Evaluation of Corneal Fluorescein Score)

Corneal epithelial wound was evaluated by using the corneal fluorescein score (CFS) evaluated 90 seconds after administration of eyedrops of fluorescein. Each cornea was divided into four quadrants and then recorded individually. The CFS was calculated by using a four-grade evaluation. An evaluation 1 included slightly dotted staining with "<30 spots," an evaluation 2 included dotted staining with ">30 spots" without dispersed, an evaluation 3 included severe diffuse staining, but no positive plaques, and an evaluation 4 included fluorescein positive plaques.

(Evaluation of Tear Secretion)

Tear secretion (TS) was measured by using a modified Schirmer test. Phenol red thread was placed on a temporal side of an upper eyelid margin for 15 seconds. A length of a wet portion from the end was within 0.5 mm.

(Data Analysis)

Data analysis was performed with Prism software (Mac version 6.04; GraphPad Software, Inc., U.S.A.). The D'Agostino-Pearson omnibus normality test was used to evaluate whether the data exhibited a normal distribution. The Mann-Whitney U test was used to compare the differences between normal and objective (GVHD group and non-GVHD group) in several parameters including body weight, TFBUT, CFS, and TS. The Wilcoxon signed-rank test was used to compare the differences between the results evaluated by the existing method and the smart eye camera. Friedman test was used to compare the differences in TFBUT evaluations by three different eye specialists, captured with the smart eye camera. Lin's concordance correlation coefficient was used to evaluate the possible correlation between TFBUT and CFS using the existing technique and the smart eye camera. Data were expressed as the mean±standard deviation (SD), and P values less than 0.05 were regarded as statistically significant.

Results (Body Weight)

FIG. 17A is a graph showing results obtained by measuring a relationship between age (weeks old) and body weight of mice, and FIG. 17B is a table showing progress of the body weight by group (green: normal group, blue: non-GVHD group, red: GVHD group). To verify the applicability of the smart eye camera in a mouse model of mice, bone marrow transplantation (BMT) was first evaluated. Based on the results of FIGS. 17A and 17B, the body weight of the mice was initially adjusted for each group, and therefore there was no difference in body weight between the normal group, the non-GVHD group, and the GVHD group before BMT (8 weeks old). Nevertheless, in the 9- and 10-week-old non-GVHD group and GVHD group, the body weights were significantly reduced compared to the normal group. As a result, the body weights were P=0.016 and 0.016 at 9 weeks old, and P=0.016 and 0.032 for the normal group vs. the non-GVHD group and the normal group vs. the GVHD group, respectively, at 10 weeks old. The body weights were P=0.032 and 0.032 for the GVHD group at 11 and 12 weeks old, respectively, when compared to the body weights for the normal group at 11 and 12 weeks old, and reduced only in the GVHD group.

(Volume of Tear Secretion)

FIG. 18A is a graph showing results obtained by measuring a relationship between age (weeks old) and tear secretion (TS) volume of mice, and FIG. 18B is a table showing progress of continuing tear secretion (TS) by group (green: normal group, blue: non-GVHD group, red: GVHD group). Significant differences in TS were observed between the normal group and the non-GVHD group and between the normal group and the GVHD group, at 9 to 12 weeks old. Furthermore, at 12 weeks old, TS was significantly shorter in the GVHD group compared to the non-GVHD group. Given N=5 per group, the evaluation of significance (P<0.05) was performed by the Mann-Whitney U test.

Based on the results in FIGS. 18A and 18B, while there was no difference in TS before BMT for body weight, these values were significantly reduced in the non-GVHD group and the GVHD group compared to the normal group at 9 to 12 weeks old. The normal group vs. the non-GVHD group and the normal group vs. the GVHD group were P=0.008 and 0.016 at 9 weeks old, P=0.008 and 0.008 at 10 weeks old, P=0.016 and 0.024 at 11 weeks old, and P=0.008 and 0.008 at 12 weeks old, respectively. Further, the TS volume in the GVHD group at 12 weeks old was 1.65±1.01, which was significantly low compared to the 3.70±0.33 of the non-GVHD group. Furthermore, the non-GVHD group vs. the GVHD group at that time was P=0.008.

(Tear Film Break-Up Time)

FIG. 19A is a graph showing results obtained by measuring a relationship between age (weeks old) and tear film break-up time (TFBUT) of mice, and FIG. 19B is a table showing progress of TFBUT by group (green: normal group, blue: non-GVHD group, red: GVHD group). Significant difference was obtained by using the Mann-Whitney U test given n=5 per group and P<0.05 as significant. TFBUT was evaluated by using the right eye.

For TFBUT, no difference was observed between the normal group, the non-GVHD group, and the GVHD group before BMT (8 weeks old). Nevertheless, TFBUT was significantly reduced in the GVHD group (P=0.024, 0.008, and 0.008 at 10, 11, and 12 weeks old, respectively) when compared to the normal group at 10 to 12 weeks old. TFBUT was reduced in the non-GVHD group as well when compared to the normal group at 11 weeks old (normal group vs. non-GVHD group was 5.80±0.84 vs 4.00±0.71, P=0.024). Furthermore, the GVHD group had a significantly shorter TFBUT than the non-GVHD group (P=0.040 and 0.008 at 11 and 12 weeks old, respectively) at 11 and 12 weeks old when compared to the post-BMT group.

FIG. 20 shows continuous tear film photographs stained by a fluorescein solution. Thus, breakup of the tear film was observed. FIG. 20 shows, in the upper row, examples of the GVHD group in which the tear film was broken in 3 seconds (TFBUT=3 seconds) and, in the lower row, examples of the normal group in which the tear film was stabilized in 3 seconds and collapsed in 6 seconds (TFBUT=6 seconds). The photographs show the right eyes of 12-week-old female BALB/c mice. These results show that the smart eye camera can evaluate continuous TFBUT of the GVHD group DED mouse model.

(Continuous Corneal Fluorescein Score)

FIG. 21A is a graph showing results obtained by measuring a relationship between age (weeks old) and continuous corneal fluorescein score (CFS) of mice, and FIG. 21B is a table showing progress of CFS by group (green: normal group, blue: non-GVHD group, red: GVHD group). Significant difference was obtained by using the Mann-Whitney U test given n=5 per group and P<0.05 as significant. CFS was evaluated by using the right eye.

When compared with the normal group at 9, 11, and 12 weeks old, a significant difference was observed in the GVHD group (P=0.008, 0.008, and 0.032, respectively), as shown in FIG. 21B. While the non-GVHD group tended to have a higher CFS than the normal group, and the GVHD group tended to have a higher CFS than the non-GVHD group, these differences did not reach statistical significance (all P>0.05). From this result, it was confirmed that continuous CFS can also be evaluated by the smart eye camera in the DED mouse model of the GVHD group.

(Comparison with Existing Device)

FIGS. 22A to 22C show results of comparing measurement results of the TFBUTs and CFSs of the smart eye camera and the existing technique, FIG. 22A being a graph of TFBUT and FIG. 22B being a graph of CFS, and green indicating normal group, blue indicating non-GVHD group, and red indicating GVHD group. FIG. 21C is a table summarizing these results. Significant difference was obtained by using the Mann-Whitney U test given n=5 per group and P<0.05 as significant.

In each graph, two bars are aligned. From this result, it is understood that there is no significant difference between the use of the existing device and the smart eye camera in ordinary non-GVHD groups and GVHD groups. Then, for TFBUT, based on the results obtained by the smart eye camera and the portable slit-lamp microscope (existing device), there was no significant difference between the normal group control, the non-GVHD group, and the GVHD group (0.50, 0.99, and 0.99, respectively, and all P>0.05). Similarly, for CFS, based on the results obtained by the smart eye camera and the existing slit lamp microscope, significant differences were not found between the normal group control, the non-GVHD group, and the GVHD group (P=0.99, 0.75, and 0.50, respectively, and all P>0.05).

FIGS. 23A and 23B are graphs showing a correlation between the smart eye camera and the existing device, FIG. 23A being a graph of TFBUT and FIG. 23B being a graph of CFS. In each graph, the Y axis indicates the numerical value evaluated by the smart eye camera, and the X axis indicates the evaluation by the existing device. n is 15. A high correlation was observed in TFBUT (R=0.868, 95%, CI: 0.656 to 0.953) and CFS (R=0.934, 95%, CI: 0.823 to 0.976).

Based on the result of FIG. 23A, the TFBUTs of the smart eye camera and the existing device were P<0.001 and r=0.871, exhibiting a significant correlation. Further, based on the result of FIG. 23B, the CFSs of the smart eye camera and the existing device were also P<0.001 and r=0.941, exhibiting a significant correlation. These results show that, compared to the existing device, the smart eye camera has the same quality as when the eyeball phenotypes of the mouse model are adapted.

(Conclusion)

From the above verification example, it could be verified that the mobile communication terminal device 10 equipped with the close-up imaging device 20A (that is, smart eye camera) of the first embodiment is applicable in the DED mouse model. This model was characterized by body weight loss, shortening of TS, and worsening of the corneal epithelitis, and these characteristics were reflected in the CFS. FIGS. 24A to 24D are graphs summarizing these. Based on the results, the TFBUT of the GVHD group in the DED mouse model was reduced compared to the normal group and the non-GVHD group. As shown in FIGS. 24A to 24D, this exhibits that the TFBUT trend is similar to the TS trend and opposite to the CFS trend.

As shown in FIGS. 22A to 22C, there was no difference in observation results between the smart eye camera and the existing device for both TFBUT and CFS. Further, as understood from the correlation analysis shown in FIGS. 23A and 23B, the results obtained by the smart eye camera and the existing device exhibited a significantly high correlation for both TFBUT and CFS. These mean that the results captured with the smart eye camera have the same quality as the results captured with the existing device. Furthermore, although not illustrated, similar results were obtained by different observers as well.

Verification Example 2

Figure 24A:
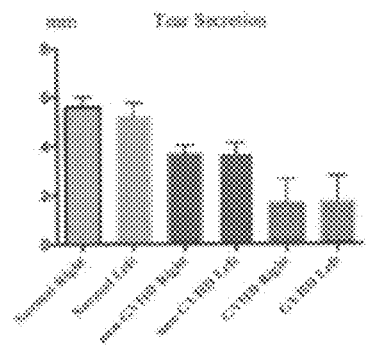
FIGS. 24A to 24D are graphs summarizing body weight loss, shortening of TS, and worsening of corneal epithelitis, FIG. 24A showing TS, FIG. 24B showing TFBUT, FIG. 24C showing CFS, and FIG. 24D being a table summarizing these.
Figure 24B:
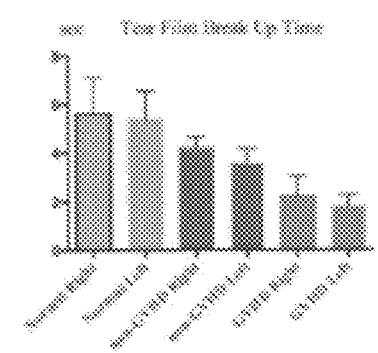
Figure 24C:
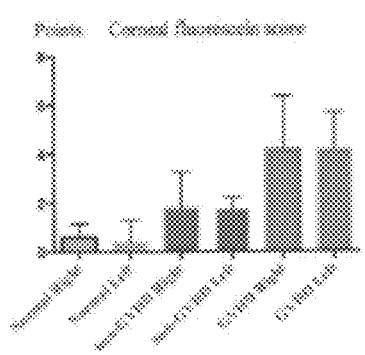
Figures 24D, 25:
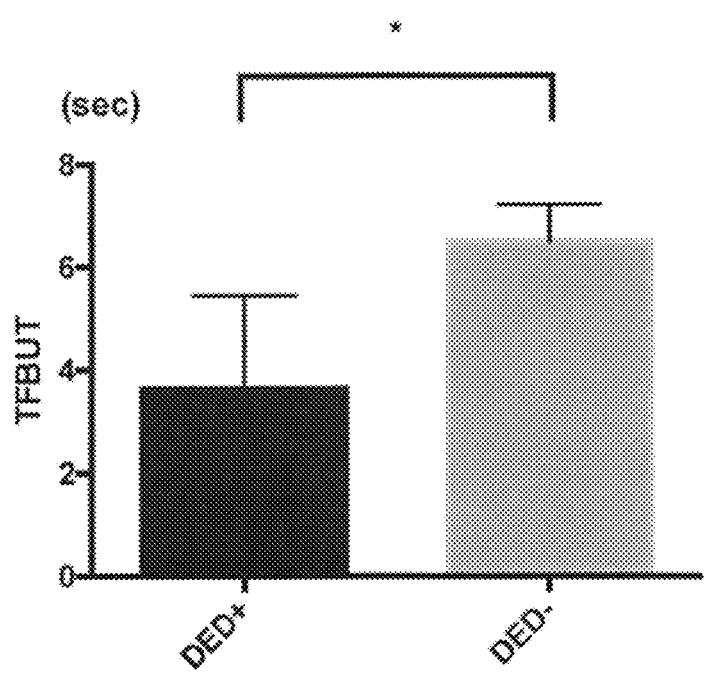
FIG. 25 shows TFBUT measurement results, which are diagnostic criteria for dry eye, for a total of 42 patients including patients with dry eye and normal patients without dry eye.

In Verification Example 2, TFBUT measurements, which are diagnostic criteria for dry eye, were performed on a total of 42 patients including patients with dry eye and normal patients without dry eye using the mobile communication terminal device 10 equipped with the close-up imaging device 20A having the above-described configuration (smart eye camera), and a left-right difference, imaging seconds, and the like were also verified. The results are shown in FIG. 25. The TFBUT of the dry eye patient group (represented by "DED+") was 3.64±1.81 seconds, and the TFBUT of the normal patients without dry eye (represented by "DED-") was 6.50±0.71 seconds. Statistically significantly, the dry eye group resulted in a shorter TFBUT. A significant difference was obtained by using the Mann-Whitney U test with $P<0.05$ as significant. From this, it can be said that the smart eye camera is capable of evaluating eye findings such as TFBUT.

As described above, it was confirmed that, according to the mobile communication terminal device 10 equipped with the close-up imaging device 20A (that is, smart eye camera) of this embodiment, it is possible to evaluate continuous eye phenotypes such as TFBUT and CFS.

(Acquisition Method of Diagnostic Knowledge Corresponding to DED)

In a case in which the state of DED in the examined eye E is actually estimated, it is necessary to store in advance the extracting knowledge for extracting diagnosable frame images that can be utilized for the diagnosis of DED in the extracting knowledge storage unit 332, and store the diagnostic knowledge corresponding to DED in the diagnostic knowledge storage unit 334.

Here, to diagnose DED in the examined eye E, it is necessary to irradiate the tissue to be observed (cornea, conjunctiva, or eye surface) with blue light as the observation light, and extract a frame image in focus reflecting at least a portion of the tissue to be observed along with the reflected light RL as a diagnosable frame image for CFS scoring. For this reason, in this case, it is necessary to store in advance the extracting knowledge for extracting frame images that satisfy the conditions in the extracting knowledge storage unit 332.

Further, in a case in which the state of DED in the examined eye E is estimated, it is necessary to estimate the state of DED while measuring continuous CFS, TS, and TFBUT on the basis of changes over time in the diagnosable frame images. Then, in a case in which these are measured, it is necessary to observe the state of tear secretion in the eye surface, corneal epithelium, and conjunctival epithelium of the examined eye E and the state of change in the tear film over time. For this reason, in a case in which the state of DED in the examined eye E is estimated, state estimation based on a single still frame image as in each of the above-described disease cases is difficult.

Therefore, in a case in which the state of DED in the examined eye E is estimated, in step Sa3 of the diagnostic knowledge acquiring process (FIG. 14), the diagnosable frame extracting unit 352 extracts, from the frame images classified as "Diagnosable," the frame image captured at the earliest timing in terms of time as the diagnosable frame image corresponding to "0" seconds, and stores the diagnosable frame image in the ROM/RAM 320 in association with the time information (0 seconds). Further, at this time, the diagnosable frame extracting unit 352 extracts, from the frame images captured at timings after predetermined times elapse from the diagnosable frame image corresponding to "0" seconds (frame images captured at each timing after 3 seconds and after 6 seconds, for example), the frame images classified as "Diagnosable" as the diagnosable frame images at those timings, and stores each of the diagnosable frame images in the ROM/RAM 320 in association with the corresponding time information (3 seconds, 6 seconds, and the like, for example). Then, in step Sa4, the diagnostic knowledge acquiring unit 353 is configured to transmit each diagnosable frame image stored in the ROM/RAM 320 in association with the time information to the annotation terminal device 40.

When the diagnosable frame images associated with time information are received from the diagnosis support server device 30 in this way, the annotation terminal device 40 displays each diagnosable frame image, in chronological order while associating the images with the time information, such as, for example, the diagnosable frame image at 0 seconds, the diagnosable frame image at 3 seconds, and the diagnosable frame image at 6 seconds, and displays the diagnosable frame images on a monitor so that the physician can check the state of tears and the state of change in the tear film in the examined eye E.

Then, when the physician measures continuous CFS, TS, and TFBUT on the basis of the diagnosable frame images displayed in association with the time information, and inputs diagnosis results, such as the presence or absence of DED and the severity thereof, the annotation terminal device 40 generates a change image (a kind of moving image) composed of a plurality of diagnosable frame images by arranging each diagnosable frame image in chronological order on the basis of the time information. Then, the annotation terminal device 40 allows the physician, who is the annotator, to diagnose DED while displaying the change image, creates teacher data by tagging the change image with diagnosis result information, and transmits the teacher data to the diagnosis support server device 30. As a result, the teacher data storage unit 333 of the diagnosis support server device 30 stores the teacher data related to the change image (step Sa6). It should be noted that, at this time, the physician who is the annotator may measure the TFBUT on the basis of the change image and, if the measured value of TFBUT is below a predetermined threshold (5 seconds or less, for example), diagnose DED as being present.

Each time moving image data is uploaded from the mobile communication terminal device 10, the process described above is repeated and, when the quantity of teacher data related to the change image accumulated in the teacher data storage unit 333 reaches a or greater, the diagnostic knowledge acquiring unit 353 acquires the diagnostic knowledge corresponding to DED on the basis of the teacher data accumulated in the teacher data storage unit 333 (step Sa8) and stores the diagnostic knowledge in the diagnostic knowledge storage unit 334 (step Sa9). At this time, the diagnostic knowledge acquiring unit 353 need only execute at least one of machine learning and data mining to acquire the diagnostic knowledge corresponding to the DED on the basis of the change image included in the teacher data and the diagnosis result information. It should be noted that the generation timing of the change image is not limited to the above-described generation timing, and the image can be generated by the diagnostic knowledge acquiring unit 353 when the diagnosable frame images and time information are transmitted to the annotation terminal device 40. Further, in the diagnosable frame image extraction process, the diagnosable frame extracting unit 352 may be configured to generate the change image.

On the other hand, when moving image data is uploaded from the mobile communication terminal device 10 with the diagnostic knowledge corresponding to DED stored in the diagnostic knowledge storage unit 334, the diagnosis processing unit 350 basically generates diagnosis support information by the same diagnosis support information generation process as in FIG. 15 (step Sb7), and distributes the information to the corresponding mobile communication terminal device 10 (step Sb8).

However, in this case, it is necessary to estimate the state of DED in the examined eye E by using a change image similar to the change image obtained in the above-described diagnostic knowledge acquiring process (change image composed of diagnosable frame images at 0 seconds, 3 seconds, and 6 seconds, or the like, for example). For this reason, in this case, the diagnosable frame extracting unit 352 extracts diagnosable frame images obtained at the same timing as the timing at which the diagnosable frame images were extracted in the diagnostic knowledge acquiring process in step Sb3 (diagnosable frame images obtained at each timing of 0 seconds, 3 seconds, and 6 seconds, for example) and stores the images in the ROM/RAM 320 while associating the images with time information.

Further, in this case, the health state estimation processing unit 354 generates the change image by arranging the diagnosable frame images stored in the ROM/RAM 320 in the health state estimating process in step Sb5 in chronological order on the basis of the time information, and estimates the state of DED in the examined eye E on the basis of the change image and the diagnostic knowledge for DED stored in the diagnostic knowledge storage unit 334. It should be noted that, in this case, whether or not the health state estimation processing unit 354 estimates the most plausible state of DED by weighting the estimation results on the basis of the probability of being classified as "Diagnosable" is as desired. For example, in a case in which weighting is performed, when diagnosable frame images are extracted in step Sb3, a plurality of sets of images, for example, 5 images corresponding to "0-second timing," 5-images corresponding to "3-second timing," and 5 images corresponding to "6-second timing," are extracted as diagnosable frame images for generating change images. Then, the diagnosis processing unit 350 generates a change image for each set and estimates the state of DED for each change image. Then, the estimation results need only be weighted by the probability of being classified as "Diagnosable" for each change image to estimate the most plausible state of DED in the examined eye E. It should be noted that, in this case, the method of calculating the probability of each change image being classified as "Diagnosable" is as desired. For example, the average value of the probabilities of the diagnosable frame images constituting each change image being classified as "Diagnosable" may be used.

Then, in step Sb6, the diagnosis support information generating unit 355, while using the change image generated in step Sb5 as the frame image for presentation, generates diagnosis support information including the change image and the DED estimation result (step Sb7), and distributes the information to the corresponding mobile communication terminal device 10 (step Sb8). It should be noted that although, in this modification, a case is described in which a change image is generated while extracting the diagnosable frame images corresponding to 0 seconds, 3 seconds, and 6 seconds as an example, a method of extracting the first diagnosable frame image in the moving image data uploaded from the smart eye camera as 0 seconds, then extracting all diagnosable frame images included in the moving image captured in the following 10 seconds to connect these, and generating a change image (a kind of moving image) of 10 seconds may be adopted.

[A7.6] Modification 6

In the above-described first embodiment and each modification, a configuration is adopted in which one disease (cataracts or the like, for example) in the anterior eye of the examined eye E is targeted, and the state of the disease is estimated on the basis of a moving image captured by the mobile communication terminal device 10. Nevertheless, actual patients may suffer from a plurality of diseases, such as cataracts and epidemic keratoconjunctivitis, for example, at the same time. Accordingly, it is desirable to estimate and make the states of a plurality of disease available at once by capturing a single moving image.

Therefore, in this modification, a configuration is adopted in which the extracting knowledge corresponding to a plurality of diseases is stored in advance in the extracting knowledge storage unit 332, the diagnostic knowledge corresponding to the plurality of diseases is stored in the diagnostic knowledge storage unit 334 and, when moving image data is uploaded from the mobile communication terminal device 10, the presence or absence of the disease, the severity thereof, and the like in the examined eye E are estimated for each disease on the basis of the moving image data, and the diagnosis support information including the estimation results for each disease is generated (step Sb7) and distributed to the corresponding mobile communication terminal device 10 (step Sb8). It should be noted that, as for the method of observing and capturing the anterior eye of the examined eye E, there are three methods including, as described above, (method 1) a method of irradiating the examined eye E with the slit light SL as the observation light and observing and capturing the examined eye E using the close-up imaging device 20A with the slit light forming member 61 and the convex lens member 93 mounted thereto and the color filter member 97 removed therefrom, (method 2) a method of irradiating the examined eye E with white diffused light as the observation light and observing and capturing the examined eye E by the convex lens member 93 only being mounted thereto, and (method 3) a method of irradiating the examined eye E with blue light as the observation light and observing and capturing the examined eye E using the close-up imaging device 20A with the color filter member 97 and convex lens member 93 mounted thereto. In this modification, a moving image captured by any of these methods is used.

At this time, the diagnosis processing unit 350 basically generates diagnosis support information by executing the same diagnosis support information generation process as in FIG. 15. However, in this modification, it is necessary to enable estimation of the states related to plurality of diseases at once, and thus the following method is adopted.

First, in the diagnosable frame image extraction process in step Sb3, the diagnosable frame extracting unit 352 extracts diagnosable frame images for each disease on the basis of each frame image included in the moving image data and the extracting knowledge corresponding to each disease. At this time, the diagnosable frame extracting unit 352 extracts the frame images in which the tissue that develops the target disease is in focus while labeling the tissue in focus in each frame image included in the moving image data. Then, the diagnosable frame extracting unit 352 extracts diagnosable frame images for each disease on the basis of the extracting knowledge from the extracted frame images. At this time, the diagnosable frame extracting unit 352 calculates the probability of each of the extracted frame images being classified as the "Diagnosable," and stores the calculated probability and the corresponding disease name in the ROM/RAM 320 in association with the diagnosable frame image.

Then, in this modification, the health state estimation processing unit 354 reads the diagnostic knowledge corresponding to the disease from the diagnostic knowledge storage unit 334 on the basis of the disease name stored in association with the diagnosable frame image extracted in step Sb3 (step Sb4), and estimates the state for each disease (step Sb5). At this time, the health state estimation processing unit 354 estimates the state of the disease corresponding to each diagnosable frame image stored in the ROM/RAM 320. Then, the most plausible state of each disease in the examined eye E is estimated while weighting the estimation results by the probability of being classified as "Diagnosable" stored in association with the diagnosable frame image. It should be noted that the process for estimating the most plausible state of each disease is the same as in the above-described first embodiment.

Further, in step Sb6, the diagnosis support information generating unit 355 extracts frame images for presentation for each disease and generates diagnosis support information while associating the frame images for presentation with the estimation results for each disease (step Sb7). Then, the diagnosis support information distributing unit 356 distributes the diagnosis support information thus generated to the corresponding mobile communication terminal device 10 (step Sb8), and ends the process. It should be noted that, in this case, the method of extracting the frame images for presentation corresponding to each disease in step Sb6 is the same as that in the above-described first embodiment except that the diagnosable frame image having the largest area of the pixel region reflecting the tissue where the target disease develops is used. Further, in this case, the format of the diagnosis support information generated by the diagnosis support information generating unit 355 in step Sb7 is as desired. For example, the diagnosis support information generating unit 355 may be configured to generate a list in which the frame images for presentation are associated with the disease name and information such as the presence or absence of the disease, estimated value of severity, the treatment method, and the necessity of surgery.

Further, in this modification as well, the diagnostic knowledge corresponding to each disease is basically acquired and stored in the diagnostic knowledge storage unit 334 by the same diagnostic knowledge acquiring process as in FIG. 14. However, as the acquisition method at this time, the following two methods can be adopted. (Acquisition method 1) This method is a method of acquiring the corresponding diagnostic knowledge by executing the same process as in the above-described first embodiment (FIG. 14) for each disease. (Acquisition method 2) This method is a method of acquiring the diagnostic knowledge corresponding to the plurality of diseases at once on the basis of the moving image data uploaded from the mobile communication terminal device 10. However, acquisition method 1 is the same as in the above-described first embodiment except that the target disease is a disease other than cataracts, and thus only acquisition method 2 will be described below.

(Acquisition Method 2)

When this method is adopted, in the diagnosable frame image extraction process of step Sa3 in FIG. 14, the diagnosable frame extracting unit 352 extracts diagnosable frame images for each disease by the same method as described above, and stores the corresponding disease name in the ROM/RAM 320 in association with the diagnosable frame image.

Next, in step Sa4, the diagnostic knowledge acquiring unit 353 transmits the diagnosable frame images to the annotation terminal device 40 while associating the images with the disease name stored in the ROM/RAM 320.

Upon receiving the diagnosable frame images thus transmitted, the annotation terminal device 40 displays the diagnosable frame images received from the diagnosis support server device 30 on the monitor while associating the images with the disease name. In this state, the physician, who is the annotator, diagnoses the state of each disease on the basis of the diagnosable frame images for each disease displayed on the monitor, and inputs the diagnosis results. It should be noted that the display form at this time is as desired, and may be configured by, for example, dividing the display region of the monitor into a plurality of areas, and displaying in association (a) the disease name of the region, (b) the corresponding diagnosable frame image, and (c) a GUI for inputting the diagnosis results for the disease.

Then, when the physician diagnoses each disease on the basis of the diagnosable frame images and the disease names displayed in each region and inputs the diagnosis results, the annotation terminal device 40 creates teacher data corresponding to each disease by tagging the diagnosable frame images of the corresponding disease with the diagnosis result information for each disease corresponding to the input results, and transmits the created teacher data to the diagnosis support server device 30 in association with the corresponding disease names.

On the other hand, in the diagnosis support server device 30, when the communication control unit 310 receives the teacher data transmitted from the annotation terminal device 40 (step Sa5), the teacher data is stored in the teacher data storage unit 333 while associating the data with the disease names (step Sa6).

The above processing is repeated each time moving image data is uploaded from the mobile communication terminal device 10, and teacher data is accumulated for each disease in the teacher data storage unit 333.

Then, at the timing when the quantity of teacher data corresponding to each disease stored in the teacher data storage unit 333 reaches a or greater, the determination made in step Sa7 changes to "Yes," and the diagnostic knowledge acquiring unit 353 acquires diagnostic knowledge corresponding to each disease on the basis of the teacher data for each disease accumulated in the teacher data storage unit 333 (step Sa8) and stores the knowledge in the diagnostic knowledge storage unit 334 in association with the disease name (step Sa9). It should be noted that, in steps Sa7 and Sa8, the quantity of teacher data stored in the teacher data storage unit 333 need only be compared with a for each disease, and the diagnostic knowledge for the diseases for which the quantity of teacher data reaches a or greater need only be acquired (step Sa8). Further, in a case in which there are a plurality of diseases for which the quantity of teacher data is a or greater, the diagnostic knowledge acquiring process is repeated for each disease (step Sa8) and thus the diagnostic knowledge corresponding to the plurality of diseases is acquired all at once. Then, in step Sa9, the diagnostic knowledge acquiring unit 353 need only store the diagnostic knowledge for each disease acquired in step Sa8 in the diagnostic knowledge storage unit 334 in association with the disease name of the corresponding disease.

Further, when the smart eye camera is used to capture images of the examined eye E from the front, the tissues of the cornea, anterior chamber, and lens are reflected overlapping each other, but in a case in which slit light SL is irradiated as the observation light, for example, the slit light SL is incident on the examined eye E from an oblique direction, making it possible to capture images including three-dimensional information of the examined eye E while crossing the examined eye E with the slit light SL in a cross-sectional direction. In this case, by adopting a configuration that performs multi-labeling for each pixel, it is possible to identify each pixel reflecting tissue and the name of each tissue being reflected and thus, even for a plurality of diseases occurring in a plurality of tissues that appear to overlap when captured from the front, estimate the states at once by a similar configuration, generate the diagnosis support information and distribute the information to the corresponding mobile communication terminal device 10.

[A7.7] Modification 7

In the above-described embodiment and each of the modifications, a configuration is adopted in which the state of a disease in the examined eye E is estimated with a human eye as the target, but the diagnosis support device, the diagnosis support system, and the program of the present invention can be applied to animals other than humans as well. As mentioned above, a smart eye camera can be used to observe and capture detailed images of the eyes of mice and other animals. By using the eye of an animal other than a human as the examined eye E and capturing a moving image of the eye, it is possible to estimate the health state of the eye of animal and generate and utilize diagnosis support information in the same way as for humans. The process in this case is also the same as in the above-described embodiment and modifications except that the imaging target is an animal other than a human, and thus details thereof will be omitted.

[A7.8] Modification 8

In the above-described embodiment and each of the modifications, a method of estimating the health state of the examined eye E using only a moving image captured by the smart eye camera is adopted. However, the smart eye camera, being realized by the mobile communication terminal device 10 equipped with the close-up imaging device 20, can be utilized to estimate the health state of the examined eye E regardless of country or region, and can acquire position information (latitude and longitude information, for example) indicating the location where the moving image was captured. Accordingly, it is possible to utilize the unique properties of this smart eye camera (that is, the ability to acquire position information of the imaging location) for applications such as the following as well. It should be noted that position information can be acquired by utilizing the Global Positioning System (GPS) function installed in an existing smartphone utilized as the mobile communication terminal devices 10, and thus details of the acquisition method will be omitted.

<Application Method 1>

For example, the method of this modification can be adopted to realize an application form that identifies each region having a high incidence of eye disease and the type of eye disease, and reflects the results in the health state estimation results in correspondence with the region where the moving image was captured. In this case, the position information of the imaging location is uploaded to the diagnosis support server device 30 along with the image captured by the smart eye camera. Further, in this case, the diagnosis support server device 30 transmits the diagnosable frame images extracted from the captured image to the annotation terminal device 40 while linking the images with the position information, and displays the position information (for example, plots the position on a map, or the like) along with the diagnosable frame images on the annotation terminal device 40. Then, when the physician, who is the annotator, makes a diagnosis on the basis of the displayed diagnosable frame images and the position information, the annotation terminal device 40 creates teacher data by tagging the diagnosable frame image with the corresponding diagnosis result information and position information. On the other hand, the diagnostic knowledge acquiring unit 353 acquires diagnostic knowledge on the basis of the teacher data tagged with position information. It should be noted that the other processes at this time are the same as in FIG. 14, and thus details thereof will be omitted.

Further, in a case in which the diagnosis support information is generated by this method, a configuration is adopted in which the position information is uploaded in association with the moving image captured by the smart eye camera. Then, when diagnosis support information is generated in the diagnosis support server device 30, the health state of the examined eye E may be estimated on the basis of (i) the diagnosable frame images extracted from the uploaded moving image data, (ii) the position information associated with the moving image data, and (iii) the diagnostic knowledge acquired by the above-described method. This method enables highly accurate estimation of the state of diseases that most frequently occur in the imaging region, and enables highly accurate estimation of the state of unique endemic diseases in the imaging region as well. For example, for diseases such as onchocerciasis, while cases are substantially non-existent in Japan, cases are common in sub-Saharan Africa. Therefore, by estimating the state on the basis of the position information and the diagnosable frame images, it is possible to estimate the state of this type of endemic disease with high accuracy.

<Application Method 2>

Further, for example, the method of this modification can be adopted and applied to identify regions having high incidence of various eye diseases and to determine the epidemiological prevalence of various diseases. In this case, by creating a database and keeping a diagnosis history while associating position information with the health state estimation results, it is possible to investigate epidemiologically each region having a high frequency of disease occurrence and the type of disease. It should be noted that, in this case, a configuration may be adopted in which the database of the diagnosis history is provided in the diagnosis support server device 30, or provided in a computer system owned by an epidemiological research institute for eye diseases, or the like.

[B] Second Embodiment

The above-described first embodiment is designed to estimate the state of a disease in the anterior eye tissue of the examined eye E by the diagnosis support server device 30 and to distribute the diagnosis support information including the estimation results to the corresponding mobile communication terminal device 10 for use. In contrast, this embodiment is designed to estimate the state of a disease (hypertensive retinopathy, retinal thinning, glaucoma, diabetic retinopathy, retinal detachment, central serous chorioretinopathy, age-related macular degeneration, exudative retinopathy, central retinal artery occlusion, or the like, for example) in the fundus tissue of the examined eye E and distribute the diagnosis support information including the estimation results to the mobile communication terminal device 10. It should be noted that the diagnosis support system of this embodiment differs from the diagnosis support system 1 of the first embodiment only in the configuration of the close-up imaging device 20 and the contents of the extracting knowledge and the diagnostic knowledge, and the other configurations are basically the same as those in first embodiment. Accordingly, unless otherwise explicitly stated, the diagnosis support system of this embodiment is realized by the same configurations as in the first embodiment.

[B1] Configuration of Close-Up Imaging Device 20B

Next, a configuration of a close-up imaging device 20B of this embodiment will be described with reference to FIGS. 26 to 28. It should be noted that FIGS. 26 to 28 are each a drawing illustrating a configuration of the close-up imaging device 20B of this embodiment, FIG. 26 being a perspective view of the close-up imaging device 20B, FIG. 27 being a front view of the close-up imaging device 20B of this embodiment, and FIG. 28 being an exploded configuration view of the close-up imaging device 20B of this embodiment.

The close-up imaging device 20B of this embodiment is configured to include a tubular member 180 for fundus tissue observation and imaging.
(Tubular Member)

Figure 26:
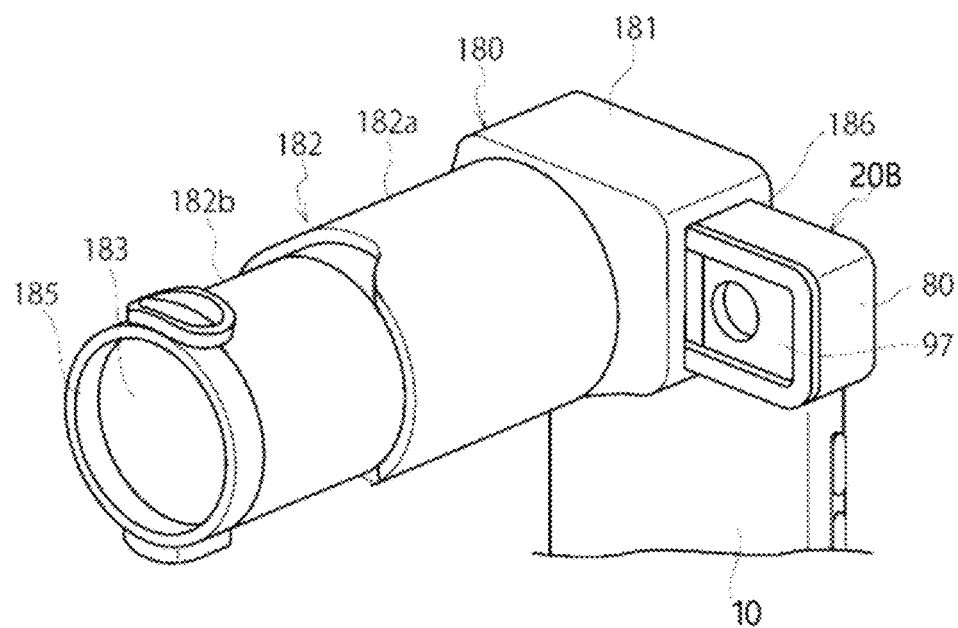
FIG. 26 is a perspective view illustrating a form of a close-up imaging device of a second embodiment.
Figure 27:
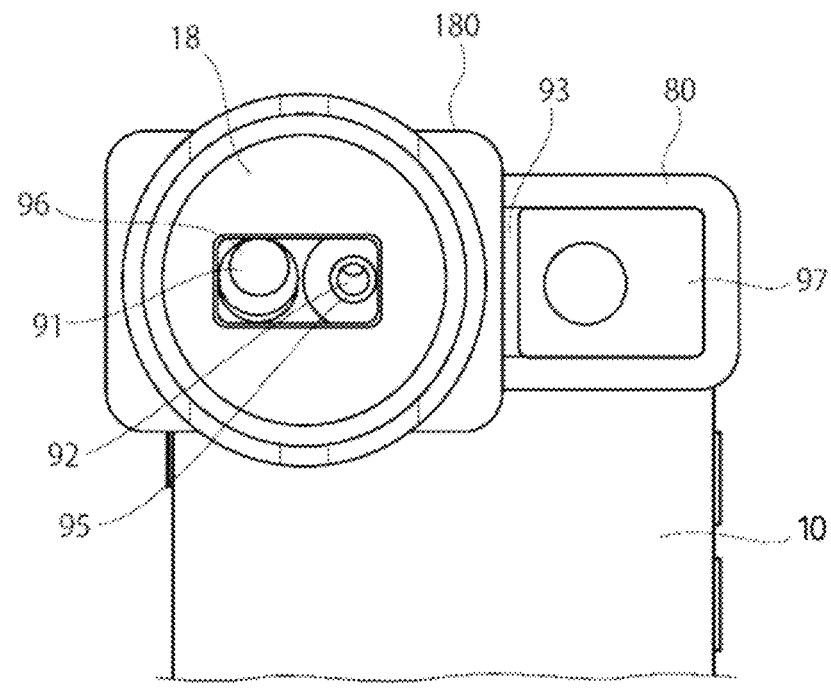
FIG. 27 is a front view of the form illustrated in FIG. 26.
Figure 28:
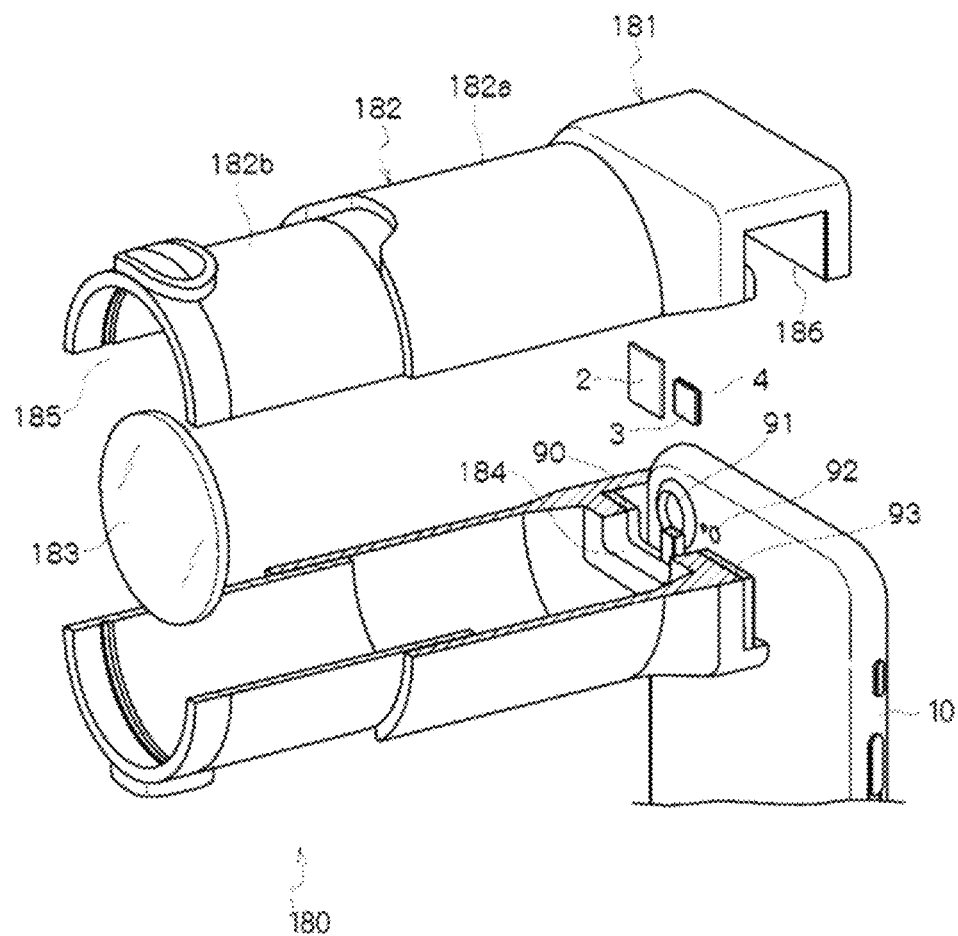
FIG. 28 is an exploded configuration view of the form illustrated in FIG. 26.

The tubular member 180, as illustrated in FIG. 26 to FIG. 28, is a member including a convex lens 183 at a tip end thereof. This tubular member 180 is also detachably mounted to the mobile communication terminal device 10. The tubular member 180 is constituted by at least a mounting part 181 for mounting to the mobile communication terminal device 10, a tube part 182 (182a, 182b), the convex lens 183, an opening 184, a convex lens holding part 185, and a mounting part 186. With such a tubular member 180, the focal length from the eye ground can be adjusted and maintained in an appropriate state. As a result, observation and imaging of the eye ground can be appropriately performed.

In the opening 184 of this tubular member 180, a color filter (orange) 4 and a polarizing filter (horizontally polarized light) 3 are disposed in that order in an optical path position of the light-source light (white diffused light) emitted from the light source 92. With this configuration, the light-source light emitted from the light source 92 is changed to orange light when transmitted through the orange color filter 4 and is converted to linearly polarized light (P polarized light, for example) by the polarizing filter 3. The observation light (linearly polarized light) obtained by converting the light-source light in this way is transmitted through the convex lens 183, irradiating the fundus tissue of the examined eye E. On the other hand, a polarizing filter (vertically polarized light) 2 is provided in an optical path position immediately before the reflected light RL (that is, return light) of the linearly polarized light reflected by the fundus tissue reaches the imaging camera lens 91. It should be noted that each of the polarizing filters 2, 3 may be either vertically polarized light or horizontally polarized light as long as one is vertically polarized light and the other is horizontally polarized light. With this configuration, it is possible to generate a phase difference between the observation light and the reflected light RL, prevent interference between the observation light (outward light) and the reflected light RL (return light) inside the tubular member 180, and thus cleanly observe and capture an image of the fundus tissue (retina) by the reflected light RL.

The orange color filter 4 is a member for converting the observation light into light that readily reaches the fundus tissue to the extent possible.

As illustrated in FIG. 28, the mounting part 186 for mounting onto the mobile communication terminal device 10 is configured to be mountable by sliding on the mobile communication terminal device 10 from the right-side wall 85 side. In the tubular member 180 after mounting, the color filter (orange) 4 and the polarizing filter 3 are provided frontward of the light source 92, and the other polarizing filter 2 is provided frontward of the imaging camera lens 91.

The tube part 182 is configured by combining the two tube parts 182a, 182b in the illustrated example, but is not particularly limited thereto. The convex lens 183 is mounted onto the convex lens holding part 185 in front of the tubular member 180, irradiates the fundus tissue with linearly polarized light as the observation light, and condenses the reflected light RL of the observation light (linearly polarized light) in the fundus tissue on the imaging camera lens 91 via the polarizing filter 2. It should be noted that the tubular member 180 may be configured as a detachable attachment to the close-up imaging device 20A illustrated in FIGS. 2 to 7. In the case of the attachment, the tubular member 180 may be configured so that the color filter 4 and polarizing filters 3, 2 are arranged in the positional relationship illustrated in FIGS. 26 to 28, the slit light forming member 61, the convex lens member 93, and the color filter member 97 are all removed from the close-up imaging device 20A illustrated in FIGS. 2 to 7, and the tubular member 180 need only be detachably attached to the housing 80.

[B2] Verification Results of Diagnosis of Disease in Fundus Tissue Using Smart Eye Camera In December 2018, the inventors observed the fundus tissue of the examined eye E using the mobile communication terminal device 10 equipped with the close-up imaging device 20B (that is, smart eye camera) including the tubular member 180 having the configuration illustrated in FIGS. 26 to 28. It should be noted that the clinical cases were the ground eyes of 41 eyes (19 males and 22 females), and the presence or absence of optic nerve abnormalities and the presence or absence of eyeground disease were evaluated.

Figure 29A:
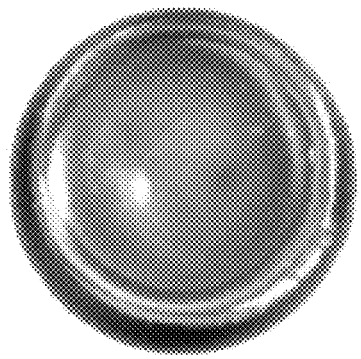
FIGS. 29A to 29D are imaging results of eye grounds captured by a smart eye camera of the second embodiment, FIG. 29A showing a normal eye ground, FIG. 29B showing hypertensive retinopathy, FIG. 29C showing retinal thinning, and FIG. 29D showing optic disk cupping and expansion (suspected glaucoma).
Figure 29B:
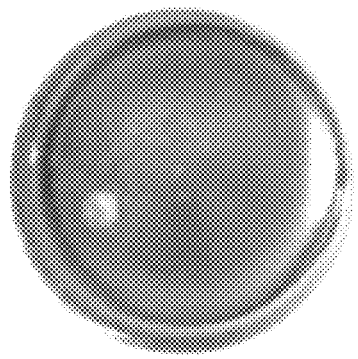
Figure 29C:
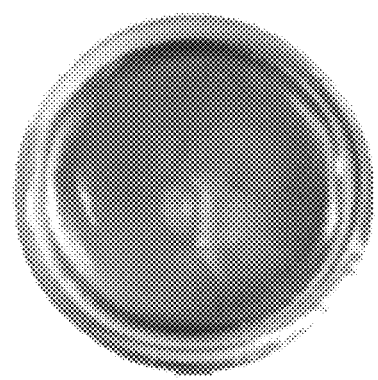
Figure 29D:
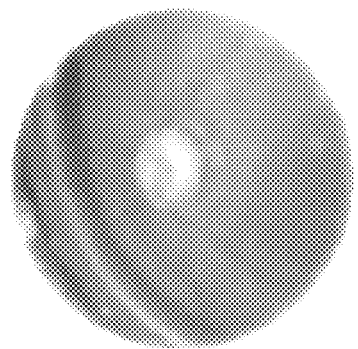

FIGS. 29A to 29D show examples of images captured by the mobile communication terminal device 10 (smartphone) equipped with the close-up imaging device 20 illustrated in FIGS. 26 to 28, with the above-described 41 eyes as the target. It should be noted that, in FIGS. 29A to 29D, FIG. 29A shows a normal eye ground, FIG. 29B shows hypertensive retinopathy, FIG. 29C shows retinal thinning, and FIG. 29D shows optic disk cupping and expansion (suspected glaucoma). Evaluation of the fundus tissue was possible in 85% or more cases, including the examples of FIGS. 29A to 29D. It should be noted that the cases impossible to evaluate were opacities of intermediate translucent bodies in severe cataracts and the like, but these cannot be evaluated even with an existing ophthalmic device. From these results, it was confirmed that, with the smart eye camera equipped with the tubular member 180 having the configuration illustrated in FIGS. 26 to 28, observation and imaging of the eye ground can be preferably performed.

Figure 30:
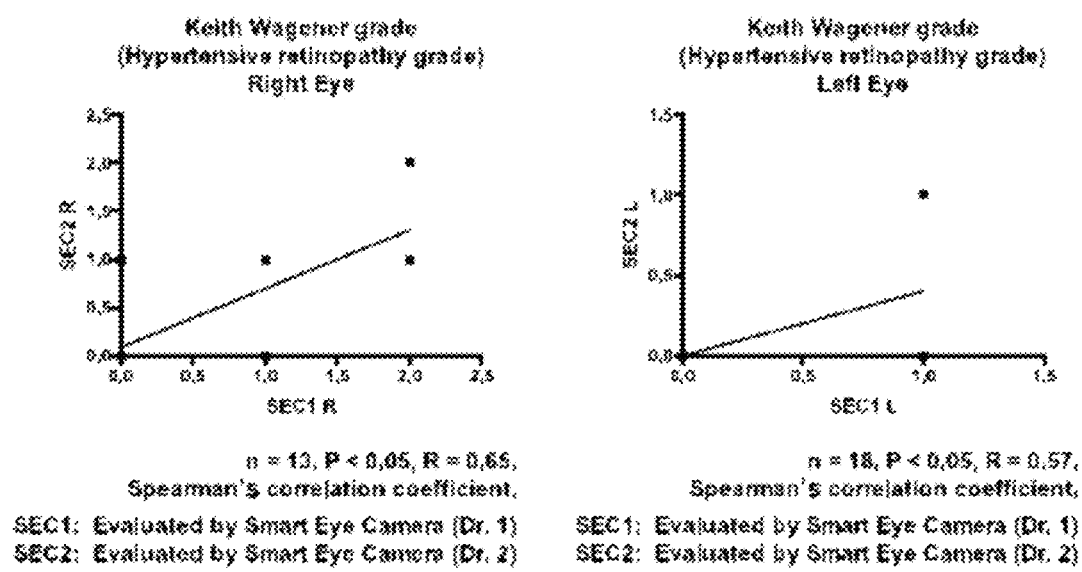
FIG. 30 is a correlation of the evaluation results between physicians of hypertensive retinopathy using the smart eye camera of the second embodiment.

FIG. 30 is a correlation of the evaluation results between physicians of hypertensive retinopathy evaluated by the mobile communication terminal device 10 equipped with the tubular member 180 having the configuration illustrated in FIGS. 26 to 28. There was no large difference between the evaluation results of the physicians. Further, the glaucoma diagnosis rates were also 25.7% and 18.9% in the evaluation results of the physicians, having no large difference regarding this as well. From these results, it was confirmed that, with the smart eye camera equipped with the tubular member 180 in FIGS. 26 to 28, observation and imaging of the fundus tissue of the examined eye E can be performed in detail without inferiority to existing ophthalmic devices.

In a case in which the presence or absence of various diseases that develop in the fundus tissue of the examined eye E and the severities thereof are actually estimated with the diagnosis support system of this embodiment, it is necessary to mount the close-up imaging device 20B including the tubular member 180 illustrated in FIGS. 26 to 28 to the mobile communication terminal device 10, and capture a moving image including diagnosable frame images that can be utilized for diagnosis of the corresponding disease while irradiating the fundus tissue of the examined eye E with linearly polarized light as the observation light.

Then, in this case, the extracting knowledge for extracting diagnosable frame images that can be utilized for the diagnosis of diseases that develop in the fundus tissue, such as hypertensive retinopathy, retinal thinning, glaucoma, diabetic retinopathy, retinal detachment, central serous chorioretinopathy, age-related macular degeneration, exudative retinopathy, and central retinal artery occlusion, is stored in the extracting knowledge storage unit 332 in advance. It should be noted that the conditions of a diagnosable frame image that can be utilized for diseases that develop in the fundus tissue, such as hypertensive retinopathy, retinal thinning, glaucoma, diabetic retinopathy, retinal detachment, central serous chorioretinopathy, age-related macular degeneration, exudative retinopathy, and central retinal artery occlusion, are that the tissue to be observed is irradiated with linearly polarized light as the observation light, and the image reflecting at least a portion of the tissue to be observed is in focus along with the reflected light RL of the linearly polarized light in the tissue to be observed. Therefore, the system need only be configured to store the extracting knowledge for extracting frame images that satisfy these conditions in the diagnostic knowledge storage unit 334 in advance.

Further, in this embodiment as well, the diagnosis processing unit 350 basically acquires diagnostic knowledge by executing the same diagnostic knowledge acquiring process as in FIG. 14 (step Sa8) and stores the knowledge in the diagnostic knowledge storage unit 334 (step Sa9). Then, while using the acquired diagnostic knowledge, the diagnosis processing unit 350 executes the same diagnosis support information generation process as in FIG. 15, estimates the state of the disease in the fundus tissue (step Sb5), generates diagnosis support information (step Sb7), and distributes the information to the corresponding mobile communication terminal device 10 (step Sb8). It should be noted that the process at this time is the same as in the above-described first embodiment except that the target disease is not cataracts, but a disease that develops in the fundus tissue, such as hypertensive retinopathy. Further, as in the above-described Modification 6, in this embodiment as well, a configuration may be adopted in which the states of a plurality of diseases are estimated for each disease at once, and the diagnosis support information including the estimation results for each disease is generated and distributed. Furthermore, in this embodiment as well, a configuration can be adopted in which the most plausible state of the disease in the fundus tissue of the examined eye E is estimated while weighting the estimation results in correspondence with the probability of each diagnosable frame image being classified as "Diagnosable." This, however, is similar to the above-described first embodiment, and thus details thereof will be omitted.

As described above, the diagnosis support system of this embodiment is configured to extract diagnosable frame images from a moving image captured by the mobile communication terminal device 10 equipped with the close-up imaging device 20B including the tubular member 180, acquire diagnostic knowledge corresponding to the disease that develops in the fundus tissue on the basis of the diagnosable frame images, and estimate the presence or absence of the disease in the fundus tissue, the severity, the treatment method, the necessity of surgery, and the like in the examined eye E on the basis of the diagnostic knowledge and the moving image data uploaded from the mobile communication terminal device 10. In a case in which the mobile communication terminal device 10 equipped with the close-up imaging device 20B is used, even a paramedic or a layperson such as a family member of the patient who is not familiar with ophthalmic diagnostic imaging can easily capture a moving image including one or more diagnosable frame images that can be utilized for diagnosis of a disease that develops in the fundus tissue, with simple operations similar to those of a conventional smartphone and the like. Therefore, according to the configuration of this embodiment, it is possible to appropriately estimate the state of a disease in the fundus tissue of the examined eye E and generate and make diagnosis support information available on the basis of a moving image captured by a layperson, without the use of expensive ophthalmic diagnostic imaging device. Further, the close-up imaging device 20B can be manufactured at an extremely low cost compared to ophthalmic eyeground imaging devices, thereby estimating the state of a disease in the fundus tissue of the examined eye E and generating diagnosis support information even in regions where budgets for examination device cannot be secured.

[C] Third Embodiment

In the above-described first and second embodiments and the modifications thereof, a configuration is adopted in which the diagnosable frames included in a moving image captured by a smart eye camera are transmitted as is to the annotation terminal device 40 in accordance with the process illustrated in FIG. 14, the diagnosis is made by the physician who is the annotator, and teacher data corresponding to each diagnosable frame image is created by tagging the corresponding diagnosable frame image with the diagnosis result information to acquire diagnostic knowledge.

In contrast, in the diagnosis support system 1 of this embodiment, a configuration is adopted in which, when the diagnosis support server device 30 transmits the frame images extracted from moving image as diagnosable frame images to the annotation terminal device 40, the diagnosable frame extracting unit 352 performs machine learning that cuts out regions reflecting eye tissue from the diagnosable frame images. It should be noted that the diagnosis support system 1 of this embodiment is basically realized by the same configurations as in the first and second embodiments and the modifications thereof. That is, in this embodiment as well, each component constituting the diagnosis support system 1 has the same functions and performs the same operations as in the above-described first embodiment and the like, and thus only the points that differ from the above-described first embodiment and the like will be described below.

[C1] Method of Cutting Out Region Reflecting Eye Tissue from Diagnosable Frame Image Next, a method by which the diagnosis support server device 30 in the diagnosis support system 1 of this embodiment cuts out an image of a region reflecting the eye tissue (hereinafter also referred to as the "region image") from a diagnosable frame image will be described with reference to FIGS. 31A and 31B. It should be noted that FIGS. 31A and 31B are images for describing an annotation task for cutting out a region image from a diagnosable frame image, and images for describing the annotation task for cutting out a region reflecting eye tissue in the diagnosable frame image captured when irradiated with white diffused light and blue light as the observation light, respectively.

In this embodiment, first, a method by which a human performs annotation for cutting out a region reflecting the eye tissue in the diagnosable frame image is adopted. At this time, the diagnosable frame extracting unit 352 of the diagnosis support server device 30 extracts diagnosable frame images that can be utilized for diagnosis of various diseases from the moving image data uploaded from the mobile communication terminal device 10 (smart eye camera), and transmits the extracted diagnosable frame images to the annotation terminal device 40 to present the images to the annotator. Then, the annotator performs the task of cutting out the region reflecting the eye tissue in the diagnosable frame image. It should be noted that, although it is desirable that the annotation at this time be performed by a physician, any person may be the annotator since regions reflecting the eye tissue in the diagnosable frame image can be identified even by non-ophthalmologists.

At this time, the annotation terminal device 40 displays the diagnosable frame images transmitted from the diagnosis support server device 30. The annotator then uses an annotation tool mounted on the annotation terminal device 40 to annotate the image by enclosing the region reflecting each tissue of the eye in the diagnosable frame image in a rectangular region as shown in FIGS. 31A and 31B.

Figure 31A:
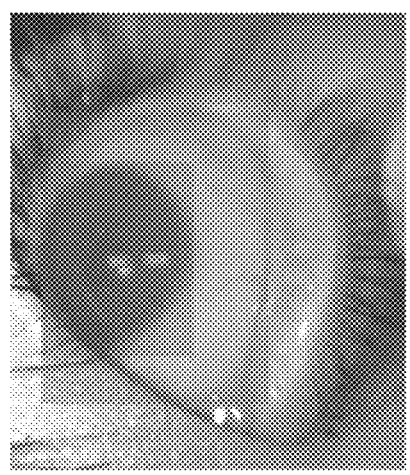
FIGS. 31A and 31B are images for describing an annotation task for cutting out a region image from a diagnosable frame image in the diagnosis support server device of a third embodiment, and images for describing the annotation task for cutting out a region reflecting eye tissue in the diagnosable frame images captured when irradiated with white diffused light and with blue light as observation light, respectively.
Figure 31B:
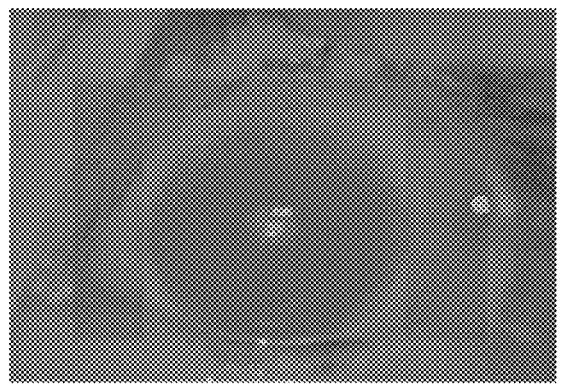

Specifically, at this time, the annotator performs the task of enclosing, in the diagnosable frame image, the "region reflecting the cornea" with a blue rectangle and enclosing the "region reflecting the entire eye" with a red rectangle, as exemplified in FIGS. 31A and 31B, thereby annotating the image. In the annotation, teacher data is created and at least one of machine learning or data mining is performed while tagging the diagnosable frame image with the data of the upper left and lower right coordinates of the rectangular regions obtained in this way, thereby acquiring knowledge for cutting out a region image from the diagnosable frame image (hereinafter also referred to as "cutout knowledge"). Specifically, at this time, to acquire cutout knowledge, at least one of machine learning and data mining is performed by creating teacher data by pairs of diagnosable frame images and annotated rectangular regions. It should be noted that the specific learning algorithm used to acquire the cutout knowledge is as desired and, for example, a configuration may be adopted in which learning is performed by inputting teacher data into an objective detection algorithm so that an error is reduced. Objective detection may, in principle, estimate a plurality of regions of a single image, but because the diagnosable frame reflects only one eye, the region having the largest probability need only be selected. This makes it possible to uniquely cut out the cornea and the entire eye in a single frame. Further, for example, the cutout knowledge may be stored together with the extracting knowledge in the extracting knowledge storage unit 332, or a configuration may be adopted in which a storage region for cutout knowledge is allocated in the storage device 330 to provide a cutout knowledge storage unit (not illustrated). Furthermore, although FIGS. 31A and 31B show cases of cutting out the cornea from moving images captured using white diffused light and blue light as the observation light, this embodiment is not only available for the cornea, and can be applied to any tissue of the eye, such as the conjunctiva, some eyelid tissue, the iris, and the fundus tissue. In addition, the observation light that can be utilized in this embodiment is not limited to white diffused light and blue light. This embodiment can also be applied to a moving image that utilizes the slit light SL or linearly polarized light as the observation light. In this case, the annotator need only enclose the region reflecting the target tissue in the diagnosable frame image with a blue rectangle and enclose the region reflecting the entire eye with a red rectangle. In short, by specifying a range enclosed by the blue rectangle in correspondence with the target tissue, it is possible to cut out a region image reflecting any tissue. It should be noted that, in a case in which linearly polarized light is used, the close-up imaging device 20B of the second embodiment may be mounted to the mobile communication terminal device 10 to capture a moving image of the fundus tissue, and the annotator may, for example, enclose the tissue of the macula and the like reflected in the diagnosable frame image with a blue rectangle and enclose the entire image with a red rectangle as the regions to be cut out in the fundus tissue.

[C2] Estimation and Cutout Methods of Region Image Reflecting Eye Tissue

Next, a method of cutting out a region image while estimating a region reflecting the eye tissue in a diagnosable frame image will be described with reference to FIG. 32. It should be noted that FIG. 32 is an image for describing a method by which the diagnosable frame extracting unit 352 of the diagnosis support server device 30 of this embodiment estimates a region reflecting the eye tissue from the diagnosable frame image, and cuts out the region images.

Figure 32:
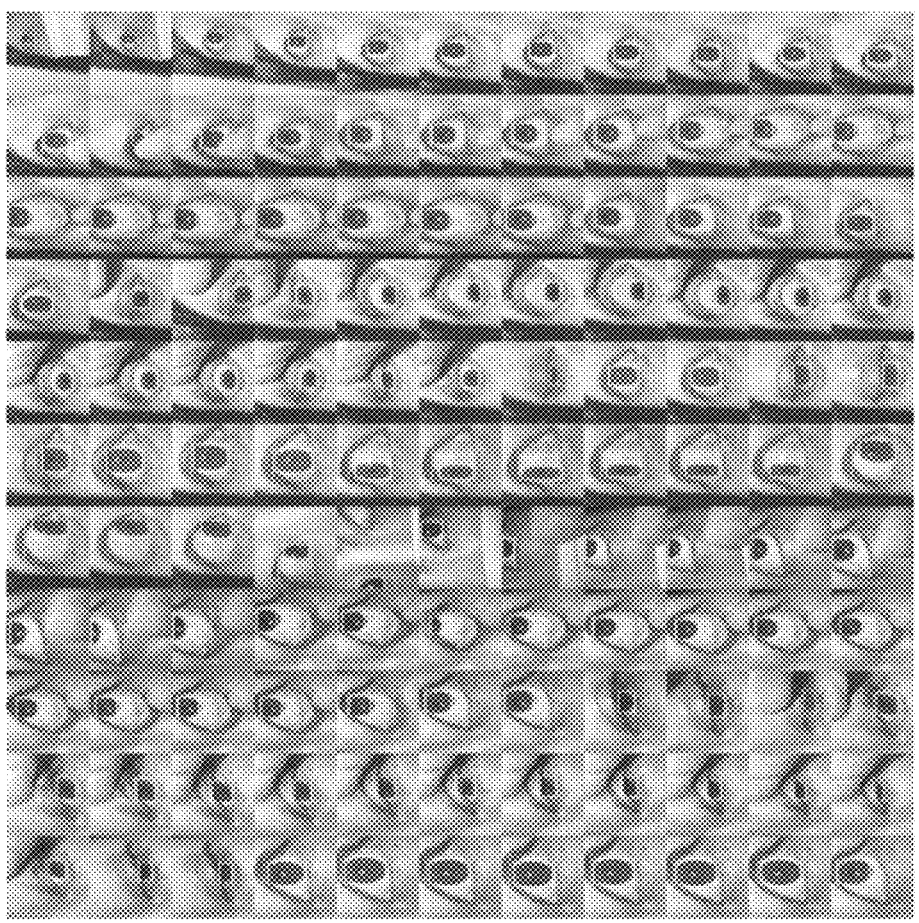
FIG. 32 is an image for describing a method of estimating a region reflecting eye tissue and cutting out the region image from a diagnosable frame image in the diagnosis support server device of the third embodiment.

With the configuration of this embodiment, the diagnosable frame extracting unit 352 uses the learned cutout knowledge to perform region detection in the diagnosable frame image, estimate the region reflecting the cornea (yellow rectangular region portion) and the region reflecting the entire eye (green rectangular region portion) from each diagnosable frame image, and cut out the region images as shown in FIG. 32. As a result, it was found that the region reflecting the cornea and the region reflecting the entire eye can be estimated and cut out substantially accurately, as exemplified in FIG. 32. It should be noted that, during the actual diagnostic knowledge acquisition and diagnosis support information generation described below, the region image is configured to be cut out as the smallest square in the diagnosable frame image that includes this region at its center.

[C3] Acquisition Method of Diagnostic Knowledge

When diagnostic knowledge is acquired after acquisition of the cutout knowledge by the above-described method, the diagnostic knowledge is basically acquired by the same process as in FIG. 14 in this embodiment as well.

However, in this embodiment, the diagnosable frame extracting unit 352 reads the extracting knowledge and the cutout knowledge from the storage device 330 in step Sa2 and, in step Sa3, extracts the diagnosable frame images on the basis of the extracting knowledge and subsequently cuts out the region images reflecting the eye tissue in the diagnosable frame images as described above on the basis of the cutout knowledge. It should be noted that the diagnosable frame extracting unit 352 of this embodiment constitutes the "cutout means" of the present invention, for example.

Then, in step Sa4, the diagnostic knowledge acquiring unit 353 transmits the region images cut out from the diagnosable frame images to the annotation terminal device 40. The annotation terminal device 40, while displaying the region images, has the physician who is the annotator input diagnosis results based on the region images and creates teacher data tagged with diagnosis result information corresponding to the input content, and the diagnostic knowledge acquiring unit 353 acquires the created teacher data from the annotation terminal device 40 ("Yes" in step Sa5). Then, in the diagnostic knowledge acquiring unit 353, the teacher data is stored in the teacher data storage unit 333 (step Sa6) and, when the quantity of stored teacher data reaches a or greater ("Yes" in step Sa7), diagnostic knowledge is acquired on the basis of the stored teacher data (step Sa8) and stored in the diagnostic knowledge storage unit 334 (step Sa9). The process then ends.

[C4] Generation Method of Diagnosis Support Information

In this way, when the diagnostic knowledge based on the region images cut out from the diagnosable frame images and the cutout knowledge are acquired, and the moving image data is subsequently uploaded from the mobile communication terminal device 10, the diagnosis support information is basically generated by the same process as in FIG. 15 by the diagnosis processing unit 350 (step Sb7 in FIG. 15) and distributed to the corresponding mobile communication terminal device 10 (step Sb8 in FIG. 15).

However, in this embodiment, the diagnosable frame extracting unit 352, in step Sb3, extracts the diagnosable frame images from the moving image data uploaded from the smart eye camera, and subsequently cuts out region images from the extracted diagnosable frame images by the above-described method on the basis of the cutout knowledge.

Then, the health state estimation processing unit 354 generates diagnosis support information on the basis of the region images and the diagnostic knowledge by basically the same process as in FIG. 15. At this time, the health state estimation processing unit 354 estimates the health state of the examined eye E captured by the smart eye camera on the basis of the region images cut out from the diagnosable frame image in step Sb5 and the diagnostic knowledge (step Sb5), extracts the frame image for presentation (step Sb6), subsequently generates the diagnosis support information (step Sb7), distributes the information to the mobile communication terminal device 10 from which the moving image was uploaded (step Sb8), and ends the process. It should be noted that the process at this time is basically the same as in the first embodiment, and thus details thereof will be omitted. Further, in this case, the frame image for presentation extracted in step Sb6 may be extracted by the same method as in the first embodiment, and only the region image of the eye cut out from the diagnosable frame image extracted as the frame image for presentation may be used as the frame image for presentation.

With the above configuration, the diagnosis support system 1 of this embodiment can estimate the health state of the examined eye E with very high accuracy, and generate and make diagnosis result information including the diagnosis results having higher accuracy available. In particular, in a case in which a smart eye camera is used to capture a moving image of the examined eye E and the image includes frame images with different zoom levels, the diagnosable frame images are normalized to the same size, making it possible to improve the accuracy of machine learning during diagnostic knowledge acquisition and estimate the health state of the examined eye E with high accuracy.

The diagnosis support system 1 of this embodiment was used to actually capture moving images of the examined eye E by a smart eye camera while irradiating the examined eye E with each observation light, such as slit light, white diffused light, linearly polarized light, and blue light, region images were cut out from the diagnosable frame images included in the captured moving image and, based on the region images, the states of various diseases such as iritis and uveitis that develop in the anterior chamber tissue, chalazion and hordeolum that develop in the eyelid tissue, allergic conjunctivitis, epidemic keratoconjunctivitis, conical cornea, corneal opacity, superficial punctate keratitis, corneal ulcers, and DED that develop in the corneal and conjunctival tissue, and diseases that develop in the fundus tissues were estimated. As a result, it was found that, according to the method of this embodiment, the accuracy of diagnosis is significantly improved.

In particular, it was found that DED can be diagnosed with very high accuracy while estimating TFBUT with high accuracy, and various types of subtypes of DED, such as, for example, (a) spot break, (b) area break, (c) dimple break, (d) line break, and (e) random break, can also be diagnosed.

As described above, according to the diagnosis support system 1 of this embodiment, it is possible to acquire diagnostic knowledge while cutting out region images reflecting a target tissue of the eye from diagnosable frame images included in a moving image captured by a smart eye camera. Further, even during estimation (diagnosis) of the health state of the examined eye E, a region image can be used to obtain highly accurate estimation results and generate and make more practical, highly accurate diagnosis support information available. It should be noted that, in the configuration of this embodiment, it is desirable to adopt a configuration in which states of a plurality of disease are estimated and made available at once by capturing a single moving image, as in Modification 6. In this case, the system need only be configured to store the cutout knowledge for the plurality of diseases and the diagnostic knowledge based on region images in the storage device 330 in advance and, when the moving image data is uploaded from the smart eye camera, cut out, for each disease, the region images for estimating the state of each disease, and estimate the states of the plurality of diseases occurring in the examined eye E at once on the basis of the cut-out region images and the diagnostic knowledge for the corresponding disease. Further, in this case, as in Modification 6, the system may be configured to generate diagnosis support information describing the estimation results for each disease based on the region images in a list format. Furthermore, in this case, as in Modification 6, the system may be configured to acquire diagnostic knowledge corresponding to the plurality of diseases at once. In addition, in the configuration of this embodiment, as in Modification 4, the system may be configured to construct a three-dimensional image from the region images, and acquire diagnostic knowledge on the basis of the three-dimensional image, or estimate the health state of the examined eye E on the basis of the three-dimensional image obtained by layering the region images. In this case, the system need only be configured to layer the region images cut out from each diagnosable frame image in correspondence with focal length and generate the three-dimensional image. It should be noted that the other points are the same as in Modification 4, and thus details thereof will be omitted.

[D] Fourth Embodiment

In each of the above-described embodiments and modifications, a configuration is adopted in which the diagnostic knowledge is acquired on the basis of only a moving image captured by a smart eye camera.

In contrast, in the diagnosis support system 1 of this embodiment, a method of acquiring diagnostic knowledge by creating teacher data while linking information parameter values (specifically, measured values of length, angle, area, and the like of some tissues in the examined eye E) obtained not only from the smart eye camera but also from various ophthalmic devices installed in the eye care facility (not illustrated) with the diagnosable frame images, and by executing at least one of machine learning and data mining on the basis of the teacher data is adopted. Then, in this embodiment, a configuration is adopted in which the acquired diagnostic knowledge is used to estimate the values of the information parameters in the examined eye E from the moving image captured by the smart eye camera. It should be noted that the diagnosis support system 1 of this embodiment is basically realized by the same configurations as in the first and second embodiments and the modifications thereof. That is, in this embodiment as well, each component constituting the diagnosis support system 1 has the same function and performs the same operation as in the above-described first embodiment and the like, and thus only the points that differ from the above-described first embodiment and the like will be described below.

In this embodiment, the annotation terminal device 40 is installed in an eye care facility (not illustrated), and a method is adopted in which the physician, who is the annotator, uses various ophthalmic devices installed in the eye care facility, such as described below to acquire various information parameter values related to the examined eye E. Then, in the diagnosis support system 1 of this embodiment, when the diagnostic knowledge is acquired, the teacher data is created while linking the diagnosable frame images with the information parameters acquired by these ophthalmic devices, and the diagnostic knowledge is acquired by using the teacher data. It should be noted that, as the diagnosable frame images utilized for acquiring diagnostic knowledge in this embodiment, those extracted from the moving image may be utilized as is as in the first embodiment, or region images cut out from the diagnosable frame images may be utilized as in the third embodiment.

[D1] Types of Ophthalmic Devices that can be Utilized in this Embodiment and the Information Parameter Values Acquirable by Each Device In this embodiment, to create teacher data, the specific types of the used ophthalmic devices and the acquired information parameter values related to the examined eye E are as desired and, for example, the system may be configured to acquire the information parameter values described below using ophthalmic device such as described below and create teacher data while linking the information parameter values with the diagnosable frame images.

(1) Anterior Eye Optical Coherence Tomography (OCT)

In a case in which an anterior eye OCT is used, information parameter values such as corneal thickness, anterior chamber depth, corneal curvature radius, corner angle, astigmatic frequency, pupil diameter, and higher-order aberration of the examined eye E can be acquired, making it possible to create teacher data with these information parameter values linked to the diagnosable frame images, acquire diagnostic knowledge, utilize the diagnostic knowledge, and thus estimate these information parameter values from the smart eye camera images.

(2) Auto-Refkeratometer

In a case in which an auto-refkeratometer is used, information parameter values such as refraction, corneal curvature radius, myopia, hyperopia, and astigmatic frequency of the examined eye E can be acquired, making it possible to create teacher data with these information parameter values linked to the diagnosable frame images, acquire diagnostic knowledge, utilize the diagnostic knowledge, and thus estimate these information parameter values from the smart eye camera images.

(3) Non-Contact Tonometer

In a case in which a non-contact tonometer is used, information parameter values such as an intraocular pressure of the examined eye E can be acquired, making it possible to create teacher data with these information parameter values linked to the diagnosable frame images, acquire diagnostic knowledge, utilize the diagnostic knowledge, and thus estimate intraocular pressure of the examined eye E from the smart eye camera images.

(4) Specular Microscope

In a case in which a specular microscope is used, information parameter values related to corneal endothelial cells of the examined eye E can be acquired, making it possible to create teacher data with the information parameter values linked to the diagnosable frame images, acquire diagnostic knowledge, utilize the diagnostic knowledge, and thus estimate these information parameter values from the smart eye camera images.

(5) Eyeground Camera

In a case in which an eyeground camera is used, eyeground photographs of the examined eye E can be acquired, making it possible to create teacher data while tagging the diagnosable frame images with the diagnosis result information corresponding to the diagnosis result of the physician, based on the eyeground photographs corresponding to the various eyeground diseases, acquire diagnostic knowledge, and utilize the diagnostic knowledge, and thus estimate with high accuracy the states of various diseases that develop in the ground eye from smart eye camera images. It should be noted that, with regard to an eyeground photograph, diagnosable frame images acquired by the method of the second embodiment may be utilized as is for teacher data creation, or region images may be cut out and utilized for teacher data creation.

(6) OCT and Optical Interference-Type Axial Length Measuring Device

In a case in which OCT and an optical interference-type axial length measuring device are used, information parameter values of retinal thickness, optic disk diameter, retinochoroidal vessels, and the like of the examined eye E can be measured, making it possible to create teacher data with these information parameter values linked to the diagnosable frame images, acquire diagnostic knowledge, utilize the diagnostic knowledge, and thus estimate these information parameter values from the smart eye camera images. It should be noted that, in this case as well, it is possible to create teacher data on the basis of region images.

(7) Ultrasonic Tomographic Imaging Device

In a case in which an ultrasonic tomographic imaging device is used, information parameter values such as an axial length of the examined eye E can be acquired, making it possible to create teacher data with the information parameter values linked to the diagnosable frame images, acquire diagnostic knowledge, utilize the diagnostic knowledge, and thus estimate the axial length from the smart eye camera images.

(8) Perimeter

In a case in which a perimeter is used, information parameter values related to static and dynamic visual fields of the examined eye E can be acquired, making it possible to create teacher data with these information parameter values linked to the diagnosable frame images, acquire diagnostic knowledge, utilize the diagnostic knowledge, and thus estimate these information parameter values from the smart eye camera images.

(9) Regulatory Function Analyzer

In a case in which a regulatory function analyzer is used, information parameter values related to the regulatory function of the examined eye E can be acquired, making it possible to create teacher data with the information parameter values linked to diagnosable frame images, acquire diagnostic knowledge, utilize the diagnostic knowledge, and thus estimate the information parameter values related to the regulatory function of the eye from the smart eye camera images.

(10) Flicker Measuring Device

In a case in which a flicker measuring device is used, information parameter values of a flicker value of the examined eye E can be acquired, making it possible to create teacher data with the information parameter values linked to the diagnosable frame images, acquire diagnostic knowledge, utilize the diagnostic knowledge, and thus estimate the flicker value of the examined eye E from the smart eye camera images.

[D2] Acquisition Method of Diagnostic Knowledge

In the diagnosis support system 1 of this embodiment, diagnostic knowledge is basically acquired by the same process as in FIG. 14.

However, in a case in which the information parameter values in the examined eye E are estimated by the method of this embodiment, additional conditions are required on top of the above-described three conditions. Therefore, in step Sa3, a method is adopted in which the diagnosable frame extracting unit 352 extracts the frame images that satisfy the additional conditions as diagnosable frame images. It should be noted that the additional conditions will be described in detail below.

Further, in this embodiment, upon reception of the diagnosable frame images from the diagnosis support server device 30 in step Sa4 in FIG. 14, the annotation terminal device 40 displays, while displaying the diagnosable frame images, a GUI for the annotator to input the diagnosis results based on diagnosable frame images and the information parameter values acquired by the ophthalmic devices. Then, when the physician who is the annotator inputs (a) the diagnosis results based on the diagnosable frame images and (b) the information parameter values acquired by the ophthalmic devices, the annotation terminal device 40 creates teacher data while tagging the corresponding diagnosable frame images with (a) the diagnosis result information corresponding to the input diagnosis results and (b) the input information parameter values, and transmits the data to the diagnosis support server device 30. It should be noted that, in this case, it is necessary to acquire the information parameter values related to the same eye as the examined eye E captured by the smart eye camera and create teacher data by linking the values to the diagnosable frame images, but the specific method of doing so is as desired, and either the following methods a or b can be adopted, for example.

(Method a)

(Step a1) In this method a, first, the eye of the patient (that is, examined eye E) is captured by a smart eye camera at the eye care facility where the annotation terminal device 40 is installed, and the moving image data of the captured examined eye E is uploaded to the diagnosis support server device 30. (Step a2) The diagnosis support server device 30 extracts diagnosable frame images from the uploaded moving image data and distributes the images to the annotation terminal device 40 installed in the corresponding eye care facility. (Step a3) Then, the physician, who is an annotator, measures various information parameter values related to the eye of the patient (that is, examined eye E) with ophthalmic devices while making a diagnosis on the basis of the diagnosable frame images, and inputs the measured various information parameter values together with the diagnosis results into the annotation terminal device 40. (Step a4) The annotation terminal device 40 creates the teacher data while tagging the diagnosable frame images with the diagnosis result information and the measured various information parameter values input by the physician.

(Method b)

(Step b1) In this method b, first, a patient ID is assigned in advance to uniquely identify each patient within the diagnosis support system 1. (Step b2) When a moving image captured by a smart eye camera is uploaded, the patient ID assigned to the patient is input and uploaded while associating the ID with the moving image data. (Step b3) At the eye care facility as well, the measurement results from the ophthalmic device are input into an electronic medical record or the like while inputting the patient ID, and the input measurement values are stored in a database (not illustrated) while associating the values with the patient ID. (Step b4) When the moving image data associated with the patient ID is uploaded from the smart eye camera, the diagnosis support server device 30 extracts the diagnosable frame images from the moving image and transmits the images to the annotation terminal device 40 while associating the images with the patient ID. (Step b5) The annotation terminal device 40 acquires the measured values stored in the database in association with the patient ID. (Step Sb6) The annotation terminal device 40 creates teacher data while linking the diagnosis results of the physician and the measured values acquired from the database to the diagnosable frame images.

Upon receiving the teacher data thus created from the annotation terminal device 40 ("Yes" in step Sa5 in FIG. 14), the diagnostic knowledge acquiring unit 353, while storing the teacher data in the teacher data storage unit 333 (step Sa6 in FIG. 14), executes at least one of machine learning and data mining to acquire the diagnostic knowledge on the basis of the teacher data when the quantity of teacher data reaches a or greater (step Sa8), stores the information in the diagnostic knowledge storage unit 334 (step Sa9), and subsequently ends the process. At this time, the diagnostic knowledge acquiring unit 353, in linkage with the health state estimation processing unit 354, executes at least one of machine learning and data mining to ensure that errors between the measured values acquired by the ophthalmic devices and the estimated values based on the diagnosable frame images are "0," and acquires the diagnostic knowledge.

[D3] Generation Method of Diagnosis Support Information

In the diagnosis support system 1 of this embodiment as well, the information parameter values related to the examined eye E captured by the smart eye camera is estimated and the diagnosis support information including the estimated information parameter values is generated by basically the same process as in FIG. 15.

However, in the configuration of this embodiment, to estimate the information parameter values in the examined eye E, it is necessary to extract frame images that satisfy the additional conditions described below as diagnosable frame images as described above. Therefore, in step Sb3 in FIG. 15, a method is adopted in which the diagnosable frame extracting unit 352 extracts the diagnosable frames images that satisfy the conditions, and estimates the information parameter values in the examined eye E on the basis of the diagnosable frame images and the diagnostic knowledge. Further, in this embodiment, the health state estimation processing unit 354 estimates the information parameter values related to the examined eye E in step Sb5. It should be noted that, in this embodiment, the diagnosis support information generated by the diagnosis processing unit 350 of the diagnosis support server device 30 (1) may include only the estimated information parameter values, (2) may include only the estimation results of the disease state in the examined eye E as in the first embodiment, or (3) may include both the estimation results of the disease state and the estimation results of the information parameter values. As a method of generating the diagnosis support information that includes both, (a) a method of initially estimating the state of the disease in the examined eye E by the same process as in the first embodiment and subsequently estimating the information parameter values may be adopted, or (b) a method of estimating the state of the disease and the information parameter values at once on the basis of the diagnostic knowledge may be adopted. In the former case, the same process as in FIG. 15 need only be repeated to estimate the state of the disease and the information parameter values. In the latter case, (i) the health state estimation processing unit 354 may be configured to estimate the state of the disease in the examined eye E and the information parameter values at once in step Sb5 from the diagnostic knowledge obtained on the basis of the teacher data tagged with the diagnosis result information and the information parameter values, or (ii) a configuration may be adopted in which the diagnostic knowledge includes knowledge described in medical books, medical encyclopedias, medical theses, and other literature, or medical knowledge disclosed on the Internet, and a method may be adopted in which the health state estimation processing unit 354 estimates the state of disease in the examined eye E on the basis of various information parameter values estimated from the smart eye camera image and knowledge from the medical books and the like, and describes the state in the diagnosis support information together with the information parameter values. Whichever method is adopted, the process is basically the same as in FIG. 15 except that (1) a condition for qualifying as a diagnosable frame image to be extracted is added in step Sb3 and (2) the health state estimation processing unit 354 estimates information parameter values in step Sb5.

[D4] Application Example of this Embodiment

Next, an application example of a diagnosis form that utilizes the diagnosis support system 1 of this embodiment will be described. The diagnosis support system 1 of this embodiment, as in the above-described first and second embodiments and the modifications thereof, (1) in addition to cataract diagnosis in the examined eye E, can be utilized to estimate the states of (2) diseases such as iritis and uveitis that develop in the anterior chamber tissue, (3) diseases such as chalazion and hordeolum that develop in the eyelid tissue, and allergic conjunctivitis, epidemic keratoconjunctivitis, conical cornea, and corneal opacity that develop in the corneal and conjunctival tissue, (4) diseases such as superficial punctate keratitis and corneal ulcers, (5) DED, and (6) diseases in fundus tissue, and generate and make diagnosis support information including the estimation results available. In particular, according to the diagnosis support system 1 of this embodiment, the information parameter values measured by the ophthalmic devices can be utilized for the following applications.

(1) Estimation of Anterior Chamber Depth (ACD)

To verify the applicability of the diagnosis support system 1 of this embodiment, the inventors conducted an experiment to actually estimate an anterior chamber depth in the examined eye E on the basis of a moving image of the examined eye E captured by a smart eye camera.

(1-1) Overall Flow of this Experiment

Figure 33:
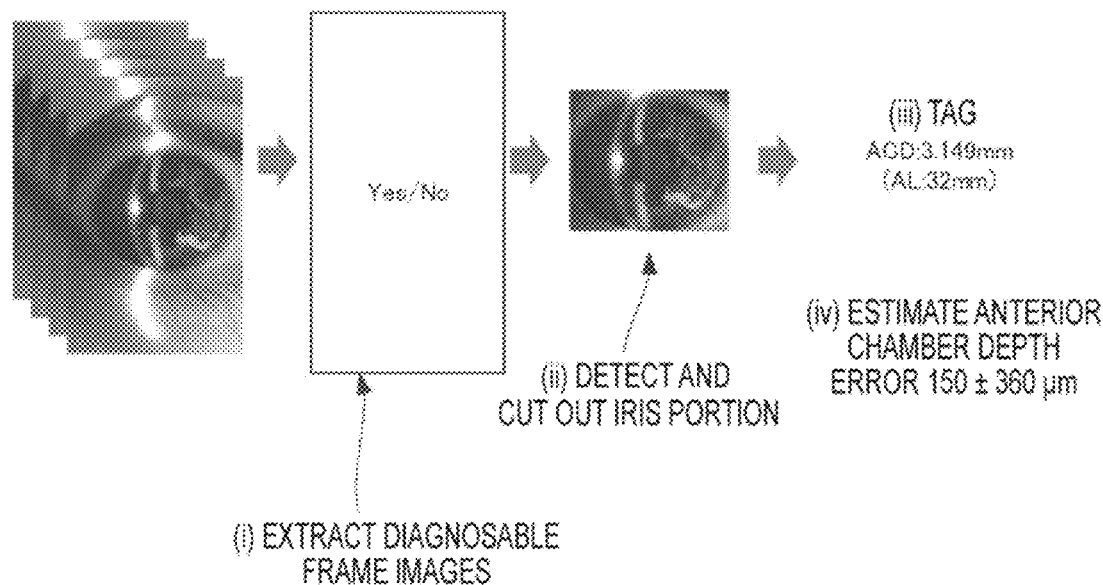
FIG. 33 is a diagram for describing the flow of an experiment of estimating an anterior chamber depth in a diagnosis support server device of a fourth embodiment.

In this experiment, as illustrated in FIG. 33, the anterior chamber tissue of the examined eye E was first captured by the smart eye camera, a diagnosable frame image was then extracted from the captured moving image by the diagnosable frame extracting unit 352 (step i in FIG. 33), and a region image of the iris portion was cut out from the diagnosable frame image (step ii). At this time, as the cutout knowledge, cutout knowledge for cutting out a region image in which the iris was reflected from the diagnosable frame image was utilized.

(1-2) Utilized Diagnosable Frame Image

Here, to capture an image that allows estimation of the anterior chamber depth with a smart eye camera, it is necessary to use the slit light SL as the observation light to irradiate the examined eye E obliquely with the slit light SL, and capture a moving image while crossing the examined eye E with the slit light SL. Therefore, in this experiment, the slit light forming member 61 and the convex lens member 93 were mounted onto the close-up imaging device 20A, which constitutes a smart eye camera, the color filter member 97 was removed, the examined eye E was captured while irradiated with the slit light SL as the observation light, and a moving image including a diagnosable frame image such as exemplified in FIG. 34A was captured.

Figure 34:
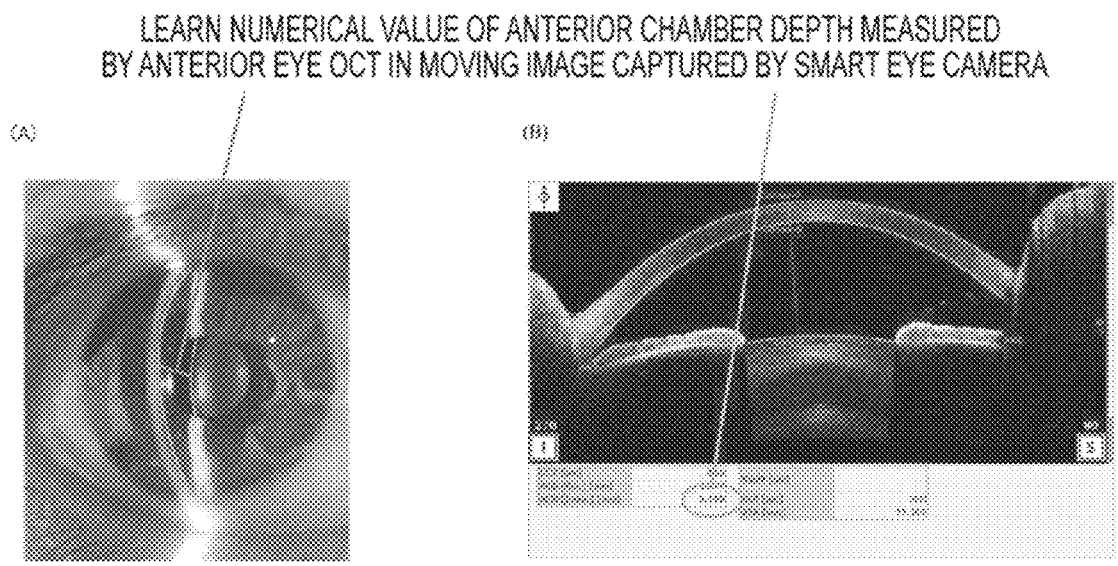
FIGS. 34A and 34B are images for describing an acquisition method of diagnostic knowledge utilized for estimating the anterior chamber depth in the diagnosis support system of the fourth embodiment, and show an example of a diagnosable frame image that can be utilized to estimate the anterior chamber depth and an example of measurement results of the examined eye by anterior eye optical coherence tomography (OCT), respectively.

Further, in a case in which an anterior chamber depth is estimated from a moving image captured by a smart eye camera, it is necessary to use a frame image that can identify the area indicated by the green line in front of the red line in FIG. 34A as a diagnosable frame image. For this reason, in this experiment, the extracting knowledge was used to extract, as a frame image that can be utilized to estimate the anterior chamber depth (that is, diagnosable frame image), a frame image that satisfies, in addition to the above-described three conditions, an additional condition that (condition 4) the pupil is irradiated with slit light SL and the slit light SL is divided into upper and lower parts with the pupil interposed therebetween, as shown in FIG. 33A. Then, in step Sa3 in FIG. 14 mentioned above, a method is adopted in which the diagnosable frame extracting unit 352 extracts a frame image that satisfies these four conditions as a diagnosable frame image, and tags the diagnosable frame image with information parameter values measured by the ophthalmic devices and diagnosis result information to acquire diagnostic knowledge. It should be noted that, in this case, although it is desirable to use a frame image in which a center of the pupil is irradiated with the slit light SL as a diagnosable frame image and it was found that the accuracy of estimating the anterior chamber depth can be improved by using such a frame image, in this experiment, it was also found that it is sufficient if the pupil, in general, is irradiated with the slit light SL, and the center of the pupil may not necessarily be irradiated.

At this time, the region image reflecting the iris was cut out from the diagnosable frame image extracted on the basis of the extracting knowledge, and teacher data was created while tagging the region image cut out from the diagnosable frame image with the information parameter values of anterior chamber depth and axial length (AL) measured by anterior eye OCT (step iii in FIG. 33) to acquire diagnostic knowledge.

Here, the anterior chamber depth is expressed by the numerical value of "ACD=3.149 mm" circled in green on the measurement result GUI of the anterior eye OCT shown in FIG. 34B, and substantially matches a distance from the red point "conea-B" to the red point "lens-F" in FIG. 34B. Further, the value of the anterior chamber depth measured by this anterior eye OCT is theoretically the same distance as the distance indicated by the green line in front of the red line in FIG. 34A. For this reason, in this experiment, while the length of this green line was defined as the value of the anterior chamber depth measured by the anterior eye OCT, the diagnosable frame image was tagged to create the teacher data.

At this time, the annotator input the region image cut out from the diagnosable frame image and the value of the anterior chamber depth measured by anterior eye OCT (for example, the numerical value of "ACD=3.149 mm" in FIG. 34B) and the axial length ("AL=32 mm" exemplified in FIG. 33) obtained by anterior eye OCT into the annotation terminal device 40, thereby tagging the diagnosable frame image with the anterior chamber depth measured value and the axial length measured value to create the teacher data. Then, the diagnostic knowledge was acquired by learning so that the error between the value predicted from the diagnosable frame image and the measured value of anterior eye OCT was "0" (step Sa8 in FIG. 14). It should be noted that the specific process at this time is the same as in FIG. 14 except that the knowledge used as the extracting knowledge is knowledge for extracting images that satisfy the above-described four conditions, and the frame images that satisfy the four conditions are extracted as the diagnosable frame images in step Sa3.

Then, in this experiment, the diagnostic knowledge acquired by the above method was used to estimate the anterior chamber depth on the basis of the moving images captured by the smart eye camera. It should be noted that the operation during anterior chamber depth estimation is basically the same as in FIG. 15. However, in a case in which the anterior chamber depth is estimated, it is necessary to use diagnosable frame images that satisfy the four conditions as described above and thus, in step Sb3, a method is adopted in which the diagnosable frame extracting unit 352 extracts frame images that satisfy the above-described four conditions as diagnosable frame images on the basis of the extracting knowledge. Further, at this time, after extracting the diagnosable frame image that satisfies the above-described four conditions (step i in FIG. 33), the diagnosable frame extracting unit 352 cut out the region image reflecting the iris from the diagnosable frame image as described above (step ii). At this time, the diagnostic knowledge used was knowledge acquired by tagging the region image with the anterior chamber depth measured value and axial length measured value (step iii). Then, the anterior chamber depth was estimated by the health state estimation processing unit 354 on the basis of the diagnostic knowledge and the image captured by the smart eye camera (step iv in FIG. 33).

As a result of the above experiment, it was found that the estimated value of the anterior chamber depth based on the diagnosable frame image extracted from the moving image captured by the smart eye camera was within an error range of 150±360 μm compared to the value actually measured by anterior eye OCT, and the anterior chamber depth can be estimated with very high accuracy.

(2) Glaucoma Onset Risk Determination

As described above, according to this embodiment, the anterior chamber depth of the examined eye E can be estimated with high accuracy, and therefore a risk of glaucoma onset in the examined eye E can also be determined on the basis of a moving image captured by the smart eye camera. In general, a value of anterior chamber depth is related to the risk of glaucoma onset and, when the anterior chamber depth is less than 2.5 mm, the determination can be made that there is a risk of angle-closure glaucoma onset (refer to, for example, https://en.wikipedia.org/wiki/Anterior_chamber of eyeball). For this reason, with the configuration of this embodiment, it is also possible to configure the system to determine the presence or absence of glaucoma onset risk by estimating the anterior chamber depth of the examined eye E, and generate diagnosis support information including the presence or absence of glaucoma onset risk.

(3) Estimation of Corneal Curvature Radius

Further, to confirm the applicability of the diagnosis support system 1 of this embodiment, the inventors measured the corneal curvature radius in the examined eye E using an ophthalmic device such as anterior eye OCT, tagged a diagnosable frame image or a region image of the region reflecting the cornea by the measured value to create teacher data, acquired diagnostic knowledge, and estimated the corneal curvature radius of the examined eye E on the basis of the diagnostic knowledge and the moving image captured by the smart eye camera. As a result, it was found that the value of the corneal curvature radius can also be estimated with the same high accuracy as that of the anterior chamber depth. It should be noted that, in this case, the condition for qualifying as a diagnosable frame image is satisfaction of the above-described four conditions as in the case of anterior chamber depth and thus, in this case as well, the extracting knowledge for extracting frame images that satisfy the above-described four conditions was utilized as the extracting knowledge.

(4) Estimation of Axial Length

Here, it is known that the eyeball has a near spherical shape and that the overall shape of the eyeball depends on the shape of the anterior eye. For example, a strong correlation is recognized between anterior chamber depth and axial length (refer to, for example, https://pubmed.ncbi.nlm-.nih.gov/26107475/). Further, there is a strong correlation between corneal curvature radius and axial length (refer to, for example, https://pubmed.ncbi.nlm.nih.gov/32209342/).

Furthermore, a strong correlation is recognized between the spherical equivalent (SE) value and axial length (for example, https://pubmed.ncbi.nlm.nih.gov/33326192). Accordingly, it is also possible to configure the system to tag the diagnosable frame images or the region images while associating these values with the measured value of the axial length value to create teacher data, and thus estimate the axial length from information parameter values such as anterior chamber depth, corneal curvature radius, and spherical equivalent estimated on the basis of diagnosable frame images.

(5) Estimation of Biopsy (Biotissue Diagnosis) Results

When biopsy results of the examined eye E are estimated from a moving image captured by the smart eye camera in the diagnosis support system 1 of this embodiment, the diagnostic knowledge is basically acquired by the same process as in FIG. 14. At this time, the physician who is the annotator acquires the biopsy results in the biopsied tissue and inputs the diagnosis results based on the biopsy results into the annotation terminal device 40. The annotation terminal device 40 creates teacher data by tagging the diagnosable frame image with the diagnosis result information corresponding to the diagnosis results thus input, and transmits the data to the diagnosis support server device 30. Then, in the diagnostic knowledge acquiring unit 353 of the diagnosis support server device 30, the teacher data is stored in the teacher data storage unit 333 (step Sa6) and, when the quantity of the teacher data reaches a or greater ("Yes" in step Sa7), diagnostic knowledge is acquired and stored on the basis of the teacher data (step Sa8 and Sa9). The process then ends. It should be noted that, in addition to eyelid tissue and anterior eye tissue, intraocular tissue and fundus tissue can be targeted for biopsy. At this time, in a case in which the target tissues are the eyelid tissue and the anterior eye tissue, the slit light SL, white diffused light, and blue light can be utilized as the observation light. On the other hand, in a case in which the fundus tissue is targeted, it is necessary to mount the close-up imaging device 20B in the second embodiment onto the mobile communication terminal device 10 and utilize linearly polarized light as the observation light. It should be noted that, in the case of fundus tissue, in addition to biopsy results, the diagnosable frame images or region images are tagged with the information parameter values of retinal thickness, optic disk diameter, retinochoroidal vessels, and the like measured by OCT along with the diagnosis result information to create teacher data, making it possible to estimate these information parameter values with high accuracy, and estimate the presence or absence of the disease in the fundus tissue of the examined eye E with high accuracy. In particular, a moving image captured by a smart eye camera can be captured at very high resolution (for example, 4K or 8K resolution) using the out-camera module of the mobile communication terminal device 10, and thus pathological findings that can only be understood by biopsy can be estimated with high accuracy from the moving image captured by the smart eye camera by cutting out and enlarging the region image reflecting the target area (for example, eyelid or the like) when the moving image data is uploaded.

As described above, according to the diagnosis support system 1 of this embodiment, it is possible to estimate the values of various information parameters related to the examined eye E from the moving image captured by the smart eye camera, and thus appropriately estimate in detail the health state of the eye of the patient, even in a region where equipment, physicians, and the like are in short supply, such as developing countries and remote places where various ophthalmic devices cannot be installed, and utilize the system for diagnosis of various diseases. It should be noted that, in the configuration of this embodiment, a configuration may be adopted in which, as in the above-described first embodiment, the probability of being classified as "Diagnosable" is calculated for each diagnosable frame image, a plurality of diagnosable frame images are extracted, the information parameter values are estimated for each diagnosable frame image and, while weighting each estimated value by the probability of being classified as "Diagnosable," the most plausible information parameter value for the examined eye E is estimated. The process in this case is the same as in the first embodiment, except that the information parameter value instead of the state of the disease is used as the estimation target. Further, in the configuration of this embodiment, as in Modification 4, the system may be configured to construct a three-dimensional image, acquire diagnostic knowledge on the basis of the three-dimensional image, and estimate the information parameter value on the basis of the diagnostic knowledge and the three-dimensional image. Furthermore, it should be noted that, in the configuration of this embodiment, it is desirable to adopt a configuration in which a plurality of information parameter values (such as anterior chamber depth, corneal curvature radius, or the like, for example) are estimated at once and made available by capturing a single moving image, as in Modification 6. In this case, the system need only be configured to store the plurality of diagnostic knowledge for estimating the information parameter values in the diagnostic knowledge storage unit 334 in advance and, when the moving image data is uploaded from the smart eye camera, to extract, for each information parameter value, the diagnosable frame images for estimating the information parameter value, and to estimate the plurality of information parameter values in some tissue in the examined eye E at once on the basis of the extracted diagnosable frame images and the diagnostic knowledge for the corresponding information parameter values. In addition, in this case, as in Modification 6, the system may be configured to generate diagnosis support information describing the estimation results of the plurality of information parameter values in a list format.

DESCRIPTIONS OF REFERENCE NUMERALS

1: Diagnosis support system, 2: Polarizing filter (vertically polarized light), 3: Polarizing filter (horizontally polarized light), 4: Color filter (orange), 8: Plate-shaped filter, 10: Mobile communication terminal device, 20, 20A, 20B: Close-up imaging device, 30: Diagnosis support server device, 310: Communication control unit, 320: ROM/RAM, 330: Storage device, 331: Program storage unit, 332: Extracting knowledge storage unit, 333: Teacher data storage unit, 334: Diagnostic knowledge storage unit, 340: Server management control unit, 350: Diagnosis processing unit, 351: Moving image data acquiring unit, 352: Diagnosable frame extracting unit: 353: Diagnostic knowledge acquiring unit, 354: Health state estimation processing unit, 355: Diagnosis support information generating unit, 356: Diagnosis support information distributing unit, 61: Slit light forming member: 61': Main body part, 62: Cylindrical lens, 63: Upper holding member, 64: Lower holding member: 65: First reflecting mirror, 66: Second reflecting mirror, 67: Slit, 68: Mounting part, 69: Step part, 80: Housing, 81: Outer wall part, 82: Front wall, 83: Back wall, 84: Left wall, 85: Right wall, 86: Upper wall, 87: Lower wall, 88: Hole in front wall, 90: Front surface plate, 90a: Opened left edge part, 90b: Right edge part, 90c: Upper edge part, 90d: Lower edge part, 91: Imaging camera lens, 92: Light source, 93: Convex lens member, 94: Convex lens mounting hole, 95: Hole, 96: Convex lens, 97: Color filter member, 98: Hole, 180: Tubular member, 181: Mounting part, 182, 182a, 182b: Tube part, 183: Convex lens, 184: Opening

What is claimed is:

1. A diagnosis support device comprising:
acquisition means for acquiring an image of an examined eye captured by a mobile communication terminal device with a close-up imaging device mounted thereto,
the mobile communication terminal device including
a light source, and
an imaging camera lens,
the close-up imaging device including at least
(a) an observation light irradiating member that irradiates tissue to be observed of the examined eye with, as observation light, any one of slit light, blue light, and linearly polarized light generated on the basis of light-source light emitted from the light source, or irradiates the tissue to be observed with, as the observation light, the light-source light passed as is, and
(b) a convex lens member that concentrates, of the observation light, light including reflected light in the tissue to be observed, on the imaging camera lens,
the captured image including one or more first frame images that can be utilized for estimating at least one of
(i) a health state of the examined eye, and
(ii) one or more information parameter values including any one or more of a distance, an angle, and an area in some tissue of the examined eye;
first storage means for storing, in advance, first knowledge for extracting the one or more first frame images from the captured image acquired,
first extraction means for extracting, on the basis of the first knowledge, the one or more first frame images included in the captured image acquired;
second storage means for storing, on the basis of the captured image, second knowledge for estimating at least one of
(i) the health state of the examined eye, and
(ii) the one or more information parameter values;
estimation means for estimating, on the basis of the one or more first frame images extracted and the second knowledge, at least one of
(i) the health state of the examined eye reflected in the captured image acquired, and
(ii) the one or more information parameter values;
generation means for generating diagnosis support information including at least one of the health state of the examined eye and the one or more information parameter values estimated; and
distribution means for distributing the diagnosis support information generated to an external equipment.

2. The diagnosis support device according to claim 1, wherein
the first extraction means calculates a probability of each frame image included in the captured image qualifying as the first frame image on the basis of the frame images included in the captured image and the first knowledge, and extracts the first frame image on the basis of the calculated probability.

3. The diagnosis support device according to claim 2, wherein
the first extraction means extracts, as the one or more first frame images, a plurality of the frame images with the calculated probability being high, and
the estimation means estimates at least one of (i) the health state of the examined eye and (ii) the one or more information parameter values for each of the one or more first frame images on the basis of the plurality of first frame images extracted and the second knowledge, and estimates at least one of a most plausible health state of the examined eye and the one or more information parameter values while weighting, by the calculated probability, the health state and the one or more information parameter values estimated.

4. The diagnosis support device according to claim 1, wherein
the acquisition means acquires the captured image captured while at least one of an eyelid or an anterior eye tissue of the examined eye is irradiated with the slit light generated on the basis of the light-source light as the observation light,
the first storage means stores, in advance, as the first knowledge, knowledge for extracting the one or more first frame images that can be utilized for estimating at least one of
(i) a state of a disease that develops in the eyelid and the anterior eye tissue of the examined eye, and
(ii) the one or more information parameter values related to the eyelid and the anterior eye tissue,
the second storage means stores, as the second knowledge, knowledge for estimating at least one of
(i) the state of the disease that develops in the eyelid and the anterior eye tissue of the examined eye, and
(ii) the one or more information parameter values related to the eyelid and the anterior eye tissue, and
the estimation means estimates, on the basis of the one or more first frame images extracted and the second knowledge, at least one of
(i) the state of the disease in at least one of the eyelid and the anterior eye tissue of the examined eye, and
(ii) the one or more information parameter values related to the eyelid and the anterior eye tissue.

5. The diagnosis support device according to claim 1, wherein
the acquisition means acquires the captured image captured while irradiating at least one of a cornea and a conjunctiva of the examined eye with the blue light generated on the basis of the light-source light as the observation light, with an injury that occurred in a tissue of at least one of the cornea and the conjunctiva of the examined eye being contrasted by a contrast medium,
the first storage means stores, in advance, as the first knowledge, knowledge for extracting the one or more first frame images that can be utilized for diagnosis of the state of the injury that occurred in the tissue of at least one of the cornea and the conjunctiva of the examined eye,
the second storage means stores, in advance, as the second knowledge, knowledge for estimating a state of a disease in at least one of the cornea and the conjunctiva from the state of the injury that occurred in the tissue of at least one of the cornea and the conjunctiva of the examined eye, and
the estimation means estimates, on the basis of the one or more first frame images extracted and the second knowledge, the state of the disease in at least one of the tissues of the cornea and conjunctiva of the examined eye.

6. The diagnosis support device according to claim 1, wherein
   the acquisition means acquires the captured image captured while fundus tissue of the examined eye is irradiated with the linearly polarized light generated on the basis of the light-source light as the observation light,
   the first storage means stores, in advance, as the first knowledge, knowledge for extracting the one or more first frame images that can be utilized for estimating at least one of
   (i) a state of a disease that develops in the fundus tissue of the examined eye, and
   (ii) the one or more information parameter values related to the fundus tissue,
   the second storage means stores, as the second knowledge, knowledge for estimating at least one of
   (i) the state of the disease in the fundus tissue of the examined eye, and
   (ii) the one or more information parameter value related to the fundus tissue, and
   the estimation means estimates, on the basis of the one or more first frame images extracted and the second knowledge, at least one of
   (i) the state of the disease in the fundus tissue of the examined eye, and
   (ii) the one or more information parameter values related to the fundus tissue.

7. The diagnosis support device according to claim 1, wherein
   the acquisition means acquires the captured image captured while the tissue to be observed of the examined eye is irradiated with the light-source light as the observation light as is,
   the first storage means stores, in advance, as the first knowledge, knowledge for extracting the one or more first frame images that can be utilized for estimating at least one of
   (i) a state of a disease that develops in tissue of at least one of an eyelid, an eye surface, a cornea, and a conjunctiva of the examined eye, and
   (ii) the one or more information parameter values related to the tissue of at least one of the eyelid, the eye surface, the cornea, and the conjunctiva of the examined eye,
   the second storage means stores, in advance, as the second knowledge, knowledge for estimating at least one of
   (i) the state of the disease in the tissue of at least one of the eyelid, the eye surface, the cornea, and the conjunctiva of the examined eye, and
   (ii) the one or more information parameter values related to the tissue of at least one of the eyelid, the eye surface, the cornea, and the conjunctiva of the examined eye, and
   the estimation means estimates, on the basis of the one or more first frame images extracted and the second knowledge, at least one of
   (i) the state of the disease in the tissue of at least one of the eyelid, the eye surface, the cornea, and the conjunctiva of the examined eye, and
   (ii) the one or more information parameter values related to the tissue of at least one of the eyelid, the eye surface, the cornea, and the conjunctiva of the examined eye.

8. The diagnosis support device according to claim 1, further comprising:
   learning means for acquiring the second knowledge by executing at least one of machine learning and data mining on the basis of the one or more first frame images extracted by the first extraction means, and storing the second knowledge acquired in the second storage means,
   the estimation means estimating, on the basis of the second knowledge stored in the second storage means by the learning means and the one or more first frame images extracted, at least one of the state of a disease of the examined eye and the one or more information parameter values.

9. The diagnosis support device according to claim 8, wherein
   the learning means, while acquiring diagnosis result information indicating a diagnosis result by a physician, based on the one or more first frame images extracted by the first extraction means, and setting the diagnosis result information and the corresponding one or more first frame images as teacher data, acquires the second knowledge by executing at least one of machine learning and data mining and stores the second knowledge in the second storage means.

10. The diagnosis support device according to claim 9, wherein
    the first storage means stores, as the first knowledge, a plurality of knowledge for extracting, for each disease that may develop in each tissue constituting the examined eye, the one or more first frame images that can be utilized for diagnosis of the disease,
    the first extraction means extracts, for each of the diseases, the one or more first frame images that can be utilized for state estimation of the disease, on the basis of the first knowledge, and
    the learning means, while acquiring the diagnosis result information related to each disease on the basis of the one or more first frame images extracted and corresponding to the disease and setting the diagnosis result information and the corresponding one or more first frame images as teacher data, acquires, for each disease, the second knowledge required for diagnosis of the disease by executing at least one of machine learning and data mining, and stores the second knowledge acquired in association with the corresponding disease in the second storage means.

11. The diagnosis support device according to claim 9, wherein
    the learning means acquires the one or more information parameter values of the examined eye, and acquires the second knowledge on the basis of
    (a) the one or more information parameter values acquired,
    (b) the diagnosis result information, and
    (c) the one or more first frame images or the region image cut out.

12. The diagnosis support device according to claim 1, wherein
    the first storage means stores, as the first knowledge, a plurality of knowledge for extracting, for each disease that may develop in each tissue constituting the examined eye, the one or more first frame images that can be utilized for diagnosis of the disease,
    the second storage means stores, for each of the diseases, a plurality of knowledge for estimating a state of the disease, as the second knowledge, the first extraction means extracts, for each of the diseases, the one or more first frame images that can be utilized for diagnosis of the disease, on the basis of the first knowledge, the estimation means estimates a state of each disease in the examined eye on the basis of the one or more first frame images extracted for each of the diseases and the second knowledge of the corresponding disease, and the generation means generates information including the state of each of the diseases estimated as the diagnosis support information.

13. The diagnosis support device according to claim 1, further comprising:

labeling means for labeling a tissue name corresponding to a tissue of the examined eye in focus in each of the frame images included in the captured image; and second extraction means for extracting, as a second frame image, the frame image having a largest area of a pixel region reflecting tissue in focus in each of the frame images labeled, the generation means generating the diagnosis support information including the second frame image extracted.

14. The diagnosis support device according to claim 1, further comprising:

three-dimensional image construction means for constructing a three-dimensional image of the examined eye by layering, in correspondence with a focal length, each frame image included in the captured moving image acquired, the second storage means storing, as the second knowledge, on the basis of the three-dimensional image, knowledge for estimating at least one of (i) the health state of the examined eye, and (ii) the one or more information parameter values, and the estimation means estimating, on the basis of the three-dimensional image generated and the second knowledge, at least one of (i) the health state of the examined eye, and (ii) the one or more information parameter values.

15. The diagnosis support device according to claim 1, further comprising:

cutout means for cutting out a region reflecting the tissue to be targeted for estimating the health state as a region image in the one or more first frame images extracted by the first extraction means, the second storage means storing, as the second knowledge, on the basis of the region image cut out from the captured image, knowledge for estimating at least one of (i) the health state of the examined eye, and (ii) the one or more information parameter values including any one or more of the distance, the angle, and the area in some tissue of the examined eye, and the estimation means estimating, on the basis of the region image and the second knowledge, at least one of (i) the health state of the examined eye, and (ii) the one or more information parameter values.

16. The diagnosis support device according to claim 15, wherein the learning means acquires the second knowledge by executing at least one of machine learning and data mining on the basis of the region image cut out and the diagnosis result information.

17. A diagnosis support system comprising:

a mobile communication terminal device including a light source, and an imaging camera lens, the mobile communication terminal device being provided with a close-up imaging device including at least (a) an observation light irradiating member that irradiates tissue to be observed of the examined eye with, as observation light, any one of slit light, blue light, and linearly polarized light generated on the basis of light-source light emitted from the light source, or irradiates the tissue to be observed with, as the observation light, the light-source light passed as is, and (b) a convex lens member that condenses, of the observation light, light including reflected light in the tissue to be observed, on the imaging camera lens; and a diagnosis support device that supports diagnosis of the examined eye by estimating at least one of (i) a health state of the examined eye, and (ii) one or more information parameter values including any one or more of a distance, an angle, and an area in some tissue of the examined eye on the basis of an image of the examined eye captured by the mobile communication terminal device, the image including one or more first frame images that can be utilized to estimate at least one of the health state of the examined eye and the one or more information parameter values, the diagnosis support device including acquisition means for acquiring the captured image, first storage means for storing, in advance, first knowledge for extracting the one or more first frame images from the captured image acquired, first extraction means for extracting, on the basis of the first knowledge, the one or more first frame images included in the captured image acquired, second storage means for storing, on the basis of the captured image, second knowledge for estimating at least one of (i) the health state of the examined eye, and (ii) the one or more information parameter values;

estimation means for estimating, on the basis of the one or more first frame images extracted and the second knowledge, at least one of (i) the health state of the examined eye reflected in the captured image acquired, and (ii) the one or more information parameter values;

generation means for generating diagnosis support information including at least one of the health state of the examined eye and the one or more information parameter values estimated; and distribution means for distributing the diagnosis support information generated to an external equipment.

18. A program configured to cause a computer, which functions as a diagnosis support device that supports diagnosis of an examined eye on the basis of an image of the examined eye captured by a mobile communication terminal device including a light source, and an imaging camera lens, the mobile communication terminal device being provided with a close-up imaging device including at least (a) an observation light irradiating member that irradiates tissue to be observed of the examined eye with, as observation light, any one of slit light, blue light, and linearly polarized light generated on the basis of light-source light emitted from the light source, or irradiates the tissue to be observed with, as the observation light, the light-source light passed as is, and (b) a convex lens member that condenses, of the observation light, light including reflected light in the tissue to be observed, on the imaging camera lens, the captured image including one or more first frame images that can be utilized for estimating at least one of (i) a health state of the examined eye, and (ii) one or more information parameter values including any one or more of a distance, an angle, and an area in some tissue of the examined eye, and the computer including (A) first storage means for storing, in advance, first knowledge for extracting the one or more first frame images from the captured image, and (B) second storage means for storing, on the basis of the captured image, second knowledge for estimating at least one of (i) the health state of the examined eye, and (ii) the one or more information parameter values, to function as:

acquisition means for acquiring the captured image;

first extraction means for extracting, on the basis of the first knowledge, the one or more first frame images included in the captured image acquired;

estimation means for estimating, on the basis of the one or more first frame image extracted and the second knowledge, at least one of (i) the health state of the examined eye reflected in the captured image acquired, and (ii) the one or more information parameter values;

generation means for generating diagnosis support information including at least one of the health state of the examined eye and the one or more information parameter values estimated; and distribution means for distributing the diagnosis support information generated to an external equipment.

* * * * *